US008440627B2

(12) United States Patent
Kuliopulos et al.

(10) Patent No.: US 8,440,627 B2
(45) Date of Patent: May 14, 2013

(54) G PROTEIN COUPLED RECEPTOR AGONISTS AND ANTAGONISTS AND METHODS OF USE

(75) Inventors: Athan Kuliopulos, Winchester, MA (US); Lidija Covic, Lexington, MA (US); Nicole Kaneider, Innsbruck (AT)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 11/667,042

(22) PCT Filed: Nov. 4, 2005

(86) PCT No.: PCT/US2005/039959
§ 371 (c)(1),
(2), (4) Date: Jan. 15, 2008

(87) PCT Pub. No.: WO2006/052723
PCT Pub. Date: May 18, 2006

(65) Prior Publication Data
US 2008/0214451 A1 Sep. 4, 2008

Related U.S. Application Data

(60) Provisional application No. 60/625,706, filed on Nov. 4, 2004.

(51) Int. Cl.
*C12P 21/04* (2006.01)
*C07K 14/705* (2006.01)
*A61K 38/04* (2006.01)

(52) U.S. Cl.
USPC ............................ 514/20.6; 435/69.7; 530/402

(58) Field of Classification Search .................. None
See application file for complete search history.

(56) References Cited

U.S. PATENT DOCUMENTS

| | | | | |
|---|---|---|---|---|
| 5,508,384 A * | 4/1996 | Murphy et al. | ............... | 530/324 |
| 5,747,267 A | 5/1998 | Mulvihill et al. | ............ | 435/7.21 |
| 5,750,370 A * | 5/1998 | Li et al. | ........................ | 435/69.1 |
| 5,925,549 A | 7/1999 | Hsueh et al. | .................. | 435/69.7 |
| 5,935,936 A * | 8/1999 | Fasbender et al. | .......... | 514/44 R |
| 6,096,868 A | 8/2000 | Halsey et al. | ................ | 530/350 |
| 6,111,075 A | 8/2000 | Xu et al. | ........................ | 530/350 |
| 6,111,076 A | 8/2000 | Fukusumi et al. | ............ | 530/350 |
| 6,162,808 A | 12/2000 | Kindon et al. | ................ | 514/269 |
| 6,548,499 B1 | 4/2003 | Carson | | |
| 6,864,229 B2 | 3/2005 | Kuliopulos et al. | ............... | 514/2 |
| 7,304,127 B2 * | 12/2007 | Saxinger | ....................... | 530/326 |
| 2003/0148449 A1 | 8/2003 | Kuliopulos et al. | .......... | 435/69.1 |
| 2006/0166274 A1 | 7/2006 | Kuliopulos et al. | .............. | 435/7.1 |
| 2007/0179090 A1 | 8/2007 | Kuliopulos et al. | ............... | 514/12 |
| 2008/0234183 A1* | 9/2008 | Hallbrink et al. | ............... | 514/12 |

FOREIGN PATENT DOCUMENTS

| | | |
|---|---|---|
| AU | 2005304963 A1 | 5/2006 |
| BR | PI05170583 A | 9/2008 |
| CA | 2586344 A1 | 5/2006 |
| CN | 101094866 | 12/2007 |
| EP | 1814911 A2 | 8/2007 |
| JP | 2008519039 T | 6/2008 |
| WO | WO 98/00538 | 1/1998 |
| WO | WO 98/34948 | 8/1998 |
| WO | WO 99/43711 | 9/1999 |
| WO | WO 99/62494 | 12/1999 |
| WO | 200181408 A2 | 11/2001 |
| WO | WO 01/81408 A3 | 11/2001 |
| WO | 2006052723 A2 | 5/2006 |

OTHER PUBLICATIONS

Loetscher et al., Journal of Biological Chemistry, 269:232-237, 1994.*
Anand-Srivastava et al., "Cytoplasmic domain of natriuretic peptide receptor-C inhibits adenylyn cyclase", *J. Biol. Chem.*, 271(32):19324-19329 (1996).
Andrade-Gordon et al., "Design, Synthesis, and Biological Characterization of a Peptide-Mimetic Antagonist for a Tethered-Ligand Receptor", *Proc. Natl. Acad. Sci. USA*, 96(22):12257-12262 (1999).
Aoki et al., "A novel human G-protein-coupled receptor, EDG7, for lysophosphatidic acid with unsaturated fatty-acid moiety", *Annals New York Academy of Sciences: Lysophospholipids and Eicosanoids in Biology and Pathophysiologi*, pp. 263-266 (2000).
Bernatowicz et al., "Development of Potent Thrombin Receptor Antagonist Peptides", *J. Med. Chem.*, 39:4879-4887 (1996).
Cotecchia et al., "Discrete Amino Acid Sequences of the α1-Adrenergic Receptor Determine the Selectivity of Coupling to Phosphatidylinositol Hydrolysis", *J. Biol. Chem.*, 267(3):1633-1639 (1992).
Coughlin et al., "PARticipation in inflammation", *J. Lin. Invest.*, 111(1):25-27 (2003).
Covic et al., "Intracellular liganding of the PAR1 thrombin receptor by a novel class of cell penetrating peptides", *Blood* 96(11): 244a, Abstract #1050 (2000).
Covic et al., "Activation and inhibition of G protein-coupled receptors by cell-penetrating membrane-tethered peptides", *Proc. Natl. Acad. Sci. USA*, 99(2): 643-648 (2002).
Covic et al., "Biphasic Kinetics of Activation and Signaling for PAR1 and PAR4 Thrombin Receptors in Platelets", *Biochemistry*, 39:5458-5467 (2000).
Dalman et al., "Two Peptides from the $\alpha_{2A}$-adrenergic receptor alter receptor G protein coupling by distinct mechanisms", *J. Biol. Chem.*, 266(17):11025-11029 (1991).
Elliot et al., "Maleimide-Functionalized Lipids that Anchor Polypeptides to Lipid Bilayers and Membranes", *Bioconjugate Chem.*, 11(6):832-841 (2000).
Faruqi et al., "Structure-Function Analysis of Protease-activated Receptor 4 Tethered Ligand Peptides", *J. Biol. Chem.*, 275(26):19728-19734 (2000).
George et al., "A Transmembrane Domain-Derived Peptide Inhibits D1 Dopamine Receptor Function without Affecting Receptor Oligomerization", *J. Biol. Chem.*, 273(46):30244-30248 (1998).

(Continued)

*Primary Examiner* — Marianne P Allen
(74) *Attorney, Agent, or Firm* — McDermott Will & Emery LLP

(57) ABSTRACT

The invention relates generally to G protein coupled receptors (GPCRs) and in particular to GPCR agonists and antagonists, use of these compounds and their pharmaceutical compositions, e.g., in the treatment, modulation and/or prevention of physiological conditions associated with GPCRs, such as in treating conditions in which chemokine receptors play a role, e.g., sepsis, arthritis, inflammation and autoimmune diseases.

37 Claims, 28 Drawing Sheets

OTHER PUBLICATIONS

Gether et al., "G Protein-coupled Receptors", J. Biol. Chem., 273(29):17979-17982 (1998).
Gilman, A.G., "G Proteins: Transducers of Receptor-Generated Signals", Ann. Rev. Biochem., 56:615-649 (1987).
Hammes et al., "Protease-Activated Receptor-1 Can Mediate Responses to SFLLRN in Thrombin-Desensitized Cells: Evidence for a Novel Mechanism for Preventing or Terminating Signaling by PAR1's Tethered Ligand" Biochem., 38: 2486-2493 (1999).
Higashijima et al., "Mastoparan, a Peptide Toxin from Wasp Venom, Mimics Receptors by Activating GTP-binding Regulatory Proteins (G Proteins)", J. Biol. Chem., 263(14):6491-6494 (1988).
Ishii et al., "Inhibition of thrombin receptor signaling by a G-protein coupled receptor kinase", J. Biol. Chem., 269(2):1125-1130 (1994).
Ishii et al., "Determinants of Thrombin Receptor Cleavage", J. Biol. Chem., 270(27):16435-16440 (1995).
Kahn et al., "A Dual Thrombin Receptor System for Platelet Activation", Nature 394:690-694 (1998).
Kaneider et al., "Reversing systemic inflammatory response syndrome with chemokine receptor pepducins", Nat. Med., 11(6):661-665 (2005).
Keane et al., "Depletion of CXCR2 inhibits tumor growth and angiogenesis in a murine model of lung cancer", J. Immunol., 172(5):2853-2860 (2004).
Kjelsberg et al., "Constitutive Activator of the $\alpha_{1B}$ Adrenergic Receptor by All Amino Acid Substitutions at a Single Site", J. Biol. Chem., 267(3):1430-1433 (1992).
Kostenis et al., "Molecular Basis of Receptor/G Protein Coupling Sensitivity Studies by Coexpression of Wild Type and Mutant m2 Muscarinic Receptors with Mutant $G\alpha_q$ Subunits", Biochemistry, 36:1487-1495 (1997).
Kuliopulos et al., "Plasmin Desensitization of the PAR1 Thrombin Receptor: Kinetics, Sites of Truncation, and Implications for Thrombolytic Therapy", Biochemistry, 38:4572-4585 (1999).
Luttrell et al., "Antagonism of Catecholamine Receptor Signaling by Expression of Cytoplasmic Domains of the Receptors", Science, 259:1453-1457 (1993).
Megaritis et al., "Functional Domains of δ- and -Opioid Receptors Responsible for Adenylyl Cyclase Inhibition", Receptors and Channels, 7:199-212 (2000).
Merkouris et al., "Identification of the Critical Domains of the δ-Opioid Receptor Involved in G Protein Coupling Using Site-Specific Synthetic Peptides", Mol. Pharmacol., 50:985-993 (1996).
Milligan, G., "Receptors as Kissing Cousins", Science, 288:65-67 (2000).
Moro et al., "Hydrophobic Amino Acid in the i2 Loop Plays a Key Role in Receptor-G Protein Coupling", J. Biol. Chem., 268(30): 22273-22276 (1993).
Nystedt et al., "Molecular Cloning of a Potential Proteinase Activated Receptor", Proc. Natl. Acad. Sci. USA, 91:9208-9212 (1994).
Okamoto et al., "Identification of a $G_S$ Activator Region of the β2-Adrenergic Receptor That is Autoregulated via Protein Kinase A-Dependent Phosphorylation", Cell, 67:723-730 (1991).
Oosterom et al., "Common Structure for Melanocortin-4 Receptor Selectivity of Structurally Unrelated Melanocortin Agonist and Endogenous Antagonist, Agouti Protein", J. Biol. Chem., 276(2):931-936 (2001).
Palczewski et al., "Crystal Structure of Rhodopsin: A G Protein-Coupled Receptor", Science, 289:739-745 (2000).
Pfeiffer et al., "Homo- and Heterodimerization of Somatostatin Receptor Subtypes", J. Biol. Chem., 276(17):14027-14036 (2001).
Rojas et al., "Genetic Engineering of Proteins with Cell Membrane Permeability", Nat. Biotechnol., 16:370-375 (1998).
Schwarze et al., "In Vivo Protein Transduction: Delivery of a Biologically Active Protein into the Mouse", Science, 285:1569-1572 (1999).
Stephens et al., "A Sequence within the Cytoplasmic Tail of GpIIb Independently Activates Platlet Aggregation and Thromboxane Synthesis", J. Biol. Chem., 273(32):20317-20322 (1998).
Swift et al., "PAR1 Thrombin Receptor-G Protein Interactions", J. Biol. Chem., 275(4): 2627-2635 (2000).
Tarasova et al., "Inhibition of G-protein-coupled Receptor Function by Disruption of Transmembrane Domain Interactions", J. Biol. Chem., 274:34911-34915 (1999).
Tarzami et al., "Opposing effects mediated by the chemokine receptor CXCR2 on myocardial ischemia-reperfusion injury: recruitment of potentially damaging neutrophils and direct myocardial protection", Circulation, 108(19):2387-2392 (2003).
Trejo et al., "The Cytoplasmic Tails of Protease-activated Receptor-1 and Substance P Receptor Specify Sorting to Lysosomes versus Recycling", J. Biol. Chem., 274(4): 2216-2224 (1999).
Vergnolle et al., "Protease-Activated Receptors in Inflammation, Neuronal Signaling and Pain", TRENDS Pharmacol. Sci., 22(3):146-152 (2001).
Wikstrom et al., "The Properties of Peptidyl Diazoethanes and Chloroethanes as Protease Inactivators", Archives of Biochem. & Biophysics, 270(1):286-293 (1989).
Xu et al., "Cloning and Characterization of Human Protease-Activated Receptor 4", Proc. Natl. Acad. Sci. USA, 95:6642-6646 (1998).
Ballesteros et al., "Integrated Methods for the Construction of Three-Dimensional Models and Computational Probing of Structure-Function Relations in G Protein-Coupled Receptors," Methods in Neurosciences, 25:366-428 (1995).
Gether, "Uncovering Molecular Mechanisms Involved in Activation of G Protein-Coupled Receptors," Endocrine Reviews, 21:90-113 (2000).
Kuliopulos et al., "Blocking receptors on the inside: pepducin-based intervention of PAR signaling and thromobosis", Life Sci., 74(2-3):255-262 (2003).
Leger et al., "Blocking the Protease-Activated Receptor 1-4 Heterodimer in Platelet-Mediated Thrombosis," Circulation, 113:1244-1254 (2006).
Mirzadegan et al., "Sequence Analyses of G-Protein-Coupled Receptors: Similarities to Rhodopsin," Biochemistry, 42:2759-2767 (2003).
Aebischer et al., "Intrathecal Delivery of CNTF using Encapsulated Genetically Modified Xenogeneic Cells in Amyotrophic Lateral Sclerosis Patients," Nature Medicine, 2:696-699 (1996).
Agarwal et al., "Identification of a Metalloprotease-Chemokine Signaling System in the Ovarian Cancer Microenvironment: Implications for Antiangiogenic Therapy," Cancer Research, 70:5880-5890 (2010).
Agarwal et al., "Targeting a Metalloprotease-PAR1 Signaling System with Cell-Penetrating Pepducins Inhibits Angiogenesis, Ascites, and Progression of Ovarian Cancer," Mol. Cancer Ther. 7:2746-2757 (2008).
Boire et al., "PAR1 is a Matrix Metalloprotease-1 Receptor that Promotes Invasion and Tumorigenesis of Breast Cancer Cells," Cell, 120:303-313 (2005).
Cheung et al., "Specific Activation of $G_s$ by Synthetic Peptides Corresponding to an Intracellular Loop of the β-Adrenergic Receptor," FEBS Letters, 279:277-280 (1991).
Eisenstein et al., "GPCRs: Insane in the Membrane," Nature Methods, 6:929-933 (2009).
Kai et al., "G-Protein Binding Domains of the Angiotensin II $AT_{1A}$ Receptors Mapped with Synthetic Peptides Selected from the Receptor Sequence," Biochem J., 332:781-787 (1998).
Kaneider et al., "'Role Reversal' for the Receptor PAR1 in Sepsis-Induced Vascular Damage," Nature Immunology, 8:1303-1312 (2007).
Milligan et al., "Chimaeric G Proteins: Their Potential Use in Drug Discovery," TiPS, 20:118-124 (1999).
Mukherjee et al., "β-Arrestin-Dependent Desensitization of Luteinizing Hormone/Choriogonadotropin Receptor is Prevented by a Synthetic Peptide Corresponding to the Third Intracellular Loop of the Receptor," The Journal of Biological Chemistry, 274:12984-12989 (1999).
Okamoto et al., "A Simple Structure Encodes G Protein-Activating Function of the IGF-II/Mannose 6-Phosphate Receptor," Cell, 62:709-717 (1990).
Shinagawa et al., "Circular Dichroism Studies of the Interaction between Synthetic Peptides Corresponding to Intracellular Loops of β-Adrenergic Receptors and Phospholipid Vesicles," J. Biochem, 115:463-468 (1994).

Tardieu, "Second Messengers' Accumulation Assays Advanced Tools to Investigate All Compound Classes of GPCR Activations", Genetic Engineering Biotechnology News, Assay Tutorials, vol. 29 (2009).

Taylor et al., "Binding of an α2 Adrenergic Receptor Third Intracellular Loop Peptide to Gβ and the Amino Terminus of Gα," The Journal of Biological Chemistry, 269:27618-27624 (1994).

Taylor et al., "Peptides as Probes for G Protein Signal Transduction," Cellular Signaling, 6:841-849 (1994).

Tressel et al., "Pharmacology. Biodistribution, and Efficacy of GPCR-Based Pepducins in Disease Models," Methods in Molecular Biology, 683:259-275 (2011).

Trivedi et al., "Platelet Matrix Metalloprotease-1 Mediates Thrombogenesis by Activating PAR1 at a Cryptic Ligand Site," Cell, 137:332-343 (2009).

Varrault et al., "5-Hydroxytryptamine$_{1A}$ Receptor Synthetic Peptides," The Journal of Biological Chemistry, 269:16720-16735 (1994).

Vitiello et al., "Development of a Lipopeptide-Based Therapeutic Vaccine to Treat Chronic HBV Infection," J. Clin. Invest., 95:341-349 (1995).

Voss et al., "Amphipathic α-Helical Structure Does Not Predict the Ability of Receptor-Derived Synthetic Peptides to Interact with Guanine Nucleotide-Binding Regulatory Proteins," The Journal of Biological Chemistry, 268:4637-4642 (1993).

Wagner et al., "Differential Regulation of G Protein α-Subunit GTPase Activity by Peptides Derived from the Third Cytoplasmic Loop of the α$_2$-Adrenergic Receptor," FEBS Letters, 365:13-17 1995.

Wakamatsu et al., "Interaction of Peptide Fragments Corresponding to Cytoplasmic Loops of G Protein-Coupled Receptors with G Protein and Phospholipid Membrane," Pept. Chem., 1992:677-680 (1993).

Wilson et al., "Orphan G-Protein-Coupled Receptors: The Next Generation of Drug Targets," British Journal of Pharmacology, 125:1387-1392 (1998).

Yu et al., "Intrathecal CGRP$_{8-37}$—Induced Bilateral Increase in Hindpaw Withdrawal Latency in Rats with Unilateral Inflammation," British Journal of Pharmacology, 117:43-50 (1996).

Appleyard et al., "Tyrosine Phosphorylation of the $_K$-Opioid Receptor Regulates Agonist Efficacy," The Journal of Biological Chemistry, 275:38281-38285 (2000).

Arora et al., "Mediation of Cyclic AMP Signaling by the First Intracellular Loop of the Gonadotropin-releasing Hormone Receptor," The Journal of Biological Chemistry, 273:25581-25586 (1998).

Benovic et al., "Synthetic Peptides of the Hamster β$_2$—Adrenoceptor as Substrates and Inhibitors of the β-Adrenoceptor Kinase," Br. J. Clin. Pharmoc., 30:3S-125 (1990).

Bommakanti et al., "Extensive Contact between Gi2 and N-Formyl Peptide Receptor of Human Neutrophils: Mapping of Binding Sites Using Receptor-Mimetic Peptides," Biochemistry, 34:6720-6728 (1995).

Brass, "Platelets and proteases," Nature, 413:26-27 (2001).

Calandra et al., "Dual Intracellular Signaling Pathways Mediated by the Human Cannabinoid CB$_1$, Receptor," European Journal of Pharmacology, 374:445-455 (1999).

Cassina et al., "Dual Intracellular Pathways in Gonadotropin Releasing Hormone (GNRH) Induced Desensitization of Luteinizing Hormone (LH) Secretion," Life Sciences, 64:2215-2223 (1999).

Chackalamannil, "Thrombin receptor antagonists as novel therapeutic targets," Current Opinion in Drug Discovery & Development, 4(4):417-427 (2001).

Cummings, et al., "Expression and Function of the Chemokine Receptors CXCR1 and CXCR2 in Sepsis," J. Immunol., 162:2341-2346 (1999).

Cypess et al., "Two Cytoplasmic Loops of the Glucagon Receptor are Required to Elevate cAMP or Intracellular Calcium," The Journal of Biological Chemistry, 274:19455-19464 (1999).

Damaj et al., "Identification of G-Protein Binding Sites of the Human Interleukin-8 Receptors by Functional Mapping of the Intracellular Loops," FASEB J., 10:1426-1434 (1996).

DeAlmeida et al. "Identification of Binding Domains of the Growth Hormone-Releasing Hormone Receptor by Analysis of Mutant and Chimeric Receptor Proteins," Molecular Endocrinology, 12:750-765 (1998).

Gaudin et al., "Constitutive Activation of the Human Vasoactive Intestinal Peptide 1 Receptor, a Member of the New Class II Family of G Protein-Coupled Receptors," The Journal of Biological Chemistry, 273:4990-4996 (1998).

Halford et al., "Functional Role and Sequence Analysis of a Lymphocyte Orphan Opioid Receptor," Journal of Neuroimmunology, 59:91-101 (1995).

Kilpatrick et al., "7TM Receptors: The Splicing on the Cake," Elsevier Science, 20:294-301 (1999).

Miller et al. "Insider Access: Pepducin Symposium Explores a New Approach to GBCR Modulation," Annals of the New York Academy of Sciences, 1180:E1-E12 (2009).

Moro et al., "Hydrophobic Amino Acid in the i2 Loop Plays a Key Role in Receptor-G Protein Coupling," The Journal of Biological Chemistry, 268:22273-22276 (1993).

Nabhan et al., "The Alternatively Spliced Type II Corticotropin-Releasing Factor Receptor, Stably Expressed in LLCPK-1 Cells, is Not Well Coupled to the G Protein(s), Biochemical and Biophysical Research Communications," 212:1015-1021 (1995).

Nakamura et al., "A New Type of Human Calcitonin Receptor Isoform Generated by Alternative Splicing," Biochemical and Biophysical Research Communications, 209:744-751 (1995).

Nakamura et al., "Signaling and Phosphorylation-Impaired Mutants of the Rat Follitropin Receptor Reveal an Activation- and Phosphorylation-Independent but Arrestin-Dependent Pathway for Internalization," The Journal of Biological Chemistry, 273:24346-24354 (1998).

Nakamura et al., "The Agonist-Induced Phosphorylation of the Rat Follitropin Receptor Maps to the First and Third Intracellular Loops," Molecular Endocrinology, 12:580-591 (1998).

Naro et al., "Phospholipase D- and Protein Kinase C lsoenzyme-Dependent Signal Transduction Pathways Activated by the Calcitonin Receptor," Endocrinology, 139:3241-3248(1998).

Nussenzveig et al, "Inhibition of Inositol Phosphate Second Messenger Formation by Intracellular Loop One of a Human Calcitonin Receptor," The Journal of Biological Chemistry, 269:28123-28129 (1994).

Palm et al., "Mapping of β-Adrenoceptor Coupling Domains to G$_S$-Protein by Site-Specific Synthetic Peptides," FEBS Letters, 254:89-93 (1989).

Patterson et al, "New Tricks for Old Dogs: Nonthrombotic Effects of Thrombin in Vessel Wall Biology," Circulation Research, 88:987-997 (2001).

Peluso et al., "Distribution of Nociceptin/Orphanin FQ Receptor Transcript in Human Central Nervous System and Immune Cells," Journal of Neuroimmunology, 81:184-192 (1998).

Riewald, et al. "Orchestration of Coagulation Protease Signaling by Tissue Factor," Trends Cardiovascular Med., 12:149-154 (2002).

Schipani et al., "A Constitutively Active Mutant PTH-PTHrP Receptor in Jansen-Type Metaphyseal Chondrodysplasia," Science, 268:98-100 (1995).

Schneider et al., "A C-Terminally Truncated Human Parathyroid Hormone Receptor is Functional and Activates Multiple G Proteins," FEBS Letters, 351:281-285 (1994).

Schöneberg et al., "Plasma Membrane Localization and Functional Rescue of Truncated Forms of a G Protein-Coupled Receptor," The Journal of Biological Chemistry, 270:18000-18006 (1995).

Swift et al., "Role of the PAR1 Receptor 8th Helix in Signaling," The Journal of Biological Chemistry, 281:4109-4116 (2006).

Wank, "G Protein-Coupled Receptors in Gastrointestinal Physiology. CCK Receptors: An Exemplary Family," Am. J. Physiol. 274:G607-G613 (1998).

Wu et al., "First Intracellular Loop of the Human Cholecystokinin-A Receptor is Essential for Cyclic AMP Signaling in Transfected HEK-293 Cells," The Journal of Biological Chemistry, 272:9037-9042 (1997).

Wu et al., "Single Amino Acid Substitution of Serine82 to Asparagine in First Intracellular Loop of Human Cholecystokinin (CCK)—B Receptor Confers Full Cyclic AMP Responses to CCK and Gastrin," The American Society for Pharmacology and Experimental Therapeutics, 55:795.

Adachi et al., "Functional Domains of Human Endothelin Receptor.," J. Cardiovasc. Pharmacol., 8:S121-S124(1993).

Al-Obeidi et al., "Peptide and Peptidomimetic Libraries. Molecular Diversity and Drug Design," Mol. Biotechnol., 9:205-223 (1998).

An et al., "Identification of cDNAs Encoding Two G Protein-Coupled Receptors for Lysosphingolipids," FEBS Lett., 417:279-282 (1997).

Attwood et al., "Design of a Discriminating Fingerprint for G-Protein-Coupled Receptors," Protein Engineering, 6:167-176 (1993).

Attwood et al., "Fingerprinting G-Protein-Coupled Receptors," Protein Engineering, 7:195-203 (1994).

Bischoff et al., "Lysosphingolipid Receptor-Mediated Diuresis and Natriuresis in Anaesthetized Rats," British Journal of Pharmacology, 132:1925-1933 (2001).

Bockaert et al., "Molecular Tinkering of G Protein-Coupled Receptors: An Evolutionary Success," The EMBO Journal, 18:1723-1729 (1999).

Chun et al., "A Growing Family of Receptor Genes for Lysophosphatidic Acid (LPA) and Other Lysophospholipids (LPs)," Cell Biochem. Biophys.;30:213-242 (1999).

Colombo et al., "$G_s$ Regulation of Endosome Fusion Suggests a Role for Signal Transduction Pathways in Endocytosis," The Journal of Biological Chemistry, 269:14919-14923 (1994).

Covic et al, "Pepducin-Based Intervention of Thrombin-Receptor Signaling and Systemic Platelet Activation," Nature Medicine, 8:1161-1165 (2002).

Cunningham et al., "High-Resolution Epitope Mapping of hGH-Receptor Interactions by Alanine-Scanning Mutagenesis," Science, 244:1081-1085 (1989).

Eder et al., "Constitutive and Lysophosphatidic Acid (LPA)-induced LPA Production: Role of Phospholipase D and Phospholipase $A_2^1$," Clinical Cancer Research, 6:2482-2491 (2000).

Eichler et al., "Peptide, Peptidomimetic, and Organic Synthetic Combinatorial Libraries," Med. Res. Rev., 15:481-496 (1995).

Harmar, "Family-B G-Protein-Coupled Receptors," Genome Biology, 21:1-10 (2001).

Heesen et al., "Cloning and Chromosomal Mapping of an Orphan Chemokine Receptor. Mouse RDC1," Immunogenetics, 47:364-370 (1998).

Hermanson, Bioconjugate Techniques, Book, Table of Contents and pp. 3-26 (1996).

Hogaboam et al., "The Therapeutic Potential in Targeting CCR5 and CXCR4 Receptors in Infectious and Allergic Pulmonary Disease," Pharmacology & Therapeutics, 107:314-328 (2005).

Hruby et al., "Synthesis of Oligopeptide and Peptidomimetic Libraries," Current Opinion in Chemical Biology, 1:114-119 (1997).

Jung et al., "Conformation of a β-Adrenoceptor-Derived Signal Transducing Peptide as Inferred by Circular Dichroism and $^1$H NMR Spectroscopy," Biochemistry, 35:6399-6405 (1996).

Kahn et al., "Protease-activated receptors 1 and 4 mediate activation of human platelets by thrombin," Journal of Clinical Investigation, US, 103:879-887 (1999).

Kolakowski, "GCRDb: A G-Protein-Coupled Receptor Database," Receptors and Channels, 2:1-7 (1994).

König et al., "Three Cytoplasmic Loops of Rhodopsin Interact with Transducin," Proc. Natl. Acad. Sci. USA, 86:6878-6882 (1989).

Ladoux et al., "Coordinated Up-Regulation by Hypoxia of Adrenomedullin and One of Its Putative Receptors (RDC-1) in Cells of the Rat Blood-Brain Barrier," The Journal of Biological Chemistry, 275:39914-39919 (2000).

Lang et al., "Conserved Transducer Coupling but Different Effector Linkage Upon Expression of the Myeloid fMet-Leu-Phe Receptor in Insulin Secreting Cells," The EMBO Journal, 12:2671-2679 (1993).

Leger et al., "Protease-Activated Receptors in Cardiovascular Diseases," Circulation, 114:1070-1077 (2006).

Marin et al., "The Amino Terminus of the Fourth Cytoplasmic Loop of Rhodopsin Modulates Rhodopsin-Transducin Interaction," The Journal of Biological Chemistry, 275:1930-1936 (2000).

Mechoulam et al., "A Random Walk Through a Cannabis Field," Pharmacology Biochemistry & Behavior, 40:461-464 (1991).

Moro et al., "Overlapping Multi-Site Domains of the Muscarinic Cholinergic Hm1 Receptor Involved in Signal Transduction and Sequestration," The Journal of Biological Chemistry, 269:6651-6655 (1994).

O'Dowd et al., "Palmitoylation of the Human $β_2$-Adrenergic Receptor," The Journal of Biological Chemistry, 264:7564-7569 (1989).

Postma et al., "Sphingosine-1-Phosphate Rapidly Induces Rho-Dependent Neurite Retraction: Action Through a Specific Cell Surface Receptor," The EMBO Journal, 15:2388-2395 (1996).

Probst et al., "Sequence Alignment of the G-Protein Coupled Receptor Superfamily," DNA and Cell Biology, 11:1-20 (1992).

Prossnitz et al., "The N-Formyl Peptide Receptor: A Model for the Study of Chemoattractant Receptor Structure and Function," Pharmacol. Ther., 74:73-102 (1997).

Qian et al., "Evidence for the Involvement of Several Intracellular Domains in the Coupling of Oxytocin Receptor to $Gαq/11$," Cell. Signal., 10:101-105 (1998).

Reggio, "Ligand-Ligand and Ligand-Receptor Approaches to Modeling the Cannabinoid CB1 and CB2 Receptors: Achievements and Challenges," Curr. Med. Chem., 6:665-683 (1999).

Ripka et al., "Peptidomimetic Design," Current Opinion in Chemical Biology 2:441-452 (1998).

Robbins et al., "Myristoylation and Differential Palmitoylation of the HCK Protein-Tyrosine Kinases Govern Their Attachment to Membranes and Association with Caveolae," Molecular Cellular Biology, 15:3507-3515 (1995).

Seitz et al, "Synthetic Peptide Conjugates—Tailor-Made Probes for the Biology of Protein Modification and Protein Processing," Tetrahedron, 57:2247-2277 (2001).

Sharpe, "Cannabis: Time for Scientific Evaluation of This Ancient Remedy?," Anesth. Analg., 90:237-240 (2000).

Shimizu et al., "A Putative G Protein-Coupled Receptor, RDC1, Is a Novel Coreceptor for Human and Simian Immunodeficiency Viruses," Journal of Virology, 74:619-626 (2000).

Stephens et al., "A Sequence within the Cytoplasic Tail of GpIIb Independently Activates Platelet Aggregation and Thromboxane Synthesis," The Journal of Biological Chemistry, 273:20317-20322 (1998).

Takuwa et al., "Subtype-Specific, Differential Activities of the EDG Family Receptors for Sphingosine-1-Phospate, A Novel Lysophospholipid Mediator," Molecular and Cellular Endocrinology, 177:3-11 (2001).

Taylor et al., "Coupling an α2-Adrenergic Receptor Peptide to G-Protein: A New Photolabeling Agent," Peptides, 15:829-834 (1994).

Thomas et al., "Molecular Cloning of the fMet-Leu-Phe Receptor from Neutrophils," The Journal of Biological Chemistry, 265:20061-20064 (1990).

Trejo et al, "Protease-Activated Receptors: New Concepts in Regulation of G Protein-Coupled Receptor Signaling and Trafficking," The Journal of Pharmacology and Experimental Therapeutics, 307:437-442 (2003).

Wong et al., "Chimeric Muscarinic Cholinergic:β-Adrenergic Receptors That are Functionally Promiscuous Among G Proteins," The Journal of Biological Chemistry, 269:18968-18976 (1994).

Wu et al., "Single Amino Acid Substitution of Serine82 to Asparagine in First Intracellular Loop of Human Cholecystokinin (CCK)—B Receptor Confers Full Cyclic AMP Responses to CCK and Gastrin," The American Society for Pharmacology and Experimental Therapeutics, 55:795, 1999.

* cited by examiner

| SEQ ID NO. | | |
|---|---|---|
| 1 | CXCR1_HUMAN | KYVVIIAYALVFLLSLLGNSLVMLVILYSRVGRSVTDVYLLNLALADLLFALTLPIWAASK |
| 2 | CXCR1_PANTR | KYVVIITYALVFLLSLLGNSLVMLVILYSRVGRSVTDVYLLNLALADLLFALFALTLPIWAASK |
| 3 | CXCR1_GORGO | KYVVIIITYALAFLAFLLSLLGNSLVMLVILYSRGGRSVTDVYLLNLALADLFALTLPIWAASK |
| 4 | CXCR1_RABIT | KYVVVVIYALVFLLSLLGNSLVMLVILYSRSNRSVTDVYLLNLAMADLLFALTMPIWAVSK |
| 5 | CXCR1_RAT | RQAVVVFYALVFLLSLLGNSLVMLVILYRRRTRSVTDVYVYLLNLAIADLLFSLTLPFLAVSK |
| 6 | CXCR2_HUMAN | KYFVVIIYALVFLLSLLGNSLVMLVILYSRVGRSVTDVYLLNLALADLLFALTLPIWAASK |
| 7 | CXCR2_MOUSE | SYAVVVIYVLVTLLSLVGNSLVMLVILVILYNRSTCSVTDVYLLNLAIADLFFALTLPVWAASK |
| 8 | CXCR2_PANTR | KYFVVIIYALVFLLSLLGNSLVMLVILYSRVGRSVTDVYLLNLALADLLFALTLPIWAASK |
| 9 | CXCR2_MACMU | KYFVVIIYALVFLLSLLGNSLVMLVILYSRVGRSVTDVYLLNLALADLLFALTLPIWAASK |
| 10 | CXCR2_GORGO | KYFVVIIYALVFLLSLLGNSLVILVILYSRVGRSVTCSVTDVYLLNLALADLLFALTLPIWAASK |
| 11 | CXCR2_RABIT | SYVVLITYILVFLLSLLGNSLVMLVILYSRSTCSVTDVYLLNLALADLLFATTLPIWAASK |
| 12 | CXCR2_CANFA | KYAVVVIYLVLVFVLNLLGNSLVMLVILYSRVSHSVTDVYLLNLAIADLLFALTLPIWAVSK |
| 13 | CXCR2_BOVIN | KYAVVVIDALVFLLSLLGNSLVMLVILYSRIGRSVTDVYLLNLAMADLLFAMTLPIWTASK |
| 14 | CXCR2_RAT | RYAVVVIYLVLVTLLSLVGNSLVMLVILYNRSTCSVTDVYLLNLAIADLFFALTLPVWAASK |

FIG. 2

Classical chemokine receptors

| Receptor | Ligand | Cell type |
|---|---|---|
| CCR1 | RANTES, MPIF-1, HCC-1, MIP-1α, MIP-1β, MCP-3, | Lymphocytes, monocytes, eosinophils, dendritic cells, macrophages |
| CCR2 | MCP-1, MCP-2, MCP-3, MCP-4 | Monocytes, eosinophils, dendritic cells, macrophages, lymphocytes |
| CCR3 | Eot, Eot-2, MIP-1δ, RANTES, MCP-2, MCP-3, MCP-4 | Monocytes, eosinophils, dendritic cells, macrophages, lymphocytes |
| CCR4 | TARC, MDC | lymphocytes |
| CCR5 | MIP-1α, MIP-1β, RANTES, MCP-2, | Monocytes, lymphocytes, macrophages, dendritic cells, eosinophils |
| CCR6 | MIP-3α | Monocytes, lymphocytes, macrophages, dendritic cells |
| CCR7 | 6Ckine, MIP-3β | Dendritic cells, lymphocytes, eosinophils |
| CCR8 | I-309, TARC | lymphocytes |
| CCR9 | TECK | lymphocytes |
| CXCR1 | IL-8, GCP-2, | Neutrophils, eosinophils, lymphocytes, macrophages, dendritic cells |
| CXCR2 | IL-8, GCP-2, ENA-78, NAP-2, Gro | Neutrophils, eosinophils, lymphocytes, macrophages, dendritic cells |
| CXCR3 | MIG | Neutrophils, eosinophils, lymphocytes, macrophages, dendritic cells |
| CXCR4 | SDF-1 | Neutrophils, dendritic cells, macrophages, lymphocytes, monocytes |
| CXCR5 | BLC/BCA-1 | lymphocytes |
| CXCR6 | 6Ckine | Lymphocytes, NK-cells |
| CX3CR1 | fractalkine | Neutrophils, NK-cells |

FIG. 3

Atypical chemokine receptors

| Receptor | Ligand | Cell type |
|---|---|---|
| NK1 | Substance P, neurokinin A, neurokinin B | Lymphocytes, monocytes, eosinophils, dendritic cells, macrophages |
| NK2 | Neurokinin A, neurokinin B, substance P | Monocytes, eosinophils, dendritic cells, macrophages, lymphocytes |
| MLT 2 | melatonin | Monocytes, neutrophils |
| GRP/bombesin receptor | bombesin | Lymphocytes, dendritic cells, monocytes |
| FPR1 | fMLP | Neutrophils, monocytes, macrophages, dendritic cells, eosinophils |
| FPRL-1 | fMLP, SAA, β-amyloid, | Neutrophils, monocytes, macrophages, dendritic cells, eosinophils |
| C3aR | C3a | lymphocytes |
| C5aR | C5a | Lymphocytes, neutrophils |
| EDG 1-7 | Sphingosine-1-phosphate | Monocytes, eosinophils, dendritic cells, macrophages, lymphocytes |

FIG. 4

| SEQ ID NO. | | 110 | 120 | 130 | 140 |
|---|---|---|---|---|---|
| 36 | CXCR4_HUMAN | NKIFLPTIYSIIFLTGIVGNGLVILVIMGYQKKLRSMTDKYRLHLSVADLLFVITLPFWAVD |
| 37 | CXCR4_MOUSE | NRIFLPTIYFIIFLTGIVGNGLVILVMGYQKKLRSMTDKYRLHLSVADLLFVITLPFWAVD |
| 38 | CXCR4_PAPAN | NRIFLPTIYSIIFLTGIVGNGLVILVMGYQKKLRSMTDKYRLHLSVADLLFVITLPFWAVD |
| 39 | CXCR4_MACMU | NRIFLPTIYSIIFLTGIVGNGLVILVMGYQKKLRSMTDKYRLHLSVADLLFVITLPFWAVD |
| 40 | CXCR4_PANTR | NKIFLPTIYSIIFLTGIVGNGLVILVMGYQKKLRSMTDKYRLHLSVADLLFVITLPFWAVD |
| 41 | CXCR4_FELCA | NRIFLPTVYSIIFLTGIVGNGLVILVMGYQKKLRSMTDKYRLHLSVADLLFVITLPFWAVD |
| 42 | CXCR4_BOVIN | NRIFLPTVYSIIFLTGIVGNGLVILVMGYQKKLRSMTDKYRLHLSVADLLFVLTLPFWAVD |
| 43 | CXCR4_RAT | NRIFLPTIYFIIFLTGIVGNGLVILVMGYQKKLRSMTDKYRLHLSVADLLFVITLPFWAVD |

FIG. 14

| SEQ ID NO. | | 120 130 140 |
|---|---|---|
| 44 | CCR1_HUMAN | PPLYSLVFVIGLVGNILVVLVLVQYKRLKNMTSIYLLNLAISDLLFLTLP |
| 45 | CCR1_MOUSE | PPLYSLVFIIGVVGNVLMILVLMQHRRLQSMTSIYLFNLAVSDLVFLFTLP |
| 46 | CCR1_MACMU | PPLYSLVFVIGVVGNLLVVLVLVQYKRLKNMTNIYLLNLAISDLLFLFLTLP |

FIG. 15

| SEQ ID NO. | | 120 130 140 |
|---|---|---|
| 47 | CCR2_HUMAN | PPLYSLVFIFGFVGNMLVVLILINCKKLKCCLTDIYLLNLAISDLLFLITLPLWAHSAANE |
| 48 | CCR2_MOUSE | PPLYSLVFIFGFVGNMLVVIILIGCKKLKCCLTDIYLLNLAISDLLFLLTLPFWAHYAANE |
| 49 | CCR2_RAT | PPLYSLVFIFGFVGNMLVIILISCKKLKSMTDIYLLNLAISDLLFLLTLPFWAHYAANE |
| 50 | CCR2_MACMU | PPLYSLVFIFGFVGNMLVVLILINCKKLKSLTDIYLLNLAISDLLFLITLPLWAHSAANE |

FIG. 16

```
                    TM1                    i1              TM2
           120    130    140
           |      |      |
SEQ ID NO. CCR4_HUMAN  PPLYSLVFGLLGNSVVVLVLFKYKRLRSMTDVYLLNLAISDLLFVFSLPFWG
       51  CCR4_MOUSE  PPLYSLVFLLGLFGNSVVVLVLFKYKRLKSMTDVYLLNLAISDLLFVLSLPFWG
       52
                         1.50                 2.50
```

FIG. 17

| SEQ ID NO. | | 120 | 130 | 140 | |
|---|---|---|---|---|---|
| 53 | CCR5_HUMAN | PPLYSLVFIFGFVGNMLVILILINCKRLKSMTDIYLLNLAISDLFFL |
| 54 | CCR5_MOUSE | PPLYSLVFIFGFVGNMMVFLILISCKKLKSVTDIYLLNLAISDLLFL |
| 55 | CCR5_PAPHA | PPLYSLVFIFGFVGNILVVLILINCKRLKSMTDIYLLNLAISDLLFL |
| 56 | CCR5_LOPAT | PPLYSLVFIFGFVGNILVVLILINCKRLKSMTDIYLLNLAISDLLFL |
| 57 | CCR5_MACMU | PPLYSLVFIFGFVGNILVVLILINCKRLKSMTDIYLLNLAISDLLFL |
| 58 | CCR5_MACNE | PPLYSLVFIFGFVGNILVVLILINCKRLKSMTDIYLLNLAISDLLFL |
| 59 | CCR5_MACFA | PPLYSLVFIFGFVGNILVVLILINCKRLKSMTDIYLLNLAISDLLFL |
| 60 | CCR5_PANTR | PPLYSLVFIFGFVGNMLVILILINCKRLKSMTDIYLLNLAISDLFFL |
| 61 | CCR5_GORGO | PPLYSLVFIFGFVGNMLVILILINCKRLKSMTDIYLLNLAISDLFFL |
| 62 | CCR5_RAT | PPLYSLVFIFGFVGNMMVFLILISCKKLKSMTDIYLFNLAISDLLFL |

| SEQ ID NO. | PAR1-4 | | | |
|---|---|---|---|---|
| | | 110 | 120 | 130 | 140 |
| 63 | PAR1_HUMAN | FVPSVYTGVFVVSLPLNIMAIVVFILKMKVKKPAVVYMLHLATADVLFVSVLPFK |
| 64 | PAR1_MOUSE | FMPSVYTIVFIVSLPLNVLAIAVFVLRMKVKKPAVVYMLHLAMADVLFVSVLPFK |
| 65 | PAR1_RAT | FIPSVYTFVFIVSLPLNILAIAVFVLRMKVKKPAVVYMLHLAMADVLFVSVLPFK |
| 66 | PAR1_CRILO | FIPSVYTEVFVVSLPLNILAIAVFVLKMKVKKPAVVYMLHLAMADVLFVSVLPLK |
| 67 | PAR1_PAPHA | FVPSVYTGVFVVSLPVNIMAIVVFILKMKVKKPAVVYMLHLATADVLFVSVLPFK |
| 68 | PAR1_XENLA | FVPSLYTVFFIVGLPLNLLAIIIFLFKMKVRKPAVVYMLNLAIADVFFVSVLPFK |
| 69 | PAR2_HUMAN | FLPIVYTIVFVVGLPSNGMALWVFLFRTKKKHPAVIYMANLALADLLSVIWFPLK |
| 70 | PAR2_MOUSE | FLPVIYIIVFVIGLPSNGMALWIFLFRTKKKHPAVIYMANLALADLLSVIWFPLK |
| 71 | PAR2_RAT | FLPVIYIIVFVIGLPSNGMALWVFFFRTKKKHPAVIYMANLALADLLSVIWFPLK |
| 72 | PAR3_HUMAN | LIPAIYLLVFVVGVPANAVTLWMLFFRTRSICTTV.FYTNLAIADFLFCVTLPFK |
| 73 | PAR3_MOUSE | VIPAIYILLFVVGVPSNIVTLWKLSLRTKSISL.VIFHTNLAIADLLFCVTLPFK |
| 74 | PAR3_RAT | VIPAIYILVFVIGVPANIVTLWKLSSRTKSICL.VIFHTNLAIADLLFCVTLPFK |
| 75 | PAR4_HUMAN | LVPALYGLVLVVGLPANGLAIWVLATQAPRL.PSTMLLMNLATADLLLALALPPR |
| 76 | PAR4_MOUSE | LVPALYGLIVVAVGLPANGLAIWVLATRVPRL.PSTILLTNLAVADSLLALVPPPR |
| 77 | PAR4_RAT | LVPAIYGLVVVGLPANGLAIWVLATRVPRL.PSTILLMNLAVADLLLALVLPPR |

| SEQ ID NO. | | 120 130 | | |
|---|---|---|---|---|
| 100 | NK1R_HUMAN | WQIVLWAAAYTVIVVTSVV | GNVVVMWIILA | HKRMRTVTNYFLVNLAFAEAS |
| 101 | NK1R_MOUSE | WQIVLWAAAYTVIVVTSVV | GNVVVIWIILA | HKRMRTVTNYFLVNLAFAEAC |
| 102 | NK1R_RAT | WQIVLWAAAYTVIVVTSVV | GNVVVIWIILA | HKRMRTVTNYFLVNLAFAEAC |
| 103 | NK1R_CAVPO | WQIVLWAAAYTVIVVTSVV | GNVVVMWIILA | HKRMRTVTNYFLVNLAFAEAS |
| 104 | NK1R_RANCA | WQIALMSVAYSIIVIVSLV | GNIIVMWIITA | HKRMRTVTNYFLVNLAFAEAS |

G PROTEIN COUPLED RECEPTOR AGONISTS AND ANTAGONISTS AND METHODS OF USE

REFERENCE TO RELATED APPLICATIONS

This application claims benefit under 35 U.S.C. §371 to PCT Application No. PCT/US2005/039959, filed on Nov. 4, 2005, which claims priority to U.S. Provisional Patent Application Ser. No. 60/625,706, filed on Nov. 4, 2004, which is incorporated herein by reference.

STATEMENT AS TO FEDERALLY SPONSORED RESEARCH

This invention was made with Government support under Grant Numbers R01 HL064701, R01 HL057905 and R01 CA104406 awarded by the National Institutes of Health. The Government has certain rights in the invention.

FIELD OF THE INVENTION

The invention relates generally to G protein coupled receptors (GPCRs) and in particular to GPCR agonists and antagonists, use of these compounds and their pharmaceutical compositions, e.g., in the treatment, modulation and/or prevention of physiological conditions associated with GPCRS, such as in treating conditions in which chemokine receptors play a role, e.g., sepsis, arthritis, inflammation and autoimmune diseases.

BACKGROUND OF THE INVENTION

A variety of hormones, neurotraismitters and biologically active substances control, regulate, or adjust the functions of living bodies via specific receptors located in cell membranes. Many of these receptors mediate the transmission of intracellular signals by: activating guanine nucleotide-binding proteins (G proteins) to which the receptor is coupled. Such receptors are generically referred to as G protein coupled receptors ("GPCRs"). Binding of a specific signaling molecule to the GPCR can cause a conformational change in the receptor, resulting in a form that is able to bind and activate a G protein, thereby triggering a cascade of intracellular events that eventually leads to a biological response. Typically, GPCRs interact with G proteins to regulate the synthesis of intracellular second messengers such as cyclic AMP, inositol phosphates, diacylglycerol and calcium ions.

Chemokines are leukocyte attractants and contribute to immune processes that involve leukocyte migration. Leukocyte trafficking is highly coordinated, and a breakdown of the underlying control mechanisms might contribute to exaggerated innate immune activations, such as systemic inflammatory response syndromes or autoimmune diseases. Chemokine-induced signaling is mediated by GPCRs, and by definition their hallmark is leukocyte chemoattraction. In addition, chemokines induce cellular responses that are unrelated to leukocyte migration, like cell survival, virus-host interactions, tumor growth and metastasis, organogenesis, and angiogenesis.

GPCRs play a vital role in the signaling processes that control cellular metabolism, cell growth and motility, adhesion, inflammation, neuronal signaling, and blood coagulation. GPCR proteins also have a very important role as targets for a variety of signaling molecules which control, regulate, or adjust the functions of living bodies. GPCRs are involved in a wide variety of disorders, as is well-known in the art. The development of new GPCR modulators, e.g., agonists, partial agonists, inverse agonists and antagonists, may have therapeutic applications for treating GPCR-related disorders, including sepsis, arthritis, inflammation and autoimmune diseases.

SUMMARY OF THE INVENTION

The present invention is based on the discovery of modified peptides called pepducins which comprise a cell-penetrating or membrane-tethering moiety to attached to a peptide derived from the first intracellular loop structure of a GPCR. Pepducins may be considered chimeric peptides/polypeptides, and are agonists and/or antagonists of receptor-G protein signaling. These compositions exhibit selectivity for their cognate receptor.

Accordingly, the invention provides a pepducin composition, a chimeric polypeptide including a first domain of a first intracellular loop (i1 loop) or a fragment thereof of a GPCR and a second domain, attached to the first domain. The second domain is a naturally or non-naturally occurring cell-penetrating and/or membrane-tethering hydrophobic moiety. The first domain preferably does not include a native extracellular portion of the GPCR. The pepducins of the invention desirably bind to the cognate GPCR from which the first domain is derived.

The first domain (the first intracellular loop (i1 loop) or a fragment thereof of a G protein coupled receptor (GPCR)) includes an amino acid sequence of a luteinizing hormone receptor; a follicle stimulating hormone receptor; a thyroid stimulating hormone receptor; a calcitonin receptor; a glucagon receptor; a glucagon-like peptide 1 receptor (GLP-1); a metabotropic glutamate receptor; a parathyroid hormone receptor; a vasoactive intestinal peptide receptor; a secretin receptor; a growth hormone releasing factor (GRF) receptor; protease-activated receptors (PARs); cholecystokinin receptors; somatostatin receptors; melanocortin receptors; ADP receptors; adenosine receptors; thromboxane receptors; platelet activating factor receptor; adrenergic receptors; 5-HT receptors; chemokine receptors; neuropeptide receptors; opioid receptors; parathyroid hormone (PTH) receptor; or a vasoactive intestinal peptide (VIP) receptor.

For example, the first domain (the first intracellular loop (i1 loop) or a fragment thereof of a G protein coupled receptor (GPCR)) contains an amino acid sequence of a protease-activated receptor (PAR) or a chemokine receptor. The protease-activated receptor may be, e.g., PAR1, PAR2, PAR3, or PAR4. A chemokine receptor may be a CC or CXC receptor such as CCR1, CCR2, CCR3, CCR4, CCR5, CCR6, CCR7, CCR8 or CCR9; or CXCR1, CXCR2, CXCR3, CXCR4, CXCR5, CXCR6 or CX3CR1; respectively. In another embodiment the first domain (the first intracellular loop (i1 loop) or a fragment thereof of a G protein coupled receptor (GPCR)) may be, e.g., from cholecystokinins A and B (CCKA, CCKB); somatostatin-2 (SSTR2); melanocortin-4 (MC4R); glucagon-like peptide-1 receptor (GLP-1R); $P2Y_{12}$ ADP receptor; or from "atypical" chemokine receptors such as NK1, NK2, GRP/bombesin receptors, FPR1, FPRL-1, C3aR or C5aR. In a particular embodiment, pepducins of the invention include those for PAR2, CXCR1, CXCR2, CXCR4 and CCR5 chemokine receptors.

The second domain (the cell-penetrating and/or membrane-tethering hydrophobic moiety) is attached at the N-terminal end, the C-terminal end, an amino acid between the C-terminal amino acid and the N-terminal amino acid, or both the N-terminal and C-terminal ends of the first domain. Desirably, the cell-penetrating and/or membrane-tethering hydrophobic moiety is a lipid such as a straight chain fatty acid, e.g., nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and a lignoceroyl ($C_{24}$) moiety. The cell-penetrating and/or membrane-tethering hydrophobic moiety may be attached to the chimeric polypeptide with, e.g., amide bonds, sulfhydryls, amines, alcohols, phenolic groups, or carbon-carbon bonds. Particular embodiments include palmitoyl or lithocholic acid (or salts thereof) as the hydrophobic moiety. Other cell-penetrating and/or membrane-tethering hydrophobic moieties include cholesterol, phospholipids, steroids, sphingosine, ceramide, octyl-glycine, 2-cyclohexylalanine, benzoylphenylalanine, $C_1$ or $C_2$ acyl groups, or $C_3$-$C_8$ fatty acids.

The invention further relates to pharmaceutical compositions comprising the pepducin compositions of the invention and a pharmaceutically acceptable carrier, and to kits including, in one or more containers, these pharmaceutical compositions.

The invention includes methods of treating, reducing the severity of, or preventing sepsis, e.g., in a mammalian subject by administering a pepducin including a first domain of a first intracellular loop (i1 loop) or a fragment thereof of a G protein coupled receptor (GPCR) and a second domain, attached to the first domain. The second domain is a naturally or non-naturally occurring cell-penetrating, membrane-tethering hydrophobic moiety. The subject has been diagnosed with or is at risk of developing sepsis.

The compositions are also used to treat, reduce the severity of, or prevent inflammation and/or angiogenesis. Methods of treating or preventing inflammation and/or angiogenesis are carried out by administering a chemokine-inhibiting pepducin including a chimeric polypeptide comprising a first domain of a first intracellular loop (i1 loop) or a fragment thereof of a G protein coupled receptor (GPCR) and a second domain, attached to the first domain, in which the second domain is a naturally or non-naturally occurring cell-penetrating, membrane-tethering hydrophobic moiety.

The compositions are also used to treat or reduce the severity of cancer. Methods of treating or reducing the severity of cancer are carried out by administering a pepducin including a chimeric polypeptide comprising a first domain of a first intracellular loop (i1 loop) or a fragment thereof of a G protein coupled receptor (GPCR) and a second domain, attached to the first domain, in which the second domain is a naturally or non-naturally occurring cell-penetrating, membrane-tethering hydrophobic moiety.

The compositions are also used to treat or reduce the severity of thrombosis, e.g., coronary, arterial and venous (such as deep vein or mesenteric) thrombosis. Methods of treating or preventing thrombosis are carried out by administering a pepducin including a chimeric polypeptide comprising a first domain of a first intracellular loop (i1 loop) or a fragment thereof of a G protein coupled receptor (GPCR) and a second domain, attached to the first domain, in which the second domain is a naturally or non-naturally occurring cell-penetrating, membrane-tethering hydrophobic moiety.

The invention also relates to methods of treating or preventing an inflammatory disorder, wherein pepducin comprising a first domain of a first intracellular loop (i1 loop) or a fragment thereof of a G protein coupled-receptor (GPCR) and a second domain, attached to the first domain, wherein the second domain is a naturally or non-naturally occurring cell-penetrating, membrane-tethering hydrophobic moiety, is administered to a subject in need thereof. Suitable inflammatory disorders for treatment may include Chronic Obstructive Pulmonary Disease (COPD), alkylosing spondylitis, cervical arthritis, fibromyalgia, ischemia reperfusion injury, gut ischemia, juvenile rheumatoid arthritis, lumbosacral arthritis osteoarthritis, osteoporosis, psoriatic arthritis, rheumatic disease, rheumatoid arthritis, eczema, psoriasis, dermatitis, uveitis and conjunctivitis, asthma and bronchitis, ulcers, gingivitis, Crohn's disease, atrophic gastritis, gastritis varialoforme, ulcerative colitis, celiac disease, regional ileitis, peptic ulceration, pyresis, bladder irritation and cystitis, inflammatory neurological disorders of the central or peripheral nervous system, multiple sclerosis, inflammatory neuropathies and neurological complication of AIDS, autoimmune inflammation, or surgical trauma. The compositions described herein prevent, reverse or reduce the severity of sepsis and associated pathologies such as disseminated intravascular coagulation (DIC), fibrinolysis, and/or systemic inflammatory responses (SIRS).

The pepducin compositions of the invention are useful to activate or inhibit the activity of a broad range of GPCRs. Pepducins in accordance with the invention include those that act on chemokine CXC receptors, including CXCR1, CXCR2, CXCR3, CXCR4, CXCR5, CXCR6 and CX3CR1; chemokine CC receptors, including CCR1, CCR2, CCR3, CCR4, CCR5, CCR6, CCR7, CCR8 and CCR9; protease-activated receptors (PARs), e.g., PAR1, PAR2, PAR4; cholecystokinins A and B receptors (CCKA, CCKB), somatostatin-2 (SSTR2) receptor, melanocortin-4 (MC4R) receptor, glucagon-like peptide-1 receptor (GLP-1R), Sphingosine 1-phosphate (S1P) receptors, e.g., subtypes S1P1 and S1P3, EDG receptors, endothelin (ET) receptors, e.g., subtypes ET-1, ET-2, ET-3, ETA, ETB, EDG receptors, e.g., subtypes EDG-1, EDG-2, EDG-3, EDG-4, EDG-5, EDG-6, and $P2Y_{12}$ ADP receptor. Also, pepducins for "atypical" chemokine receptors such as NK1, NK2, GRP/bombesin receptors, FPR1, FPRL-1, C3aR and C5aR are within the scope of the invention. In a particular embodiment, pepducins of the invention include those for PAR2, CXCR1, CXCR2, CXCR4 and CCR5 chemokine receptors.

Administration is preferably carried out systemically such as intravenously, e.g., in cases of systemic inflammation, COPD and/or sepsis. Alternatively, the compositions are delivered subcutaneously, orally, intranasally (e.g., to treat asthma) or locally, e.g., in the form of an adhesive patch, or a cream, foam, ointment (e.g., for the alleviation of symptoms of dermatitis, psoriasis or other dermal inflammatory conditions.

BRIEF DESCRIPTION OF THE DRAWINGS

FIG. 2 is a diagram showing CXCR1 and CXCR2 i1 loop sequence including transmembrane flanking portions, which are aligned to illustrate the similarity in structure.

FIG. 3 is a chart showing chemokine receptors which pepducins in accordance with the invention may act on, their respective ligands, and the respective cell types in which the receptors may be found.

FIG. 4 is a chart showing additional chemokine receptors which pepducins in accordance with the invention may act on, their respective ligands, and the respective cell types in which the receptors may be found.

FIGS. 7A and 7B are bar graphs and FIG. 7C are photomicrographs.

FIG. 14 is a diagram showing CXCR4 i1-loop sequences including transmembrane flanking portions, which may be used in pepducins according to the invention.

FIG. 15 is a diagram showing CCR1 i1-loop sequences including transmembrane flanking portions, which may be used in pepducins according to the invention.

FIG. 16 is a diagram showing CCR2 i1-loop sequences including transmembrane flanking portions, which may be used in pepducins according to the invention.

FIG. 17 is a diagram showing CCR4 i1-loop sequences including transmembrane flanking portions, which may be used in pepducins according to the invention.

FIG. 18 is a diagram showing CCR5 i1-loop sequences including transmembrane flanking portions, which may be used in pepducins according to the invention.

FIG. 19 is a diagram showing PAR1 i1-loop sequences including transmembrane flanking portions, which may be used in pepducins according to the invention.

Figure 20:
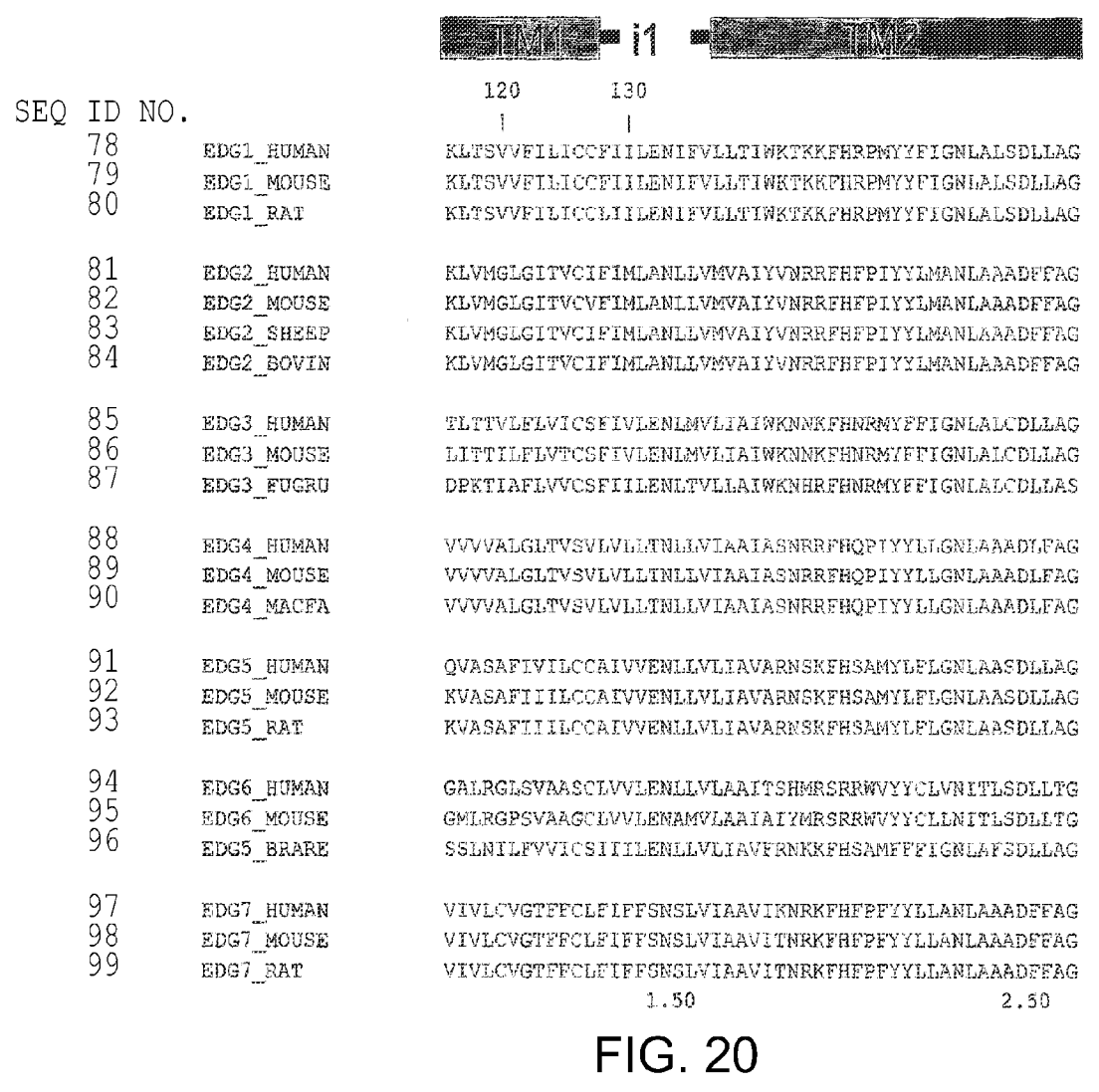

FIG. 20 is a diagram showing EDG i1-loop sequences including transmembrane flanking portions, which may be used in pepducins according to the invention.

FIG. 21 is a diagram showing NK1-R i1-loop sequences including transmembrane flanking portions, which may be used in pepducins according to the invention.

DETAILED DESCRIPTION OF THE INVENTION

Definitions

Figure 1:
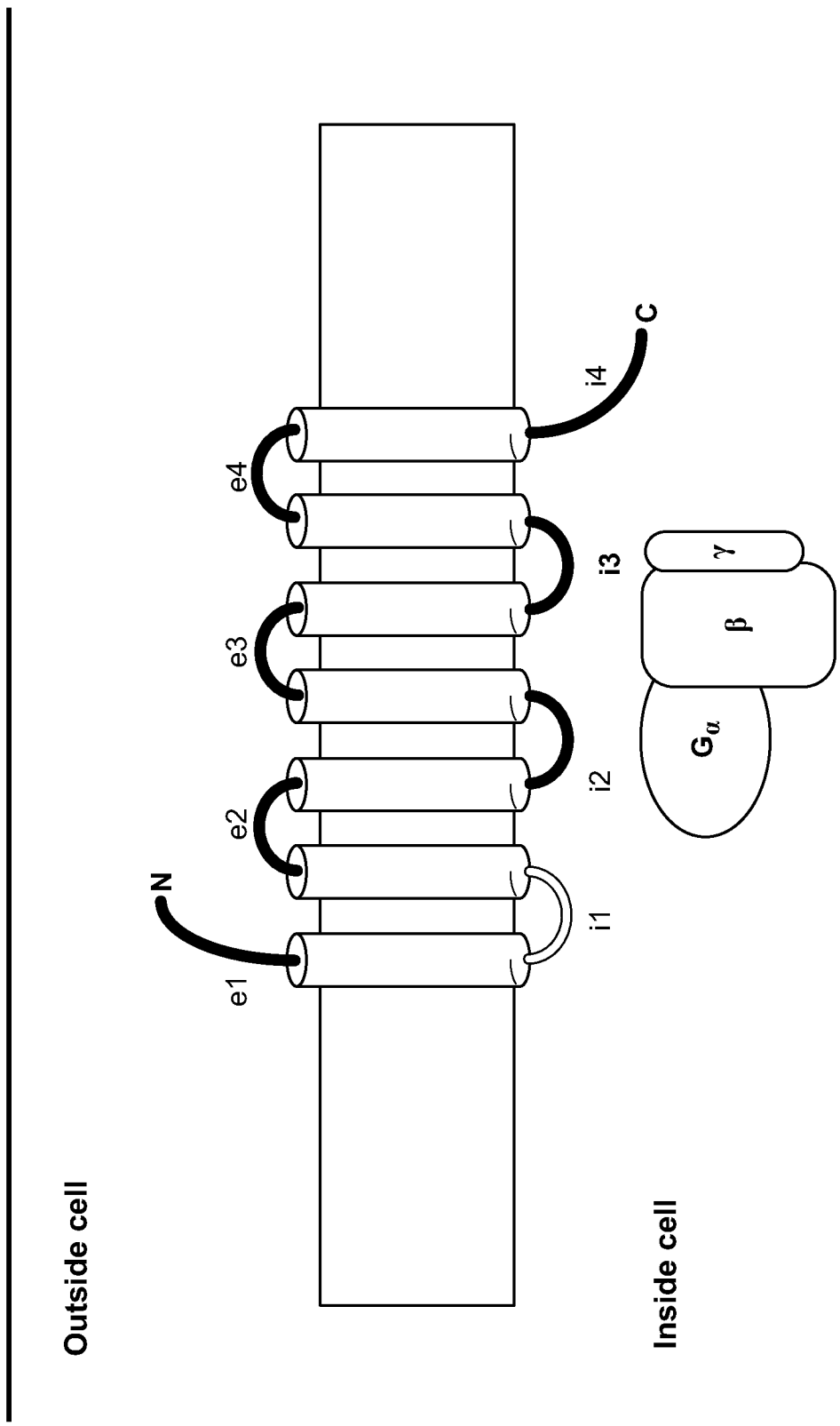
FIG. 1 is a diagram showing GPCR topology. The i1 loop is illustrated in this figure.

For convenience, certain terms used in the specification, examples, and appended claims are collected here.

"Treating", includes any effect, e.g., lessening, reducing, modulating, or eliminating, that results in the improvement of the condition, disease, disorder, etc. or symptom thereof.

"GPCR fragment" includes peptides having a portion of the sequence of a GPCR protein which is less than the entire naturally-occurring amino acid sequence of the GPCR. "Isolated GPCR fragment" includes peptides having a portion of the GPCR protein sequence which is less than the entire sequence, and not containing the naturally-occurring flanking regions. Isolated GPCR fragments lack one or more amino acids which immediately flank the reference fragment in the naturally-occurring molecule.

"Isolated intracellular GPCR fragment" includes peptides having an amino acid sequence of the intracellular i1 loop of a GPCR protein, and not containing a sequence from an extracellular loop or a transmembrane helix sequence flanking the intracellular i1 loop. "Isolated extracellular GPCR fragment" includes peptides having an amino acid sequence of an extracellular loop of a GPCR protein and not containing an amino acid of an intracellular loop or transmembrane sequence flanking regions of the extracellular loop.

"Linked" means attached. For example, a peptide and a cell-penetrating or membrane-tethering moiety are attached to each other in a pepducin via a linkage, i.e., a covalent bond. Preferably, the linkage is a labile bond such as a thiol or ester linkage. Pepducin compounds having a labile linkage are advantageous since accumulation in body tissues is lower compared to compounds with a non-labile linkage. Reduced accumulation in bodily tissues following administration to a subject is associated with decreased adverse side effects in the subject.

A "GPCR agonist" includes compositions that activate a GPCR to mimic the action of the endogenous signaling molecule specific to that receptor. A "GPCR antagonist" includes compositions that inhibit GPCR activity. GPCR activity is measured by ability to bind to an effector signaling molecule such as G-protein. An "activated GPCR" is one which is capable of interacting with and activating a G-protein. An inhibited receptor has a reduced ability to bind extracellular ligand and/or productively interact with, and activate a G-protein.

"Cell-penetrating moieties" include compounds or functional groups which mediate transfer of a substance from an extracellular space to an intracellular compartment of a cell. Cell-penetrating moieties shuttle a linked substance (e.g., a GPCR peptide or fragment of the invention) into the cytoplasm or to the cytoplasmic space of the cell membrane. For example, a cell penetrating moiety is a hydrophobic moiety. The hydrophobic moiety is, e.g., a mixed sequence peptide or a homopolymer peptide such as polyleucine or polyarginine at least about 11 amino acids long. The substance may be a peptide such as a GPCR fragment or peptidomimetic of the invention. The cell penetrating moiety may include at least 10 contiguous amino acids, e.g., 1-15 amino acids of a GPCR transmembrane helix domain.

"Membrane-tethering moieties" include compounds or functional groups which associate with or bind to a cell membrane. Thus, the membrane-tethering moiety brings the substance to which the membrane-tethering moiety is attached (i.e., the GPCR fragment or peptidomimetic of the invention) in close proximity to the membrane of a target cell. The cell membrane is eukaryotic or prokaryotic. The membrane-tethering moiety is desirably a hydrophobic moiety. The hydrophobic moiety can include a mixed sequence peptide or a homopolymer peptide such as polyleucine or polyarginine less than 10 amino acids long. The membrane-tethering moiety can include at least one to seven contiguous amino acids of a GPCR transmembrane helix domain. Preferably, the membrane-tethering moiety is at least 10 contiguous amino acids (but less than 16 amino acids) of a GPCR transmembrane domain; more preferably, the membrane-tethering moiety is at least 15 contiguous amino acids of a GPCR transmembrane domain. Membrane-tethering moieties also include cholesterol, phospholipids, steroids, sphingosine, ceramide, octyl-glycine, 2-cyclohexylalanine, or benzolylphenylalanine. Other membrane-tethering moieties include $C_1$ or $C_2$ acyl groups, or a $C_3$-$C_8$ fatty acid moiety such as propionoyl ($C_3$); butanoyl ($C_4$); pentanoyl ($C_5$); caproyl ($C_6$); heptanoyl ($C_7$); and capryloyl ($C_9$). The membrane-tethering moiety may be attached to the C-terminal amino acid, the N-terminal amino acid, or to an amino acid between the N-terminal and C-terminal amino acid of the GPCR fragment in the pepducin.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

"Small molecules" include compositions having a molecular weight of less than about 5 kD and most preferably less than about 4 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

"Target molecules" include molecules with which a GPCR protein binds or interacts in nature, for example, a molecule on the surface of a cell which expresses a GPCR interacting protein; a molecule on the surface of a second cell; a molecule in the extracellular milieu; a molecule associated with the internal surface of a cell membrane; or a cytoplasmic molecule. A GPCR target molecule can be a non-GPCR molecule or a GPCR peptide of the invention. In one embodiment, a GPCR target molecule is a component of a signal transduction pathway that facilitates transduction of an extracellular signal, such as a signal generated by binding of a compound to a membrane-bound GPCR, through the cell membrane and into the cell. The target can be a second intercellular protein that has catalytic activity or a protein that facilitates the association of downstream signaling molecules with GPCR.

"Combination therapy" (or "co-therapy") includes the administration of a pepducin of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

By "homologous amino acid sequence" is meant an amino acid sequence, i.e., in a pepducin of the invention, that differs from a reference amino acid sequence, only by one or more (e.g., 1, 2, 3, 4 or 5) conservative amino acid substitutions, or by one or more (e.g., 1, 2, 3, 4 or 5) non-conservative amino acid substitutions, deletions, or additions located at positions at which they do not adversely affect the activity of the polypeptide. Preferably, such a sequence is at least 75%, 80%, 85%, 90%, or 95% identical to a reference amino acid sequence.

Homologous amino acid sequences include peptide sequences that are identical or substantially identical to a reference amino acid sequence. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM250 matrix described in Dayhoff et al., 5 ATLAS OF PROTEIN SEQUENCE AND STRUCTURE 345-352 (1978 & Suppl.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Preferably, a homologous sequence is one that is at least 45%, 50%, 55%, 60%, 65%, 70%, 75%, 80%, 85%, 90% or 95% identical to the reference amino acid sequence. Polypeptides having a sequence homologous to one of the sequences shown in this specification, e.g., Table 3, include naturally-occurring allelic variants, as well as mutants and variants or any other non-naturally-occurring variants that are analogous in terms of function, e.g., peptidomimetics.

This application is related to copending U.S. patent application Ser. No. 10/251,703, entitled "G Protein Coupled Receptor Agonists And Antagonists And Methods Of Activating And Inhibiting G Protein Coupled Receptors Using The Same" the entire contents of this patent application is incorporated herein by reference.

The present invention is based on the discovery of modified peptides called pepducins which comprise a cell-penetrating or membrane-tethering moiety to attached to a peptide derived from a GPCR i1 loop. Pepducins may be considered chimeric peptides/polypeptides, and are agonists and/or antagonists of receptor-G protein signaling and exhibit selectivity for their cognate receptor.

The pepducins of the invention include a GPCR moiety derived from the first intracellular loop (i1) of a GPCR, or a fragment thereof, and a cell penetrating or membrane-tethering moiety which partitions the conjugate into and across the lipid bilayer of target cells; and methods for their use in treatment of GPCR-mediated conditions. The cell penetrating moiety is, e.g., a hydrophobic region of the GPCR fragment itself. The cell penetrating or membrane-tethering moiety anchors the conjugate in the lipid bilayer (or to the cell surface), increasing the effective molarity of the conjugate in the vicinity of the intracellular receptor, e.g., at the receptor-G protein interface. The exogenous GPCR moiety of the pepducin disrupts receptor-G protein interactions and causes signaling activation and/or inhibition (i.e., agonistic or antagonistic activity).

Pepducins act as receptor-modulating agents by targeting the intracellular surface of the receptor. For example, pepducins of the present invention include PAR1- and PAR4-based antagonists for anti-hemostatic and anti-thrombotic effects under in vivo conditions. Because thrombin is the most potent activator of platelets, PAR1 (Vu et al. *Cell* 64, 1057 (1991)) and PAR4 (Xu et al. *Proc. Natl. Acad. Sci.* (USA) 95, 6642 (1998); Covic et al. *Biochemistry* 39, 5458 (2000); and Covic et al. *Thromb. Haemost.* 87, 722 (2002)) were chosen as targets. Antagonists of these two receptors are useful to prevent the thrombotic and proliferative complications of acute coronary syndromes, including sepsis.

Ischemia reperfusion injury occurs when the blood flow is restored after an extended period of ischemia. It is a common source of morbidity and mortality in conditions such as myocardium infarction, stroke, gut ischemia, and cardiopulmonary bypass; for which there is often no specific therapy. Pepducins of the invention are administered intravenously to provide significant protection against experimental reperfusion injury of heart muscle.

Myocardial infarction prompted by the limited supply of cardiac muscle with arterial blood, is a leading cause of heart failure and death. The emergent restoration of normal circulation is, therefore, critical for the prevention of the irreversible damage of cardiac tissues from hypoxia. The re-establishment of the normal blood flow can occur naturally or artificially after treatment of myocardial infarction (MI) patients with specific drugs. In many cases, however, reperfusion of the infarcted area initiates the inflammatory response that facilitates the damage of cardiac cells and thereby attenuates the positive effect of restored circulation. It was demonstrated that white blood cells recruited into the hypoxic areas of reperfused tissues significantly contribute to this pathological inflammatory response.

Organ transplantation is now common with over 22,000 procedures performed in the US in 2001; the most commonly transplanted organs being the kidney, liver and heart. The large numbers of transplants now being conducted is due in part to the ability of immunomodulatory agents to control acute rejection. Delayed graft function, caused by ischemia-reperfusion injury, and host v. graft reaction are the principal mechanisms of acute rejection after transplantation. The use of immunosuppressants has successfully dealt with acute rejection and the allograft commonly survives for prolonged periods, even though immunosuppressive drug dosages are reduced to very low levels.

However, immunosuppressants suppress all immunologic reactions, making overwhelming infection the leading cause of death in transplant recipients. Immunosuppressants are also associated with severe toxicity. The most significant complications of drugs used for transplant patients include nephrotoxicity, neurotoxicity, new-onset post-transplant diabetes mellitus, hyperlipidemia, and hypertension. These side effects occur in part because of the ubiquitous expression of the molecular targets of currently used immunosuppressants. Therapeutic strategies including pepducins of the present invention are able to specifically target ischemia-reperfusion injury and the subsequent infiltration of mononuclear cells, a primary cause of acute rejection.

Severe sepsis is a leading cause of acute hospital admissions and often complicates the clinical course of patients treated for other diseases. At the onset of sepsis, the presence of bacteria and bacterial products such as endotoxin stimulates immune defense mechanisms. Failure to remove the invading pathogens initiates hyperactive inflammatory responses termed systemic inflammatory response syndrome (SIRS), which is mediated by cytokines and chemokines. Chemokines are viewed as therapeutic targets in inflammation. CXCR1 and CXCR2 are important chemokine receptors responsible for the activation of neutrophils, endothelium, epithelium, macrophages and other cells. Mice rendered deficient in IL-8 signaling by genetic deletion of their sole IL-8 receptor, CXCR2, protects mice from developing sepsis.

In humans, exposure to high systemic IL-8 levels leads to endothelial dysfunction and loss of the normal anti-coagulant state of endothelium. Disorders of coagulation occur in 30-50% of septic patients and the development of overt disseminated intravascular coagulation (DIC) is an ominous prognostic sign. Opposing the action of CXCR1/2, CXCR4 directs the removal of senescent neutrophils and retains immature leukocytes in the bone marrow. CXCR4 also plays a prominent role in the homing mechanisms of lymphocytes and cancer cells, but the function of CXCR4 and its ligand SDF-1α in acute inflammation remains enigmatic.

Apart from administration of antibiotics, the treatment of sepsis and septic shock is largely limited to supportive strategies. Presently no specific therapeutic interventions directed against chemokine receptors are available for the treatment of sepsis, though small molecule inhibitors directed against CXCR1/2 can protect against reperfusion injury and lung damage. Pepducins of the invention can be used to interrupt established systemic inflammation and vascular damage as well prevent activation of the coagulation cascade without interference with host defense.

The Human PARs include PAR1 (Genbank Accession Number AF019616); PAR2 (Genbank Accession Number XM_003671); PAR3 (Genbank Accession Number NM_0041101); and PAR4 (Genbank Accession Number NM_003950.1), the sequences of which are hereby incorporated by reference.

A two-site mechanism by which pepducins both activate and inhibit receptor-G protein signaling is described herein, but the inventors do not intend to have their invention be limited by this mechanism or the theory on which it is based. The mechanism accommodates the biphasic activation and inhibition of the agonists and the inhibition of the antagonists. Pepducins, by virtue of their hydrophobic tether, rapidly transduce the plasma membrane and achieve high effective molarity at the perimembranous interface. The pepducin agonist first occupies a high-affinity site at the intracellular surface of the GPCR. The bound agonist either stabilizes or induces the activated state of the receptor to turn on the associated G protein(s). After this first site becomes saturated, higher concentrations of pepducin begin to occupy a second, lower-affinity, inhibitory site that blocks signal transference to G protein in a dominant manner, perhaps by mimicking the GPCR (e.g., the receptor i1-loop) ground-state interactions with the G protein. The inhibition by the pepducin antagonists is coincident with the inhibitory phase of the agonists, thus the antagonists may also bind at this lower affinity site. Exogenous activation or inhibition of receptors by pepducins could reflect a potential dimerization mode whereby one receptor donates its intracellular loops to an adjacent receptor. There are several examples of receptor dimers that give rise to distinct signaling properties (Milligan, Science 288, 65-67 (2000)), including the cytokine/GPCRs such as the EPO receptor (Guillard et al, J. Biol. Chem. (2001) 276, 2007-2013), however, the mechanism(s) of cross-receptor modulation is unknown.

A naturally-occurring GPCR is a cell surface molecule that crosses a cell membrane at least once. For example, many naturally-occurring GPCRs cross a cell membrane seven times and contain several intracellular domains. The isolated GPCR fragment of the invention includes the first intracellular loop domain of a GPCR. The intracellular portion is selected from the first intracellular loop domain of a one-transmembrane domain G-protein coupled receptor of a cytokine GPCR, or a fragment thereof, or the first intracellular loop domain of a multi-polypeptide-GPCR, such as a GPIb/V/IX receptor or a collagen receptor.

The invention also includes soluble pepducins wherein the second domain (cell-penetrating- or membrane-tethering moiety) optionally includes a naturally occurring contiguous amino acid from a transmembrane domain adjacent to the extracellular or intracellular fragment. For example, the construct may contain at least 3, but less than 16 contiguous amino acids of a GPCR transmembrane helix domain. The transmembrane domain is not transmembrane domain 1-7 of the CXCR4, transmembrane domain 1-7 of CCKA receptor, or transmembrane 2 of the CCR5 receptor. In an embodiment, the second domain includes 1-15 contiguous amino acids of a naturally-occurring transmembrane helix domain immediately adjacent to the extracellular or intracellular fragment.

In addition to peptide-based pepducins, the invention encompasses compositions in which the GPCR fragment contains a peptidomimetic. For example, the invention includes pepducin compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a noncleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis.

Pepducin compounds of the invention can be synthesized as retro-inverso isomers, which include peptides of reverse sequence and chirality. See, e.g., Jameson et al. Nature 368:

744-746 (1994) and Brady et al. *Nature* 368:692-693 (1994). The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art.

Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

An isolated GPCR fragment may be derived from the sequence of a Class A GPCR or a Class B GPCR. The isolated GPCR fragment is a fragment from any known or unknown GPCR, including, but not limited to protease activated receptors (PARs, e.g., a thrombin receptor), a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide (VIP) receptor, a secretin receptor, a growth hormone releasing factor (GRF) receptor, cholecystokinin receptors, somatostatin receptors, melanocortin receptors, nucleotide (e.g., ADP receptors), adenosine receptors, thromboxane receptors, platelet activating factor receptors, adrenergic receptors, 5-hydroxytryptamine (5-HT) receptors, chemokine receptors (e.g., CXCR4, CCR5), neuropeptide receptors, opioid receptors, erythropoietin receptor, and parathyroid hormone (PTH) receptor.

In preferred embodiments, the GPCR is a protease-activated receptor, a peptide receptor, or a nucleotide receptor. In particular embodiments, the GPCR is a PAR1, PAR2, PAR3, or a PAR4 receptor. In other embodiments, the GPCR is a glucagon-like receptor, a nucleotide receptor, such as a $P2Y_{12}$ ADP receptor, a MC4 obesity receptor, a CXCR receptor (e.g., CXCR4) or CCR5 chemokine receptors, CCKA, or CCKB.

An isolated GPCR fragment may include a GPCR fragment which is less than 50 contiguous amino acid from the GPCR, and does not contain the native extracellular ligand of the GPCR. For example, the fragment may contain between 3 and 30 contiguous amino acids of a GPCR. In preferred embodiments, the GPCR fragment comprises a GPCR fragment which is between 7 and 24 (inclusive) contiguous amino acids. For example, the fragment includes 7, 8, 9, 10, 11, 12, 13, 14, 15, 16, 17, 18, 19, 20, 21, 22, 23, or 24 contiguous amino acids of a GPCR.

Optionally, the amino acid sequence of a GPCR differs from a naturally-occurring amino acid sequence. For example, individual residues from a given domain, e.g., a transmembrane helix, extracellular, or intracellular loop, are mutated or substituted with a modified amino acid(s) to improve activity of the pepducin. Preferably, the amino acid sequence of such a GPCR analog differs solely by conservative amino acid substitutions, i.e., substitution of one amino acid for another of the same class, or by non-conservative substitutions, deletions, or insertions located at positions that do not destroy the function of the protein.

The GPCR moiety of the pepducins of the present invention are derived from any cells of a human being or other organism (e.g., guinea pig, rat, mouse, chicken, rabbit, pig, sheep, cattle, monkey, virus, fungi, insects, plants, bacteria, etc.), for example, splenic cell, nerve cell, glia cell, beta cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutrophil, basophil, eosinophilic leukocyte, monocyte, etc.), megakaryocyte, synovial cell, chondrocyte, osteocyte, osteoblast, osteoclast, mammary gland cell, hepatocyte, or interstitial cells or precursor cells, stem cells or cancer cells thereof and the like; and any tissues containing such cells, for example, brain, various parts of the brain (e.g., olfactory bulb, amygdala, cerebral basal ganglia, hippocampus, thalamus, hypothalamus, substhanlamic nucleus, cerebral cortex, medulla, cerebellum, occipital pole, frontal lobe, putamen, caudate nucleus, corpus callosum, substantia nigra), spinal cord, pituitary, stomach, pancreas, kidney, liver, genital organs, thyroid gland, gallbladder, bone marrow, adrenal gland, skin, muscle, lung, digestive tract, blood vessel, heart, thymus, spleen, submandibular gland, peripheral blood, peripheral blood leukocyte, intestinal tract, prostate, testicle, testis, ovarium, placenta, uterus, bone, joint, small intestine, large intestine, skeletal muscle and the like, in particular, brain and various parts of the brain.

Cell-penetrating moieties include a lipid, cholesterol, a phospholipid, steroid, sphingosine, ceramide, or a fatty acid moiety. The fatty acid moiety can be, e.g., any fatty acid which contains at least eight carbons. For example, the fatty acid can be, e.g., a nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); or a lignoceroyl ($C_{24}$) moiety. The cell-penetrating moiety can also include multimers (e.g., a composition containing more than one unit) of octylglycine, 2-cyclohexylalanine, or benzolylphenylalanine. The cell-penetrating moiety contains an unsubstituted or a halogen-substituted (e.g., chloro) biphenyl moiety. Substituted biphenyls are associated with reduced accumulation in body tissues, as compared to compounds with a non-substituted biphenyl. Reduced accumulation in bodily tissues following administration to a subject is associated with decreased adverse side effects in the subject.

Preferably, the cell penetrating moiety is a naturally-occurring or non-naturally occurring palmitoyl moiety. Pepducins with longer than $C_{15}$ fatty acids, e.g., palmitoyl, moieties appear to be surprisingly long-lived in vivo and are suitable for subcutaneous administration. In another embodiment, pepducins having shorter than $C_{15}$, e.g., myristyl, moieties, appear to be useful for short-term applications, e.g., surgical applications, and intravenous administration is useful here.

The cell-penetrating or membrane-tethering moiety may be attached to the C-terminal amino acid, the N-terminal amino acid, or to an amino acid between the N-terminal and C-terminal amino acid of the GPCR fragment.

Also within the invention is a composition which includes a polypeptide having an amino acid sequence of SEQ ID NOs: 1-14, or portions thereof, linked to a cell penetrating or membrane-tethering moiety. Particularly suitable pepducins of the invention include those listed below in Table 1.

TABLE 1 i1 loop pepducins

| Receptor | Pepducin | Sequence | Length | Lipid modification | MW | SEQ ID NO. |
|---|---|---|---|---|---|---|
| PAR2 | P2i1pal12 | FLFRTKKKHPAV | 12 | palmitate | 1708 | 17 |
| CXCR1 | x1/2i1pal12 | ILYSRVGRSVTD | 12 | palmitate | 1602 | 18 |
| CXCR1 | x1/2i1myr10 | YSRVGRSVTD | 10 | myristate | 1376 | 19 |
| CXCR1 | x1/2i1LCA10 | YSRVGRSVTD | 10 | lithocholate | 1497 | 20 |
| CXCR2 | x1/2i1pal12 | ILYSRVGRSVTD | 12 | palmitate | 1602 | 21 |
| CXCR2 | x1/2i1myr10 | YSRVGRSVTD | 10 | myristate | 1376 | 22 |
| CXCR2 | x1/2i1LCA10 | YSRVGRSVTD | 10 | lithocholate | 1497 | 23 |
| CXCR4 | x4i1pal10 | YQKKLRSMTD | 10 | palmitate | 1508 | 24 |
| CXCR4 | x4i1pal12 | MGYQKKLRSMTD | 12 | palmitate | 1697 | 25 |
| CCR5 | CC5i1pal8 | KRLKSMTD | 8 | palmitate | 1215 | 26 |
| CCR5 | CC5i1pal12 | LINCKRLKSMTD | 12 | palmitate | 1658 | 27 |
| PAR1 | P1i1pal11 | pal-ILKMKVKKPAV | 11 | palmitate | 1491.6 | 28 |
| PAR4 | P4i1pal12 | pal-VLATQAPRLPST | 12 | palmitate | 1489.9 | 29 |
| PAR4 | P4i1pal10 | pal-ATQAPRLPST | 10 | palmitate | 1277.6 | 30 |
| PAR4 | P4i1pal12G | pal-VLATGAPRLPST | 12 | palmitate | 1418.8 | 31 |
| PAR4 | P4i1pal10G | pal-ATGAPRLPST | 10 | palmitate | 1206.5 | 32 |

The compositions are used to treat, prevent, or ameliorate (reduce the severity of) one or more symptoms associated with diseases and conditions characterized by aberrant GPCR activity. Such diseases and conditions include thrombosis, heart attack, stroke, excessive bleeding, asthma, inflammation, pain, inflammatory pain, visceral pain, neurogenic pain, arthritis, diabetes, HIV infection, anxiety, depression, pulmonary insufficiency, and various types of cancer. Such methods are carried out by contacting a cell, which pathologically overexpresses a GPCR with a pepducin GPCR antagonist. For example, the method involves administering to a subject, e.g., a human patient, in which such treatment or prevention is desired a pepducin in an amount sufficient to reduce the severity of the pathology in the subject. The present invention also includes pharmaceutical compositions containing any of the pepducin compositions and a pharmaceutically acceptable carrier. The invention also includes kits containing the pharmaceutical compositions. The invention further includes methods of treating a pathological state in a mammal through the administration of any polypeptide of the invention.

The constructs are also used to inhibit tumor growth and migration. Breast cancer cell invasion is a complex process in which cell migration, proteolytic modifications of tissue basement membranes, and degradation of extracellular matrices by matrix metalloproteases (MMP) take place. Activation of PAR1 by MMP1 plays a critical role in invasion and tumorigenesis of breast cancer cells (Boire et al. *Cell*, 120(3), 303 (2005)). A PAR1 i1 loop pepducin antagonist, e.g., P1i1pal11, is used alone or as an adjuvant cancer treatment, e.g., when administered with a docetaxel compound such as Taxotere®. Preferably, a synergistic antitumor effect is achieved. The effect of intracellular inhibition of PAR1 is demonstrated using the metastatic human breast cancer cell line MDA-MB-231. Pepducin efficacy alone and in combination therapy, e.g., together with Taxotere is analyzed using the MTT assay and a xenograft mice model. The $IC_{50}$ of the pepducin P1i1pal11 and Taxotere is determined after the compositions are administered separately or together. The Isobologram technique and the combination index (CI) method is employed to quantify the degree of synergy. Xenograft data is used to determine whether the tumor growth rates were suppressed in mice treated with P1i1pal11 and Taxotere together compared to the mice that were treated only with Taxotere. The compounds reduce tumor growth migration at all stages of tumor development, e.g., early in tumor development as well as at later stages of tumor development.

Figure 27:
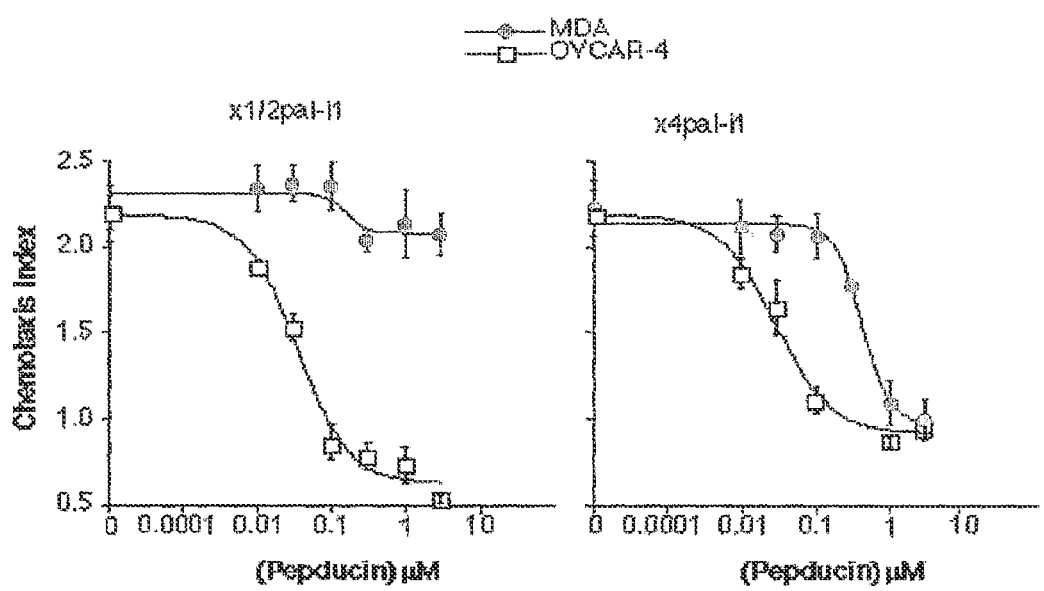
FIG. 27 is a graph illustrating how i1-loop pepducins block chemotactic migration of breast and ovarian cancer cells. Conditioned media was prepared from NIH3T3. Chemotaxis assays (20 h) were performed using a 48 blindwell microchemotaxis chamber (Neuroprobe) equipped with 8 mm pore nitrocellulose filters for OVCAR-4 human ovarian cancer cells and MDA-MB-231 human breast cancer cells. Data is expressed as chemotaxis index which is the ratio between the distance of migration toward NIH3T3 conditioned media over migration toward RPMI medium alone.

For example, as seen FIG. 27, I1-loop pepducins based on the CXCR1/2 (x1/2pal-i1) and CXCR4 (x4pal-i1) chemokine receptors block chemotactic migration of breast and ovarian cancers.

Certain pepducins of the invention are platelet activation inhibitors. The inhibitor contains an isolated fragment of a protease activated receptor and a cell penetrating moiety linked to the GPCR polypeptide. In some embodiments, the protease activated receptor is a thrombin receptor, a trypsin receptor, clotting factor Xa receptor, activated protein C receptor, tryptase receptor, or a plasmin receptor. The thrombin receptor is preferably PAR-4 or PAR-1.

The invention also includes a method of inhibiting platelet aggregation, by contacting a platelet with a composition of an isolated fragment of a protease activated receptor linked to a cell penetrating moiety as described above. For example, the protease activated receptor is a thrombin receptor, such as a PAR-1 receptor or a PAR-4 receptor. Also within the invention is a method of inhibiting thrombus formation in a mammal by administering to the mammal a composition of the invention which includes an isolated fragment of a thrombin receptor linked to a cell penetrating moiety.

The methods of the invention are carried out by infusing into a vascular lumen, e.g., a jugular vein, peripheral vein or the perivascular space, the inhibitory compositions of the invention. The peripheral vein can be, e.g., a vein located in the extremities, such as the hand, wrist, or foot. In some embodiments, the composition is infused into the lungs of the mammal, e.g., as an aerosol. In other embodiments, the composition of the invention is administered by injection. In various embodiments, the injection can be into the peritoneal cavity of the mammal, subdermally, or subcutaneously. The composition of the invention can also be administered transdermally. In other embodiments, the composition of the invention is administered vaginally or rectally. The composition can be administered by implanting wound packing material or a suppository which is coated or impregnated with the composition of the invention.

Inhibitors of clot formation or platelet aggregation are used in medical devices, e.g., as coatings. For example, a vascular endoprosthetic device, e.g., a screen, stent or catheter, includes an inhibitor of thrombus formation which is an isolated fragment of a thrombin receptor linked to a cell penetrating moiety. The composition is impregnated in the device and diffuses into bodily tissues upon contact with a tissue or implantation of the device; alternatively, the device is coated with the pepducin.

Pepducins are also used to inhibit migration and invasion of a tumor cell by contacting the tumor cell with an isolated fragment of a protease activated receptor linked to a cell penetrating moiety. The protease activated receptor is a PAR-4, PAR-2, or a PAR-1 receptor. Methods of inhibiting metastases of a tumor cell are carried out by contacting the tumor cell with an isolated fragment of a protease activated receptor linked to a cell-penetrating moiety. The tumor cell is a melanoma cell, a breast cancer cell, a renal cancer cell, a prostate cancer cell, a lung cancer cell, a colon cancer cell, a central nervous system (CNS) cancer cell, a liver cancer cell, a stomach cancer cell, a sarcoma cell, a leukemia cell, or a lymphoma cell.

Symptoms of asthma are reduced by administering a thrombin or a trypsin/tryptase GPCR based pepducin. Accordingly, a method of inhibiting asthma is carried out by administering a composition containing an isolated fragment of a thrombin or a trypsin/tryptase GPCR linked to a cell penetrating moiety. Preferably, the trypsin/tryptase receptor is a PAR-1, PAR-2 or PAR-4 receptor. In various embodiments, the composition is infused into a vascular lumen, such as a peripheral vein, is infused into the lungs of the mammal, e.g., by inhalation (e.g., as an aerosol), or is administered by a transdermal route.

Inhibitors of platelet activation include an isolated fragment of a nucleotide activated GPCR such as a $P2Y_{12}$ receptor linked to a cell penetrating moiety. Such compositions are useful in methods of inhibiting platelet aggregation.

In yet another aspect, the invention includes a method of inhibiting thrombus formation in a mammal by administering a composition including an isolated fragment of a nucleotide activated receptor linked to a cell penetrating moiety to the mammal. In some embodiments, the thrombin receptor is a $P2Y_{12}$ receptor. The method can be carried out by infusing into a vascular lumen, e.g., a jugular vein, peripheral vein the inhibitory compositions of the invention. The peripheral vein can be, e.g., a vein located in the extremities, such as the hand, wrist, or foot. In some embodiments, the composition is infused into the lungs of the mammal, e.g., as an aerosol. In other embodiments, the composition of the invention is administered by injection. In various embodiments, the injection can be into the peritoneal cavity of the mammal, subdermally, or subcutaneously. In other embodiments, the composition of the invention is administered transdermally. The composition can be administered by implanting wound packing material or a suppository which is coated or impregnated with the composition of the invention.

In another aspect, the invention includes a vascular endoprosthetic device, which includes an inhibitor of thrombus formation which is an isolated fragment of a nucleotide receptor linked to a cell penetrating moiety. In various embodiments, the device can be, e.g., a stent or a catheter. In some embodiments, the device is impregnated with or coated with the inhibitor.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications cited in this specification are incorporated herein by reference.

G Protein Coupled Receptors

G protein coupled receptors are intrinsic membrane proteins which comprise a large superfamily of receptors. The family of G protein-coupled receptors (GPCRs) has at least 250 members (Strader et al. FASEB J., 9:745-754, 1995; Strader et al. Annu. Rev. Biochem., 63:101-32, 1994). It has been estimated that one percent of human genes may encode GPCRs. Many GPCRs share a common molecular architecture and common signaling mechanism. Historically, GPCRs have been classified into six families, originally thought to be unrelated, three of which are found in vertebrates. Recent work has identified several new GCPR families and suggested the possibility of a common evolutionary origin for all of them.

Many GPCRs share a common structural motif of seven transmembrane helical domains. Some GPCRS, however, do not have seven transmembrane helical domains and instead can be single-spanning transmembrane receptors.

Single spanning GPCRs include receptors for cytokines such as erythropoietin, EGF, insulin, insulin-like growth factors I and II, and TGF.

GPCR families include Class A Rhodopsin like, Class B Secretin like, Class C Metabotropic glutamate/pheromone, Class D Fungal pheromone, Class E cAMP receptors (Dictyostelium), and Frizzled/Smoothened family. Putative families include Ocular albinism proteins, Drosophila odorant receptors, Plant Mlo receptors, Nematode chemoreceptors, and Vomeronasal receptors (V1R & V3R).

Class A Rhodopsin like receptors include: Amine receptors: Acetylcholine, Alpha Adrenoceptors, Beta Adrenoceptors, Dopamine, Histamine, Serotonin, Octopamine, and Trace amine; Peptide receptors: Angiotensin, Bombesin, Bradykinin, C5a anaphylatoxin, Fmet-leu-phe, APJ like, Interleukin-8, Chemokine receptors (C—C Chemokine, C—X—C Chemokine, BONZO receptors (CXC6R), C—X3-C Chemokine, and XC Chemokine), CCK receptors, Endothelin receptors, Melanocortin receptors, Neuropeptide Y receptors, Neurotensin receptors, Opioid receptors, Somatostatin receptors, Tachykinin receptors, (Substance P (NK1), Substance K (NK2), Neuromedin K (NK3), Tachykinin like 1, and Tachykinin like 2), Vasopressin-like receptors (Vasopressin, Oxytocin, and Conopressin), Galanin like receptors (Galanin, Allatostatin, and GPCR 54), Proteinase-activated like receptors (e.g., Thrombin), Orexin & neuropeptide FF, Urotensin II receptors, Adrenomedullin (G10D) receptors, GPR37/endothelin B-like receptors, Chemokine receptor-like receptors, and Neuromedin U receptors; Hormone protein receptors: Follicle stimulating hormone, Lutropin-choriogonadotropic hormone, Thyrotropin, and Gonadotropin; (Rhod)opsin receptors; Olfactory receptors; Prostanoid receptors: Prostaglandin, Prostacyclin, and Thromboxane; Nucleotide-like receptors: Adenosine and Purinoceptors; Cannabis receptors; Platelet activating factor receptors; Gonadotropin-releasing hormone receptors; Thyrotropin-releasing hormone & Secretagogue receptors: Thyrotropin-releasing hormone, Growth hormone secretagogue, and Growth hormone secretagogue like; Melatonin receptors; Viral receptors; Lysosphingolipid & LPA (EDG) receptors; Leukotriene B4 receptor: Leukotriene B4 receptor BLT1 and Leukotriene B4 receptor BLT2; and Class A Orphan/other receptors: Platelet ADP & KI01 receptors, SREB, Mas proto-oncogene, RDC1, ORPH, LGR like (hormone receptors), GPR, GPR45 like, Cysteinyl leukotriene, Mas-related receptors (MRGs), and GP40 like receptors.

Class B (the secretin-receptor family or 'family 2') of the GPCRs is a smaller but structurally and functionally diverse group of proteins that includes receptors for polypeptide hormones (Calcitonin, Corticotropin releasing factor, Gastric inhibitory peptide, Glucagon, Glucagon-like peptide-1,-2, Growth hormone-releasing hormone, Parathyroid hormone, PACAP, Secretin, Vasoactive intestinal polypeptide, Diuretic hormone, EMR1, Latrophilin), molecules thought to mediate intercellular interactions at the plasma membrane (Brain-specific angiogenesis inhibitor (BAI)) and a group of Drosophila proteins (Methuselah-like proteins) that regulate stress responses and longevity.

Class C Metabotropic glutamate/pheromone receptors include Metabotropic glutamate, Metabotropic glutamate group I, Metabotropic glutamate group II, Metabotropic glutamate group III, Metabotropic glutamate other, Extracellular calcium-sensing, Putative pheromone Receptors, GABA-B, GABA-B subtype 1, GABA-B subtype 2, and Orphan GPRC5 receptors.

GPCRs can potentially be multi-polypeptide receptors such as GPIb-V-IX, or the collagen receptor, that exhibit outside-in-signaling via G proteins.

Although hundreds of G protein coupled receptor genes or cDNAs have been cloned, it is believed that there are still many uncharacterized G protein coupled receptors which have not yet been recognized as GPCRs.

GPCRs play a vital role in the signaling processes that control cellular metabolism, cell growth and motility, adhesion, inflammation, neuronal signaling, and blood coagulation. G protein coupled receptor proteins also have a very important role as targets for a variety of signaling molecules which control, regulate, or adjust the functions of living bodies. The signaling species can be endogenous molecules (e.g., neurotransmitters or hormones), exogenous molecules (e.g., odorants), or, in the case of visual transduction, light.

For instance, GPCRs include receptors for biogenic amines, e.g., dopamine, epinephrine, histamine, glutamate (metabotropic effect), acetylcholine (muscarinic effect), and serotonin; receptors for lipid mediators of inflammation such as prostaglandins, platelet activating factor, and leukotrienes; receptors for peptide hormones such as calcitonin, C5a anaphylatoxin, follicle stimulating hormone, gonadotropin releasing hormone, neurokinin, oxytocin; receptors for proteases such as thrombin, trypsin, tryptase, activated protein C, and factor VIIa/Xa; and receptors for sensory signal mediators, e.g., retinal photopigments and olfactory stimulatory molecules. Each molecule is specific to a receptor protein, whereby the specificities of individual physiologically active substances (including specific target cells and organs), specific pharmacological actions, specific action strength, action time, etc., are decided. Thus, GPCRs are a major target for drug action and development.

Upon ligand binding, GPCRs regulate intracellular signaling pathways by activating guanine nucleotide-binding proteins (G proteins). The domain structure of GPCRs are conserved among members of the GPCR family. Domain boundaries of TM helix domains, intracellular loop domains, and extracellular domains of GPCRS are known in the art. The structure of unmapped GPCRs is determined by comparison to the prototype GPCR, rhodopsin, using known methods, e.g., as described in Palczewski et al., Science 289: 739 (2000), hereby incorporated by reference.

One characteristic feature of most GPCRs is that seven clusters of hydrophobic amino acid residues, or transmembrane regions (TMs, the 7 transmembrane regions are designated as TM1, TM2, TM3, TM4, TM5, TM6, and TM7) are located in the primary structure and pass through (span) the cell membrane at each region thereof (FIG. 1). The domains are believed to represent transmembrane alpha-helices connected by three intracellular loops (i1, i2, and i3), three extracellular loops (e1, e2, and e3), and amino (N)- and carboxyl (C)-terminal domains (Palczewski et al., Science 289, 739-45 (2000)). Most GPCRs have single conserved cysteine residues in each of the first two extracellular loops which form disulfide bonds that are believed to stabilize functional protein structure. It is well known that these structures detailed above are common among G protein coupled receptor proteins and that the amino acid sequences corresponding to the area where the protein passes through the membrane (membrane-spanning region or transmembrane region) and the amino acid sequences near the membrane-spanning region are often highly conserved among the receptors. Thus, due to the high degree of homology in GPCRS, the identification of novel GPCRs, as well identification of both the intracellular and the extracellular portions of such novel members, is readily accomplished by those of skill in the art.

The binding sites for small ligands of G-protein coupled receptors are believed to comprise a hydrophilic socket located near the extracellular surface which is formed by several GPCR transmembrane domains. The hydrophilic socket is surrounded by hydrophobic residues of the G-protein coupled receptors. The hydrophilic side of each G-protein coupled receptor transmembrane helix is postulated to face inward and form the polar ligand binding site. TM3 has been implicated in several GPCRs as having a ligand binding site which includes the TM3 aspartate residue. TM5 serines, a TM6 asparagine and TM6 or TM7 phenylalanines or tyrosines are also implicated in ligand binding. The ligand binding site for peptide hormones receptors and receptors with other larger ligands such as glycoproteins (e.g., luteinizing hormone, follicle stimulating hormone, human chorionic gondaotropin, thyroid-stimulating hormone (Thyrotropin)), and the $Ca^{2+}$/glutamate/GABA (gamma-aminobutyric acid) classes of receptors likely reside in the extracellular domains and loops.

A key event for the switch from inactive to active receptor is ligand-induced conformational changes of transmembrane helices 3 (TM3) and 6 (TM6) of the GPCRs that have 7 transmembrane spanning helices (Gether and Kolbilka, J. Biol. Chem. 273, 17979-17982 (1998)). These helical movements in turn alter the conformation of the intracellular loops of the receptor to promote activation of associated heterotrimeric G proteins. Mutagenesis studies (Cotecchia et al., J. Biol. Chem. 267:1633-1639 (1992); Kostenis et al., Biochemistry 36:1487-1495 (1997); Kjelsberg et al., J. Biol. Chem. 267:1430-1433 (1992)) demonstrated that the third intracellular loop (i3) mediates a large part of the coupling between receptor and G protein. I3 loops expressed as minigenes have also been shown to directly compete with adrenergic receptors for Gq binding (Luttrel et al., Science 259: 1453-1457 (1993)), or can activate G proteins as soluble peptides in cell-free conditions (Okamoto et al, Cell 67, 723-730 (1991)).

One particular class of GPCR is the protease activated receptors (PARs). Protease-activated receptors (PARs) are members of the superfamily of G-protein-coupled receptors that initiate cell signaling by the proteolytic activity of extracellular serine proteases. PARs are activated after proteolytic cleavage of the amino terminus of the receptor by endogenous proteases, including thrombin (PAR-1, -3, and -4) and trypsin/tryptase (PAR-2 and -4). Of these, PAR2 (Nystedt et al., Proc. Natl. Acad. Sci. (USA) 91:9208-9212 (1994)) is a trypsin/tryptase-activated receptor that is important in inflammation and pain, and PAR4 (Xu et al., Proc. Natl. Acad. Sci. (USA) 95:6642-6646 (1998); Kahn et al., Nature (London) 394:690-694 (1998)) is a second thrombin receptor that plays a unique role in platelet aggregation (Covic et al., Biochemistry 39, 5458-5467 (2000)).

Because both thrombin, trypsin, and tryptase are present in inflamed airways, PARs are likely to play a major role in airway inflammation. Knight et al., J. Allergy Clin. Immunol. 108:797-803 (2001).

In addition to its pivotal role in hemostasis, thrombin activates various cell types such as platelets and vascular smooth muscle cells via proteolytic cleavage of specific cell-surface receptors (PARs), the prototype of which is PAR-1. Thrombin receptor activation is likely to play a key role in cardiovascular disorders such as thrombosis, atherosclerosis and restenosis, and as such a thrombin receptor antagonist should have potential utility in the treatment of these disorders. Chackalamannil, Curr. Opin. Drug Discov. Devel. 4:417-27 (2001).

Thrombin is thought to be involved in functional loss after injury to the mammalian central nervous system (CNS). Down-regulation of PAR-1 has been shown to increase post-traumatic survival of CNS neurons and post-traumatic toxicity of thrombin may be down-regulated by appropriate modulation of PAR-I receptors. Friedmann et al., Neuroimmunol., 121:12-21 (2001).

PARS are also involved in a variety of other diseases or indications, including various cancers, cellular proliferation, and pain.

GPCR Domains

Most GPCRs are characterized by seven clusters of hydrophobic amino acid residues, or transmembrane regions (TMs, the 7 transmembrane regions are designated as TM1, TM2, TM3, TM4, TM5, TM6, and TM7), that are located in the primary structure and pass through (span) the cell membrane (FIG. 1A). The TM regions are believed to represent transmembrane alpha-helices connected by three intracellular loops (i1, i2, and i3), three extracellular loops (e1, e2, and e3). GPCRs also contain amino (N)- and carboxyl (C)-terminal domains (Palczewski et al., Science 289, 739-45 (2000)). The sequences between the transmembrane regions correspond to GPCR loops, and the location of a loop within a cell determines whether it is an intracellular or an extracellular loop. Most GPCRs have single conserved cysteine residues in each of the first two extracellular loops which form disulfide bonds that are believed to stabilize functional protein structure. A schematic representation of transmembrane and loop regions of the PAR1 GPCR is presented in FIG. 1A.

One example of a GPCR is the CXCR4 receptor, shown in Table 2 as SEQ ID NO:15. The seven underlined sequences correspond to the seven transmembrane regions of the GPCR. Thus, the sequence IFLPTIYSIIFLTGIVGNGLVILV (SEQ ID NO:16) corresponds to the first transmembrane region (TM1).

TABLE 2

CXCR4

(SEQ ID NO: 15)

MEGISIYTSD NYTEEMGSGD YDSMKEPCFR EENANFNK<u>IF LPTIYSIIFL TGIVGNGLVI</u>

LVMGYQKKLR SMTDKYRL<u>HL SVADLLFVIT LPFWAVDAVA</u> NWYFGNFLCK <u>AVHVIYTVNL</u>

<u>YSSVLILAFI SLDRYLAIVH</u> ATNSQRPRKL LAEK<u>VVYVGV WIPALLLTIP DFIFANVSEA</u>

DDRYICDRFY PNDLWVVVFQ <u>FQHIMVGLIL PGIVILSCYC IIISKLSHSK</u> GHQKRKALKT

TVILTLAFFA CWLPYYIGIS IDSFILLEII KQGCEFENTV HKW<u>ISITEAL AFFHCCLNPI</u>

<u>LYAFL</u>GAKFK TSAQHALTSV SRGSSLKILS KGKRGGHSSV STESESSSFH SS.

An isolated GPCR fragment is any portion of the GPCR which is less than the full length protein. A peptide containing an isolated GPCR fragment may contain an amino acid sequence N-terminal and/or C-terminal to the GPCR sequence other than the naturally occurring amino acid sequence. A peptide containing an isolated transmembrane sequence of a GPCR may contain only the sequence corresponding to that transmembrane region of the GPCR, or it may also contain amino acid sequences N-terminal and/or C-terminal to the transmembrane sequence, that are not the naturally occurring flanking sequences (i.e., not the loop sequences which are adjacent to that region in the naturally occurring GPCR sequence).

Thus, a peptide containing an isolated transmembrane region of the CXCR4 receptor is any peptide that contains any or all of the contiguous amino acids of an underlined region of sequence shown in Table 2. Such a peptide does not contain any of the naturally occurring (non-underlined) flanking sequence which corresponds to loop sequences which are adjacent to that TM region in the naturally occurring GPCR sequence.

Likewise, a peptide containing an isolated (intracellular or extracellular) loop region of the CXCR4 receptor is any peptide that contains any or all contiguous amino acids of a non-underlined region of sequence shown in Table 2. Such a peptide does not contain any of the naturally occurring transmembrane sequences, shown as underlined flanking sequence in Table 2, which are adjacent to that loop region in the naturally occurring GPCR sequence.

A peptide containing an isolated extracellular domain or an isolated intracellular domain can include amino acid sequences from any (extracellular or intracellular) loop and/ or the N- or C-terminal domain. Such a peptide does not include any sequence from a transmembrane region which is adjacent to that extracellular domain or intracellular domain in the naturally occurring GPCR sequence.

Pharmaceutical Compositions

The pepducins (also referred to herein as "active compounds") of the invention, and derivatives, fragments, analogs and homologs thereof, can be incorporated into pharmaceutical compositions suitable for administration. Such compositions typically comprise the pepducin and a pharmaceutically acceptable carrier.

A pharmaceutical composition of the invention is formulated to be compatible with its intended route of administration. Examples of routes of administration include parenteral, e.g., intravenous (e.g., a peripheral vein, such as found in the extremities), intraperitoneal, intradermal, subcutaneous, subdermal, oral, intranasal, aerosol (e.g., inhalation), transdermal (i.e., topical), transmucosal, vaginal, intrauterine, and rectal (e.g., suppositories) administration. Injectable solutions containing active compounds of the present invention may be administered to the vascular lumen of vessels (e.g., aorta or jugular vein). Alternatively, active compounds of the present invention may be administered via a device, e.g., stent or catheter, impregnated or coated with the active compounds.

Solutions or suspensions used for administration (e.g., parenteral) may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. A preparation of a pharmaceutical composition of the present invention can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation or intranasal administration, the compounds are delivered in the form of an aerosol spray from pressured container or dispenser which contains a suitable propellant, e.g., a gas such as carbon dioxide, or a nebulizer (e.g., delivery to the lung).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can also be prepared in the form of suppositories (e.g., with conventional suppository bases such as cocoa butter and other glycerides), a suppository coating, or retention enemas for rectal delivery. The active compounds can be similarly prepared for intravaginal or intrauterine administration. The active compounds may also be administered as impregnated in or as a coating on wound packing (e.g., to reduce bleeding).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pepducins and GPCR peptides can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

Controlled release of active compounds can utilize various technologies. Devices, e.g., stents or catheters, are known having a monolithic layer or a coating incorporating a heterogeneous solution and/or dispersion of an active agent in a polymeric substance, where the diffusion of a therapeutic agent is rate limiting, as the agent diffuses through the polymer to the polymer-fluid interface and is released into the surrounding fluid. Active compound may be dissolved or dispersed in a suitable polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically may have the active compounds physically immobilized in the polymer. The active compounds can be dissolved and/or dispersed throughout the polymeric material. The polymeric material may be hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The pharmaceutical compositions can be included in a container, pack, or dispenser together with instructions for administration.

The pepducin approach according to the present invention allows the rich diversity of intracellular receptor structures to be exploited both for generation of new therapeutic agents and for delineation of the mechanisms of receptor-G protein coupling under in vivo conditions. The pepducins discovered by this strategy may also prove to be more selective to the extent that the pepducins primarily target the receptor rather than the G protein. In addition, many receptors have been identified by genomic and genetic approaches as being important in various diseases processes but have no known ligands—so-called orphan receptors. Pepducin agonists and antagonists can be generated which are tailored to these receptors, and may be useful in determining which signaling pathways are activated by the orphan receptor in the context of its native environment. Thus, in the post-genomic era, the pepducin approach may be widely applicable to the targeting of membrane proteins and may open up new experimental avenues in systems previously not amenable to traditional molecular techniques The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition, an appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, a suitable dosage level is about 0.001 to 10 mg/kg per day, preferably about 0.005 to 5 mg/kg per day, and especially about 0.01 to 1 mg/kg per day.

For example, in patients with acute myocardial infarction, a suitable pepducin (e.g., x1/2pal-i1) may be administered i.v. immediately as a bolus dose, followed by additional i.v. injections once or twice daily for 2-3 days post MI. The dosage may be around 0.1-0.5 mg/kg.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifingal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of formula (I) such as the compounds quaternized by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for examples the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Screening and Detection Methods

The composition of the invention can be used to screen drugs or compounds that modulate GPCR activity or expression as well as to treat disorders characterized by insufficient or excessive production of GPCR protein or production of GPCR protein forms that have decreased or aberrant activity compared to GPCR wild-type protein.

The invention provides a method (also referred to herein as a "screening assay") for identifying modulators, i.e., candidate or test compounds or agents (e.g., peptides, peptidomimetics, small molecules or other drugs) that bind to GPCRs or have a stimulatory or inhibitory effect on, e.g., GPCR protein expression or GPCR activity. The invention also includes compounds identified in the screening assays described herein.

The invention provides assays for screening candidate or test compounds which bind to or modulate the activity of the membrane-bound form of a pepducin-GPCR complex or biologically-active portion thereof. The test compounds of the invention can be obtained using any of the numerous approaches in combinatorial library methods known in the art, including for example, biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, nonpeptide oligomer or small molecule libraries of compounds. See, e.g., Lam, 1997. *Anticancer Drug Design* 12: 145.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (e.g., Houghten, 1992. Biotechniques 13: 412-421), or on beads (Lam, 1991. Nature 354: 82-84), on chips (Fodor, 1993. Nature 364: 555-556), bacteria (Ladner, U.S. Pat. No. 5,223, 409), spores (Ladner, U.S. Pat. No. 5,233,409), plasmids (Cull, et al., 1992. Proc. Natl. Acad. Sci. USA 89: 1865-1869) or on phage (Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; Ladner, U.S. Pat. No. 5,233,409).

An assay is a cell-based assay in which a cell which expresses a membrane-bound form of a GPCR, or a biologically-active portion thereof on the cell surface, plus a pepducin, is contacted with a test compound and the ability of the test compound to bind to the GPCR and displace the pepducin determined. The test compound could bind at the extracellular surface, transmembrane domains, or intracellular surfaces of the GPCR target and inhibit or enhance the pepducin activation of the GPCR. The cell, for example, is of mammalian origin or a yeast cell. Determining the ability of the test compound to displace the pepducin from the GPCR protein can be accomplished, for example, by coupling the pepducin to a radioisotope or enzymatic label such that binding of the test compound displaces the pepducin from the GPCR or biologically-active portion thereof. Alternatively, the test compounds can be labeled with $^{125}I$, $^{35}S$, $^{14}C$, or $^{3}H$, either directly or indirectly, and the pepducin could displace the radio-labeled test compound from the GPCR and the free radio-labeled test compound detected by direct counting of radioemission or by scintillation counting. Alternatively, test compounds can be enzymatically-labeled with, for example, horseradish peroxidase, alkaline phosphatase, or luciferase, and the enzymatic label detected by increases or decreases in conversion of an appropriate substrate to product upon addition of pepducin.

In another embodiment, an assay is a cell-based assay comprising contacting a cell expressing a membrane-bound form of GPCR protein, or a biologically-active portion thereof, on the cell surface with a test compound and determining the ability of the test compound to modulate (e.g., stimulate or inhibit) the binding, activity of the pepducin for the GPCR.

Determining the ability of the test molecule to interact with a GPCR target molecule can be accomplished by one of the methods described above for determining direct binding. In one embodiment, determining the ability of the test molecule to inhibit the GPCR peptide interaction with a GPCR target molecule can be accomplished by determining the activity of the target GCPR-pepducin complex. For example, the activity of the target molecule can be determined by inhibiting GPCR-peptide induction of a cellular second messenger of the GPCR target (i.e. intracellular $Ca^{2+}$, diacylglycerol, $IP_3$, etc.), detecting catalytic/enzymatic activity dependent on GPCR activation or inhibition, detecting the induction or inhibition of a reporter gene (comprising a GPCR-responsive regulatory element operatively linked to a nucleic acid encoding a detectable marker, e.g., luciferase), or detecting a cellular response, for example, cell survival, cellular differentiation, or cell proliferation.

Alternatively, an assay of the invention is a cell-free assay comprising contacting a GPCR peptide or biologically-active portion thereof with a test compound and determining the ability of the test compound to bind or modulate (e.g. stimulate or inhibit) the activity of the GPCR protein or biologically-active portion thereof.

Binding of the test compound to the GPCR can be determined either directly or indirectly as described above. For example, the assay comprises contacting the pepducin plus the GPCR or biologically-active portion thereof with a known compound which binds GPCR to form an assay mixture, contacting the assay mixture with a test compound, and determining the ability of the test compound to interact with a GPCR protein, wherein determining the ability of the test compound to interact with a GPCR protein comprises determining the ability of the test compound to preferentially bind to GPCR or biologically-active portion thereof as compared to the known compound.

Determining the ability of the test compound to modulate the activity of GPCR can be accomplished, for example, by determining the ability of the GPCR peptide to bind to a GPCR target molecule by one of the methods described above for determining direct binding. Alternatively, determining the ability of the test compound to modulate the activity of GPCR peptide can be accomplished by determining the ability of the GPCR peptide to further modulate a GPCR target molecule. For example, the catalytic/enzymatic activity of the target molecule on an appropriate substrate can be determined as described above.

The cell-free assay comprises contacting the GPCR peptide or biologically-active portion thereof with a known compound which binds the GPCR to form an assay mixture, contacting the assay mixture with a test compound, and determining the ability of the test compound to interact with a GPCR, wherein determining the ability of the test compound to interact with a GPCR comprises determining the ability of the GPCR peptide to preferentially bind to or modulate the activity of a GPCR target molecule.

The cell-free assays of the invention are amenable to use of both the soluble form or the membrane-bound form of GPCR protein. In the case of cell-free assays comprising the membrane-bound form of GPCR protein, it may be desirable to utilize a solubilizing agent such that the membrane-bound form of GPCR protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

It may be desirable to immobilize either GPCR peptide or its target molecule to facilitate separation of complexed from uncomplexed forms of one or both of the proteins, as well as to accommodate automation of the assay. Binding of a test compound to GPCR protein, or interaction of GPCR protein with a pepducin in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-GPCR fusion peptides or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or GPCR peptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, vide supra. Alternatively, the complexes can be dissociated from the matrix, and the level of GPCR peptide binding or activity determined using standard techniques.

Other techniques for immobilizing proteins on matrices are also used in the screening assays of the invention. For example, either the GPCR peptide or its target molecule can be immobilized utilizing conjugation of biotin and streptavidin. Biotinylated GPCR peptide or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with GPCR peptide or target molecules, but which do not interfere with binding of the GPCR peptide to its cognate GPCR, can be derivatized to the wells of the plate, and unbound target or GPCR peptide trapped in the wells by antibody conjugation. Methods for detecting such complexes, in addition to those described above for the GST-immobilized complexes, include immunodetection of complexes using antibodies reactive with the GPCR peptide or target molecule, as well as enzyme-linked assays that rely on detecting an enzymatic activity associated with the GPCR peptide or target molecule.

Modulators of GPCR protein expression are identified in a method wherein a cell is contacted with a candidate compound and the expression of GPCR mRNA or protein in the cell is determined. The level of expression of GPCR mRNA or protein in the presence of the candidate compound is compared to the level of expression of GPCR mRNA or protein in the absence of the candidate compound. The candidate compound can then be identified as a modulator of GPCR mRNA or protein expression based upon this comparison. For example, when expression of GPCR mRNA or protein is greater (i.e., statistically significantly greater) in the presence of the candidate compound than in its absence, the candidate compound is identified as a stimulator of GPCR mRNA or protein expression. Alternatively, when expression of GPCR mRNA or protein is less (statistically significantly less) in the presence of the candidate compound than in its absence, the candidate compound is identified as an inhibitor of GPCR mRNA or protein expression. The level of GPCR mRNA or protein expression in the cells can be determined by methods described herein for detecting GPCR mRNA or protein.

The peptide sequences discussed herein are presented in the following Table 3.

TABLE 3

| SEQ ID NO: | SEQUENCE | Name/Identifier |
|---|---|---|
| 1 | KYVVIIAYALVFLLSLLGNSLVMLVILYSRVGRSVTD VYLLNLALADLLFALTLPIWAASK | CXCR1_HUMAN |
| 2 | KYVVIITYALVFLLSLLGNSLVMLVILYSRVGRSVTD VYLLNLALADLLFALTLPIWAASK | CXCR1_PANTR |
| 3 | KYVVIITYALAFLLSLLGNSLVMLVILYSRGGRSVTD VYLLNLALADLLFALTLPIWAASK | CXCR1_GORGO |
| 4 | KYVVVVIYALVFLLSLLGNSLVMLVILYSRSNRSVTD VYLLNLAMADLLFALTMPIWAVSK | CXCR1_RABBIT |
| 5 | RQAVVVFYALVFLLSLLGNSLVMLVILYRRRTRSVTD VYVLNLAIADLLFSLTLPFLAVSK | CXCR1_RAT |
| 6 | KYFVVIIYALVFLLSLLGNSLVMLVILYSRVGRSVTD VYLLNLALADLLFALTLPIWAASK | CXCR2_HUMAN |
| 7 | SYAVVVIYVLVTLLSLVGNSLVMLVILYNRSTCSVTD VYLLNLAIADLFFALTLPVWAASK | CXCR2_MOUSE |
| 8 | KYFVVIIYALVFLLSLLGNSLVMLVILYSRVGRSVTD VYLLNLALADLLFALTLPIWAASK | CXCR2_PANTR |
| 9 | KYFVVIIYALVFLLSLLGNSLVMLVILYSRVGRSVTD VYLLNLALADLLFALTLPIWAASK | CXCR2_MACMU |
| 10 | KYFVVIIYALVFLLSLLGNSLVILVILYSRVGRSVTD VYLLNLALADLLFALTLPIWAASK | CXCR2_GORGO |
| 11 | SYVVLITYTLVFLLSLLGNSLVMLVILYSRSTCSVTD VYLLNLAIADLLFATTLPTWAASK | CXCR2_RABBIT |
| 12 | KYAVVVIYVLVFVLNLLGNSLVIMVVLYSRVSHSVTD VYLLNLAIADLLFALTLPIWAVSK | CXCR2_CANFA |
| 13 | KYAVVVIDALVFLLSLLGNSLVMLVILYSRIGRSVTD VYLLNLAMADLLFAMTLPIWTASK | CXCR2_BOVIN |

TABLE 3-continued

| SEQ ID NO: | SEQUENCE | Name/Identifier |
|---|---|---|
| 14 | RYAVVVIYVLVTLLSLVGNSLVMLVILYNRSTCSVTD VYLLNLAIADLFFALTLPVWAASK | CXCR2_RAT |
| 15 | MEGISIYTSD NYTEEMGSGD YDSMKEPCFR EENANFNKIF LPTIYSIIFL TGIVGNGLVI LVMGYQKKLR SMTDKYRLHL SVADLLFVIT LPFWAVDAVA NWYFGNFLCK AVHVIYTVNL YSSVLILAFI SLDRYLAIVH ATNSQRPRKL LAEKVVYVGV WIPALLLTIP DFIFANVSEA DDRYICDRFY PNDLWVVVFQ FQHIMVGLIL PGIVILSCYC IIISKLSHSK GHQKRKALKT TVILILAFFA CWLPYYIGIS IDSFILLEII KQGCEFENTV HKWISITEAL AFFHCCLNPI LYAFLGAKFK TSAQHALTSV SRGSSLKILS KGKRGGHSSV STESESSSFH SS | CXCR4 receptor |
| 16 | IFLPTIYSIIFLTGIVGNGLVILV | CXCR4 TM1 |
| 17 | FLFRTKKKHPAV | PAR2 |
| 18 | ILYSRVGRSVTD | CXCR1 |
| 19 | YSRVGRSVTD | CXCR1 |
| 20 | YSRVGRSVTD | CXCR1 |
| 21 | ILYSRVGRSVTD | CXCR2 |
| 22 | YSRVGRSVTD | CXCR2 |
| 23 | YSRVGRSVTD | CXCR2 |
| 24 | YQKKLRSMTD | CXCR4 |
| 25 | MGYQKKLRSMTD | CXCR4 |
| 26 | KRLKSMTD | CCR5 |
| 27 | LINCKRLKSMTD | CCR5 |
| 28 | ILKMKVKKPAV | PAR1 |
| 29 | VLATQAPRLPST | PAR4 |
| 30 | ATQAPRLPST | PAR4 |
| 31 | VLATGAPRLPST | PAR4 |
| 32 | ATGAPRLPST | PAR4 |
| 33 | TFLLRN | |
| 34 | AYPGKF | |
| 35 | SFLLRN | |
| 36 | NKIFLPTIYSIIFLTGIVGNGLVILVMGYQKKLRSMT DKYRLHLSVADLLFVITLPFWAVD | CXCR4_HUMAN |
| 37 | NRIFLPTIYFIIFLTGIVGNGLVILVMGYQKKLRSMT DKYRLHLSVADLLFVITLPFWAVD | CXCR4_MOUSE |
| 38 | NRIFLPTIYSIIFLTGIVGNGLVILVMGYQKKLRSMT DKYRLHLSVADLLFVITLPFWAVD | CXCR4 PAPAN |
| 39 | NRIFLPTIYSIIFLTGIVGNGLVILVMGYQKKLRSMT DKYRLHLSVADLLFVITLPFWAVD | CXCR4_MACMU |
| 40 | NKIFLPTIYSIIFLTGIVGNGLVILVMGYQKKLRSMT DKYRLHLSVADLLFVITLPFWAVD | CXCR4_PANTR |
| 41 | NRIFLPTVYSIIFLTGIVGNGLVILVMGYQKKLRSMT DKYRLHLSVADLLFVLTLPFWAVD | CXCR4_FELCA |
| 42 | NRIFLPTVYSIIFLTGIVGNGLVILVMGYQKKLRSMT DKYRLHLSVADLLFVLTLPFWAVD | CXCR4_BOVIN |

TABLE 3-continued

| SEQ ID NO: | SEQUENCE | Name/Identifier |
|---|---|---|
| 43 | NRIFLPTIYFIIFLTGIVGNGLVILVMGYQKKLRSMT DKYRLHLSVADLLFVITLPFWAVD | CXCR4_RAT |
| 44 | PPLYSLVFVIGLVGNTLVVLVLVQYKRLKNMTSIYLL NLAISDLLFLTLP | CCR1_HUMAN |
| 45 | PPLYSLVFIIGVVGNVLMILVLMQHRRLQSMTSTYLF NLAVSDLVFLFTLP | CCR1_MOUSE |
| 46 | PPLYSLVFVIGVVGNLLVVLVLVQYKRLKNMTNIYLL NLAISDLLFLFTLP | CCR1_MACMU |
| 47 | PPLYSLVFIFGFVGNMLVVLILINCKKLKCLTDIYLL NLAISDLLFLITLPLWAHSAANE | CCR2_HUMAN |
| 48 | PPLYSLVFIFGFVGNMLVIIILIGCKKLKSMTDIYLL NLAISDLLFLLTLPFWAHYAANE | CCR2_MOUSE |
| 49 | PPLYSLVFIFGFVGNMLVIIILISCKKLKSMTDIYLF NLAISDLLFLLTLPFWAHYAANE | CCR2_RAT |
| 50 | PPLYSLVFIFGFVGNMLVVLILINCKKLKSLTDIYLL NLAISDLLFLITLPLWAHSAANE | CCR2_MACMU |
| 51 | PPLYSLVFVFGLLGNSVVVLVLFKYKRLRSMTDVYLL NLAISDLLFVFSLPFWG | CCR4_HUMAN |
| 52 | PPLYSLVFLLGLFGNSVVVLVLFKYKRLKSMTDVYLL NLAISDLLFVLSLPFWG | CCR4_MOUSE |
| 53 | PPLYSLVFIFGFVGNMLVILI<u>LINCKRLKSMTD</u>IYLL NLAISDLFFL | CCR5_HUMAN |
| 54 | PPLYSLVFIFGFVGNMMVFLILISCKKLKSVTDIYLL NLAISDLLFL | CCR5_MOUSE |
| 55 | PPLYSLVFIFGFVGNILVVLILINCKRLKSMTDIYLL NLAISDLLFL | CCR5_PAPHA |
| 56 | PPLYSLVFIFGFVGNILVVLILINCKRLKSMTDIYLL NLAISDLLFL | CCR5_LOPAT |
| 57 | PPLYSLVFIFGFVGNILVVLILINCKRLKSMTDIYLL NLAISDLLFL | CCR5_MACMU |
| 58 | PPLYSLVFIFGFVGNILVVLILINCKRLKSMTDIYLL NLAISDLLFL | CCR5_MACNE |
| 59 | PPLYSLVFIFGFVGNILVVLILINCKRLKSMTDIYLL NLAISDLLFL | CCR5_MACFA |
| 60 | PPLYSLVFIFGFVGNMLVILILINCKRLKSMTDIYLL NLAISDLFFL | CCR5_PANTR |
| 61 | PPLYSLVFIFGFVGNMLVILILINCKRLKSMTDIYLL NLAISDLFFL | CCR5_GORGO |
| 62 | PPLYSLVFIFGFVGNMNVFLILISCKKLKSMTDIYLF NLAISDLLFL | CCR5_RAT |
| 63 | FVPSVYTGVFVVSLPLNIMAIVVFILKMKVKKPAVVY MLHLATADVLFVSVLPFK | PAR1_HUMAN |
| 64 | FMPSVYTIVFIVSLPLNVLAIAVFVLRMKVKKPAVVY MLHLAMADVLFVSVLPFK | PAR1_MOUSE |
| 65 | FIPSVYTFVFIVSLPLNILAIAVFVFRMKVKKPAVVY MLHLAMADVLFVSVLPFK | PAR1_RAT |
| 66 | FIPSVYTFVFVVSLPLNILAIAVFVLKMKVKKPAVVY MLHLAMADVLFVSVLPLK | PAR1_CRILO |
| 67 | FVPSVYTGVFVVSLPVNIMAIVVFILKMKVKKPAVVY MLHLATADVLFVSVLPFK | PAR1_PAPHA |

TABLE 3-continued

| SEQ ID NO: | SEQUENCE | Name/Identifier |
|---|---|---|
| 68 | FVPSLYTVVFIVGLPLNLLAIIIFLFKMKVRKPAVVY MLNLAIADVFFVSVLPFK | PAR1_XENLA |
| 69 | FLPIVYTIVFVVGLPSNGMALWVFLFRTKKKHPAVIY MANLALADLLSVIWFPLK | PAR2_HUMAN |
| 70 | FLPVVYIIVFVIGLPSNGMALWIFLFRTKKKHPAVIY MANLALADLLSVIWFPLK | PAR2_MOUSE |
| 71 | FLPVIYIIVFVIGLPSNGMALWVFFFRTKKKHPAVIY MANLALADLLSVIWFPLK | PAR2_RAT |
| 72 | LIPAIYLLVFVVGVPANAVTLWMLFFRTRSICTTV.F YTNLAIADFLFCVTLPFK | PAR3_HUMAN |
| 73 | VIPATYILLFVVGVPSNIVTLWKLSLRTKSISL.VIF HTNLAIADLLFCVTLPFK | PAR3_MOUSE |
| 74 | VIPAIYILVFVIGVPANIVTLWKLSSRTKSICL.VIF HTNLAIADLLFCVTLPFK | PAR3_RAT |
| 75 | LVPALYGLVLVVGLPANGLALWVLATQAPRL.PSTML LMNLATADLLLALALPPR | PAR4_HUMAN |
| 76 | LVPALYGLVVAVGLPANGLALWVLATRVPRL.PSTIL LTNLAVADSLLALVPPPR | PAR4_MOUSE |
| 77 | LVPAIYGLVVVVGLPANGLALWVLATRVPRL.PSTIL LMNLAVADLLLALVLPPR | PAR4_RAT |
| 78 | KLTSVVFILICCFIILENIFVLLTIWKTKKFHRPMYY FIGNLALSDLLAG | EDG1_HUMAN |
| 79 | KLTSVVFILICCFIILENIFVLLTIWKTKKFHRPMYY FIGNLALSDLLAG | EDG1_MOUSE |
| 80 | KLTSVVFILICCLIILENIFVLLTIWKTKKFHRPMYY FIGNLALSDLLAG | EDG1_RAT |
| 81 | KLVMGLGITVCIFIMLANLLVMVAIYVNRRFHFPIYY LMANLAAADFFAG | EDG2_HUMAN |
| 82 | KLVMGLGITVCVFIMLANLLVMVAIYVNRRFHFPIYY LMANLAAADFFAG | EDG2_MOUSE |
| 83 | KLVMGLGITVCIFIMLANLLVMVAIYVNRRFHFPIYY LMANLAAADFFAG | EDG2_SHEEP |
| 84 | KLVMGLGITVCIFIMLANLLVMVAIYVNRRFHFPIYY LMANLAAADFFAG | EDG2_BOVIN |
| 85 | TLTTVLFLVICSFIVLENLMVLIAIWKNNKFHNRMYF FIGNLALCDLLAG | EDG3_HUMAN |
| 86 | LITTILFLVTCSFIVLENLMVLIAIWKNNKFHNRMYF FIGNLALCDLLAG | EDG3_MOUSE |
| 87 | DPKTIAFLVVCSFIILENLTVLLAIWKNHRFHNRMYF FIGNLALCDLLAS | EDG3_FUGRU |
| 88 | VVVVALGLTVSVLVLLTNLLVIAAIASNRRFHQPIYY LLGNLAAADLFAG | EDG4_HUMAN |
| 89 | VVVVALGLTVSVLVLLTNLLVIAAIASNRRFHQPIYY LLGNLAAADLFAG | EDG4_MOUSE |
| 90 | VVVVALGLTVSVLVLLTNLLVIAAIASNRRFHQPIYY LLGNLAAADLFAG | EDG4_MACFA |
| 91 | QVASAFIVILCCAIVVENLLVLIAVARNSKFHSAMYL FLGNLAASDLLAG | EDG5_HUMAN |
| 92 | KVASAFIIILCCAIVVENLLVLIAVARNSKFHSAMYL FLGNLAASDLLAG | EDG5_MOUSE |

TABLE 3-continued

| SEQ ID NO: | SEQUENCE | Name/Identifier |
|---|---|---|
| 93 | KVASAFIIILCCAIVVENLLVLIAVARNSKFHSAMYL FLGNLAASDLLAG | EDG5_RAT |
| 94 | GALRGLSVAASCLVVLENLLVLAAITSHMRSRRWVYY CLVNITLSDLLTG | EDG6_HUMAN |
| 95 | GMLRGPSVAAGCLVVLENAMVLAAIAIYMRSRRWVYY CLLNITLSDLLTG | EDG6_MOUSE |
| 96 | SSLNILFVVICSIIILENLLVLIAVFRNKKFHSAMFF FIGNLAFSDLLAG | EDG5_BRARE |
| 97 | VIVLCVGTFFCLFIFFSNSLVIAAVIKNRKFHFPFYY LLANLAAADFFAG | EDG7_HUMAN |
| 98 | VIVLCVGTFFCLFIFFSNSLVIAAVITNRKFHFPFYY LLANLAAADFFAG | EDG7_MOUSE |
| 99 | VIVLCVGTFFCLFIFFSNSLVIAAVITNRKFHFPFYY LLANLAAADFFAG | EDG7_RAT |
| 100 | WQIVLWAAAYTVIVVTSVVGNVVVMWIILAHKRMRTV TNYFLVNLAFAEAS | NK1R_HUMAN |
| 101 | WQIVLWAAAYTVIVVTSVVGNVVVIWIILAHKRMRTV TNYFLVNLAFAEAC | NK1R_MOUSE |
| 102 | WQIVLWAAAYTVIVVTSVVGNVVVIWIILAHKRMRTV TNYFLVNLAFAEAC | NK1R_RAT |
| 103 | WQIVLWAAAYTVIVVTSVVGNVVVMWIILAHKRMRTV TNYFLVNLAFAEAS | NK1R_CAVPO |
| 104 | WQIALWSVAYSIIVIVSLVGNTIVMWIIAHKRMRTV TNYFLVNLAFAEAS | NK1R_RANCA |

The peptidic portion of the pepducin, e.g., from the i1 loop, may be any suitable length that results in the intended beneficial effects, generally 5 to 15, or, e.g., 5, 6, 7, 8, 9, 10, 11, 12, 13, 14, 15, 16, 17, 18, 19, 20, 21, 22, 23, 24, 25, 26, 27, 28, 29 or 30.

Methods for preparing pepducin compounds of the invention are illustrated in the following synthetic schemes and example(s). The following schemes, examples and biological data are given for the purpose of illustrating the invention, but not for limiting the scope or spirit of the invention.

Manufacture and Characterization of Pepducin Compositions

Synthesis by standard Fmoc solid phase synthetic methods and preparation of palmitoylated pepducin peptides was performed as generally described in Covic et al. PNAS 99:643-648 (2002). Pepducins were purified to >95% purity by $C_{18}$ or $C_4$ reverse phase chromatography and dissolved in DMSO.

Bleeding times were performed with 6-8 week-old adult male CF-1 mice anaesthetized with an intraperitoneal injection of xylazine (10 mg/kg) plus ketamine (50 mg/kg). The internal jugular vein was cannulated with a 0.28×1.52 mm gauge catheter and P1pal-12 (3 µmoles/L), P4pal-10 (3 µmoles/L) or vehicle alone (DMSO), was infused over 1 min in a total volume of 100 µL. Experiments were performed blind to injected substance. After 5 min, tails were amputated 2 mm from the tail tip. Tails were immersed in a beaker of phosphate-buffered saline maintained at 37° C. and bleeding was visually followed and timed. If bleeding restarted within 5 min, it was recorded as a re-bleed and taken to mark an unstable hemostasis event as previously described. Law et al., Nature 401, 808 (1999). Maximum bleeding time allowed was 10 min after which the tail was cauterized.

EXAMPLE 1

Figure 5:
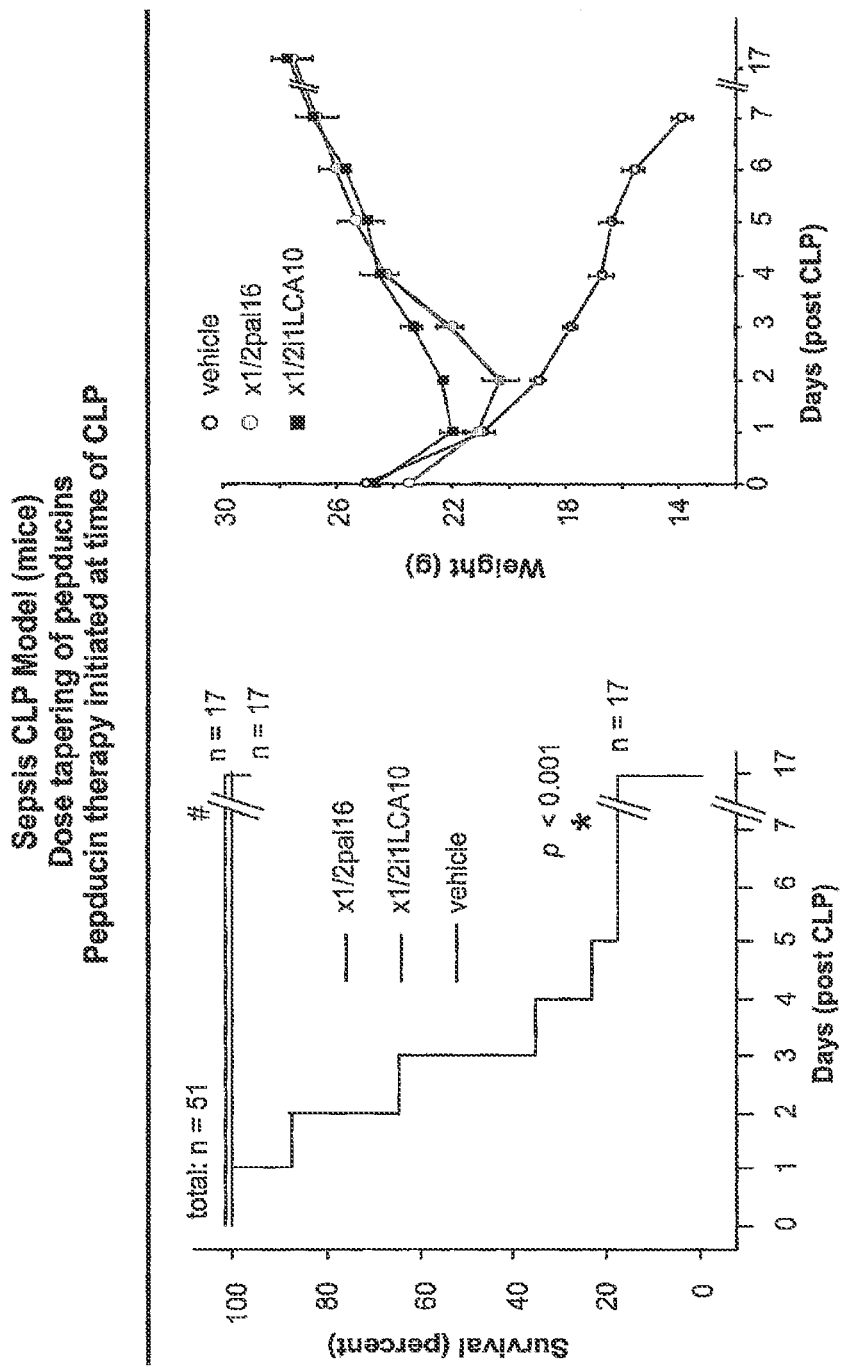
FIG. 5 is a line graph showing the animal response to pepducin therapy at the time of CLP in an experiment detailed in Example 1.

To demonstrate how sepsis may be effectively treated by pepducins of the present invention, 6 to 8 week old female CF-1 mice were treated with a 2.5 mg/kg pepducin preparation in 20% DMSO, or vehicle (20% DMSO). The time point selected for treatment is at the induction of non-lethal sepsis by cecal ligation and puncture (CLP). After an initial dose of 2.5 mg/kg, 1 mg/kg pepducin (or vehicle) was injected into the mice subcutaneously each day for six days. *: Four mice out of the vehicle-treated group were sacrificed after six days; #: one mouse out of the groups treated with x1/2i1LCA10 pepducin was sacrificed on day 6, and all remaining surviving mice were sacrificed at 17 days. FIG. 5 shows the results. In the left panel, mice were treated with x1/2pal16, x1/2i1LCA10 or vehicle (20% DMSO) at the time point of CLP. In the right panel, mice were monitored for body weight every day. Vehicle-treated mice showed severe weight loss, whereas pepducin-treated mice gained weight after an initial weight loss.

EXAMPLE 2

Figure 6:
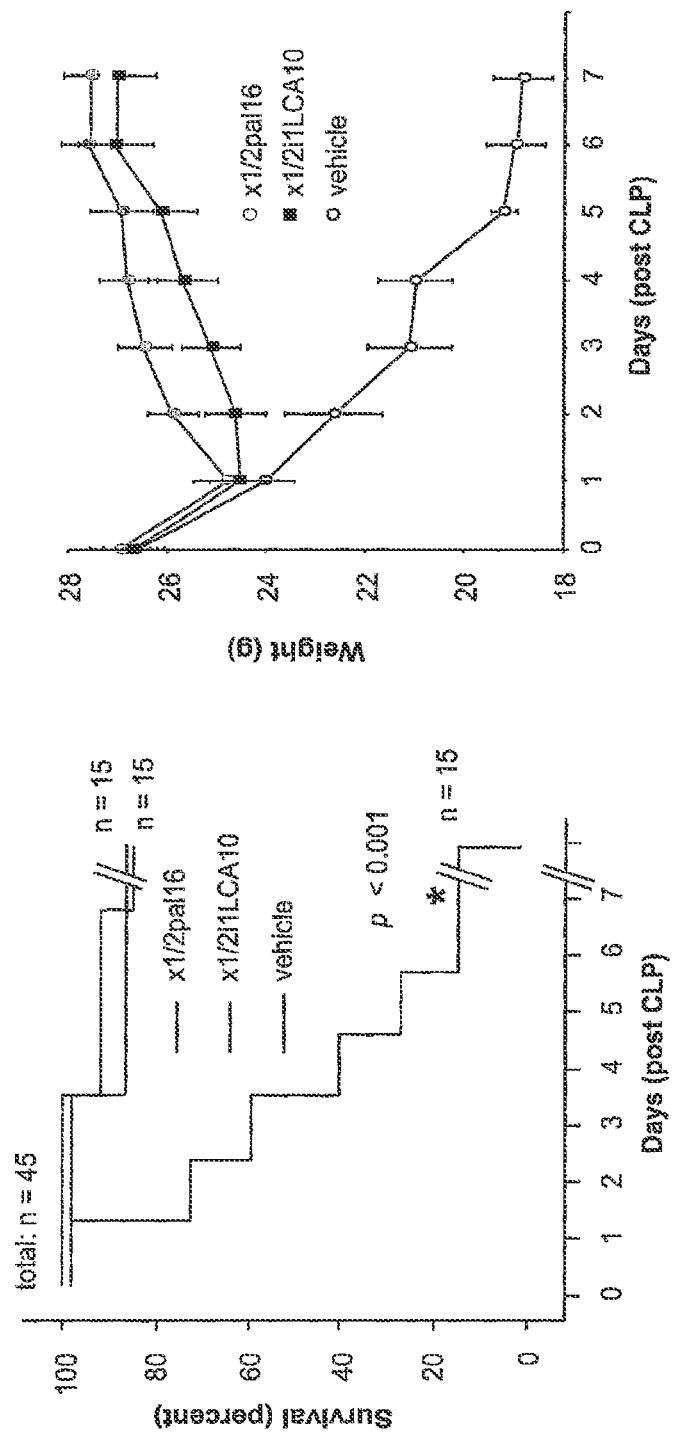
FIG. 6 is a line graph showing the results of an experiment detailed in Example 2, showing the results of pepducin therapy initiated eight hours after CLP.

There are only few reports where treatment of sepsis is sufficient, even after the onset of systemic inflammatory response syndrome. To demonstrate that sepsis may be effectively treated by pepducins of the present invention well after initiating sepsis, mice were treated with a 5.0 mg/kg pepducin preparation in 40% DMSO, or vehicle (40% DMSO). The time point selected for treatment is eight hours at the induction of non-lethal sepsis by cecal ligation and puncture (CLP). After an initial dose of 5.0 mg/kg, 2.5 mg/kg pepducin (or vehicle) was injected into the mice subcutaneously each day from day 2 to day 3, and 1.0 mg/kg from day 3 to day 6. Eight hours after CLP, the mice already showed signs of systemic illness characteristic of sepsis, e.g., ruffled fur, decreased mobility, decreased food and water intake, and closed, inflamed eyes. FIG. 6 shows the results. In the left panel, *: two mice out the vehicle treated group were sacrificed on day 6. Mice that survived the experiment were sacrificed on day 17. In the right panel, mice were monitored for their body weight every day.

EXAMPLE 3

Figure 7:
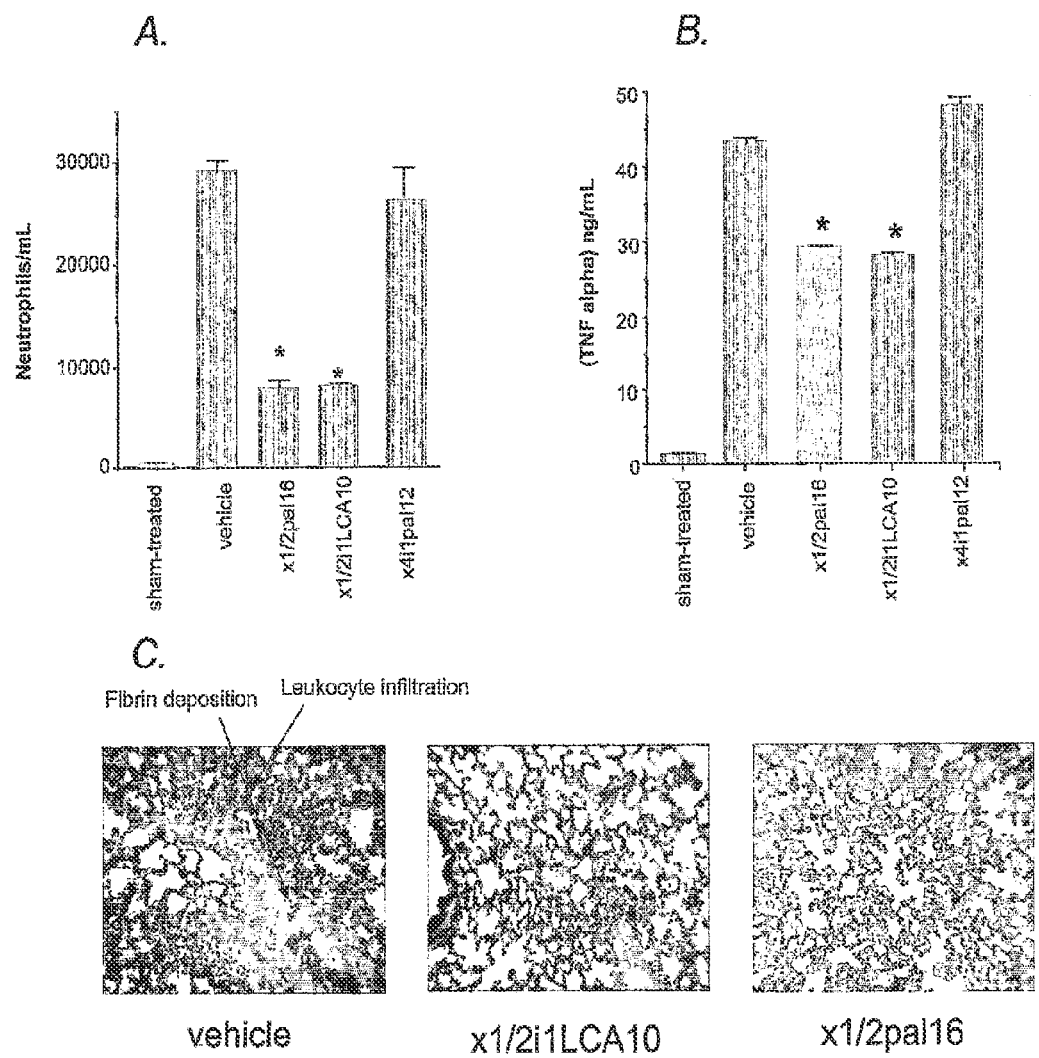
FIGS. 7A-C depict the inhibition of leukocyte infiltration into lung; and TNF-α production and fibrin deposition in lung after pepducin treatment, as detailed further in Example 3.

To demonstrate the utility of pepducin treatment of inflammatory disorders, mice were treated with pepducins of the invention. FIG. 7 shows the results. Adult respiratory response syndrome (ARDS) results from excessive neutrophil infiltration into lungs and their activation, leading to fibrin deposition. Sepsis can cause ARDS, which has a high lethality. Panels A and B: Mice were sacrificed 24 hours after CLP and BAL was performed. Neutrophils were counted after staining with Giemsa, TNF was measured by ELISA. *$p<0.02$ vs. vehicle treated group. C Lung histology. Mice were sacrificed 48 hours after CLP.

EXAMPLE 4

Figure 8:
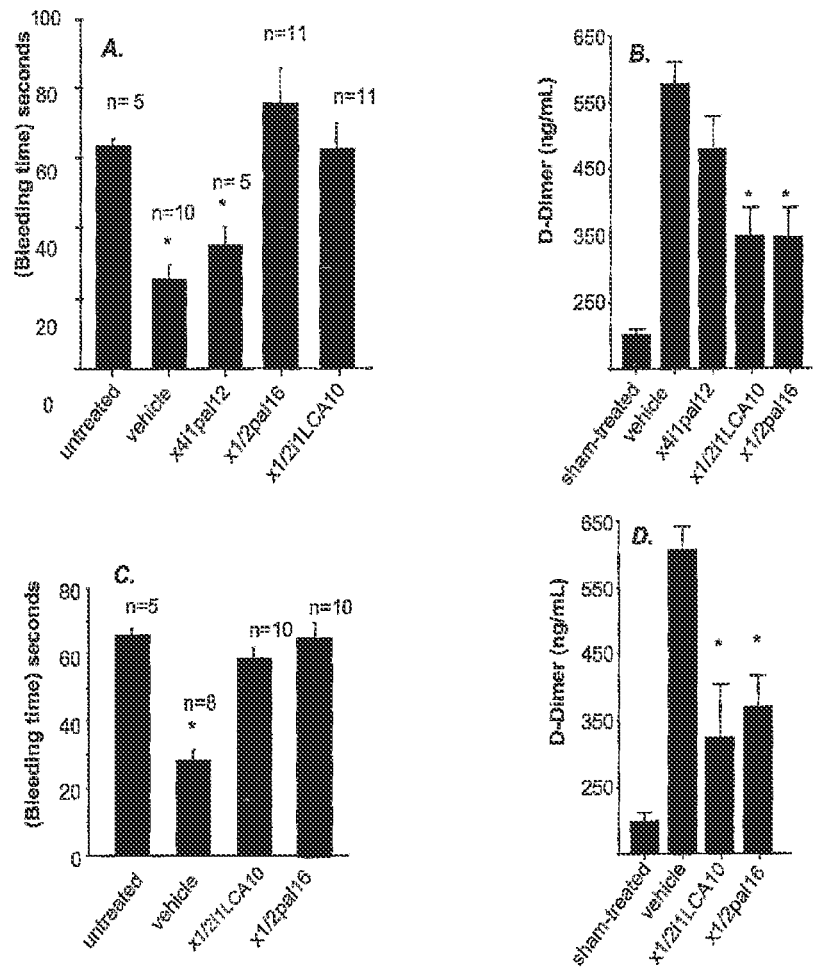
FIGS. 8A-D are bar graphs showing the shortening of bleeding time in septic mice, after pepducin treatment.

This example demonstrates how pepducin treatment may be used to alleviate another aspect of sepsis. Systemic inflammatory responses, the derangement of coagulation and fibrinolysis in DIC is mediated by several pro-inflammatory cytokines. Changes in bleeding time and increases in D-dimer, which is a product of excessive counter-regulatory fibrinolysis, is a hallmark of disseminated intravascular coagulation, leading to widespread deposition of fibrin in the circulation, contributing to multi organ failure and death in septic patients. FIG. 8 shows the results. A. Bleeding time was measured 24 h after CLP and immediate onset of treatment. Bleeding time was shortened in vehicle-treated mice, whereas the i1-loop pepducin x1/2i1LCA10- or the i3 loop pepducin x1/2pal16-treated mice showed normal bleeding times. B. D-dimer levels were measured 48 hours after CLP. As a surrogate marker of the amount of fibrin deposition, D-dimer was increased after CLP, to a higher extent in vehicle-treated mice than in CXCR2 pepducin-treated mice. C. Depicts the bleeding time of mice that were treated 8 h after CLP. D. Depicts the D-dimer levels of mice treated 8 h after CLP.

EXAMPLE 5

Figure 9:
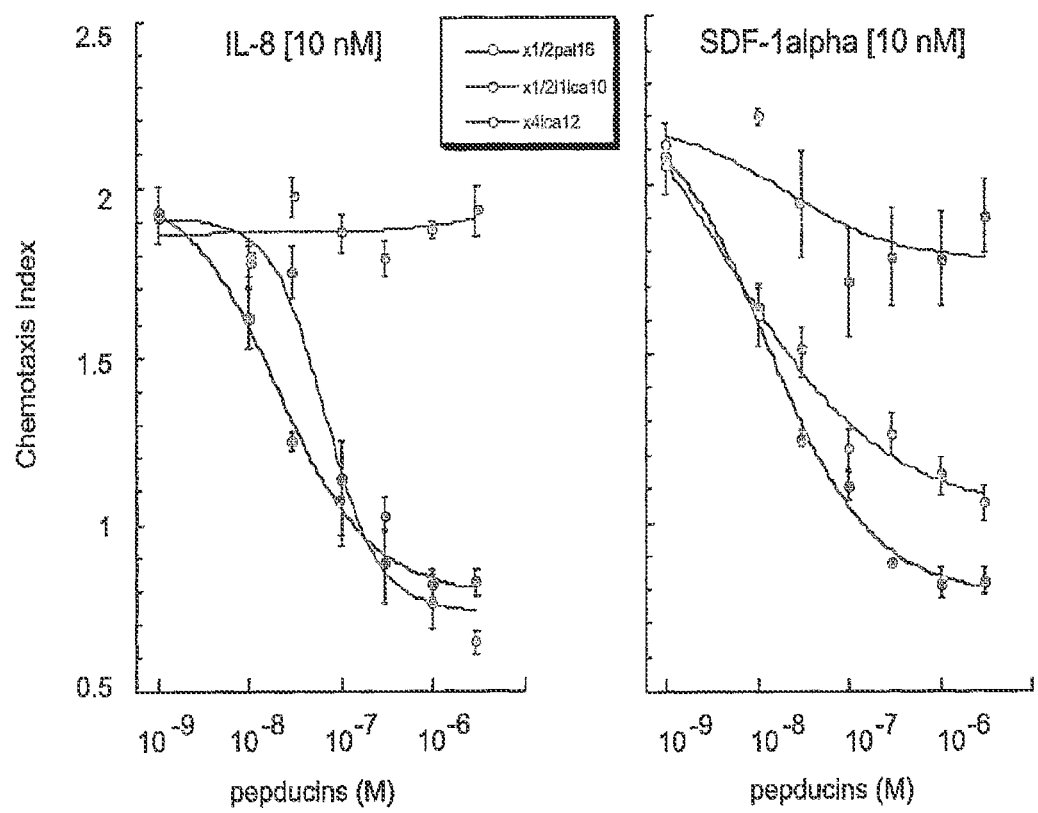
FIG. 9 is a graph showing how human neutrophil chemotaxis is inhibited by pepducin treatment, as shown in more detail in Example 5.

To demonstrate the utility of pepducin treatment of inflammatory disorders, chemotaxis assays were performed in modified 48-well microchemotaxis chambers. 1 mio neutrophils/mL were allowed to migrate toward the chemoattractant in the lower wells. Neutrophils were pretreated with either 0.2% DMSO or the pepducins at the indicate concentrations. N=3. FIG. 9 shows the results.

EXAMPLE 6

Figure 10:
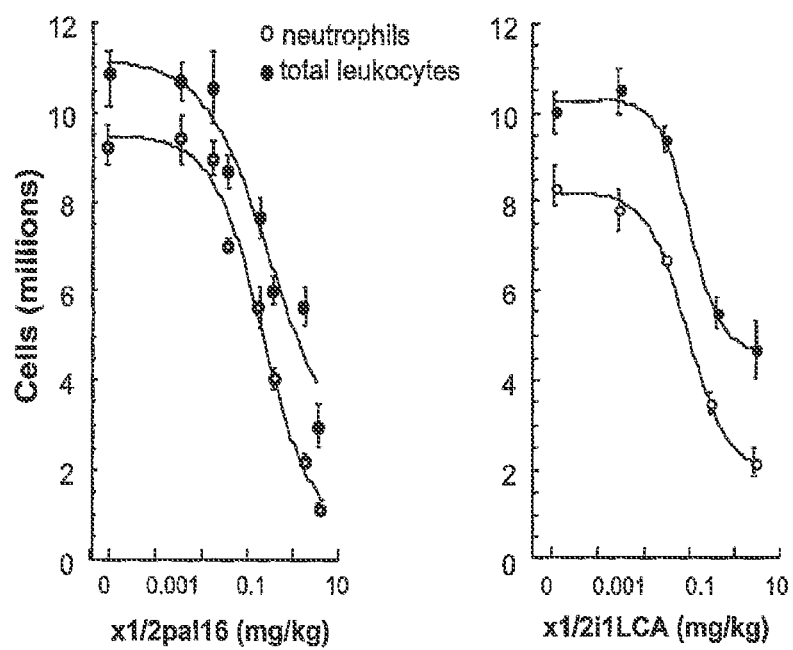
FIG. 10 is a graph showing how leukocyte chemotaxis is inhibited by in vivo pepducin treatment, as shown in more detail in Example 6.

To demonstrate the utility of pepducin treatment of inflammatory disorders in vivo, chemotaxis assays were performed in mice. Mice were injected with 1 mL of 3% thioglycollate i.p. Thioglycollate induces peritoneal macrophages to secret cytokines and leukocytes are then recruited into the peritoneal cavity. Pepducins were injected i.v. at the indicated doses. After 4 hours, cells were collected by peritoneal lavage, stained with Giemsa and counted under 40× magnification. N=60. FIG. 10 shows the results.

EXAMPLE 7

Figure 11:
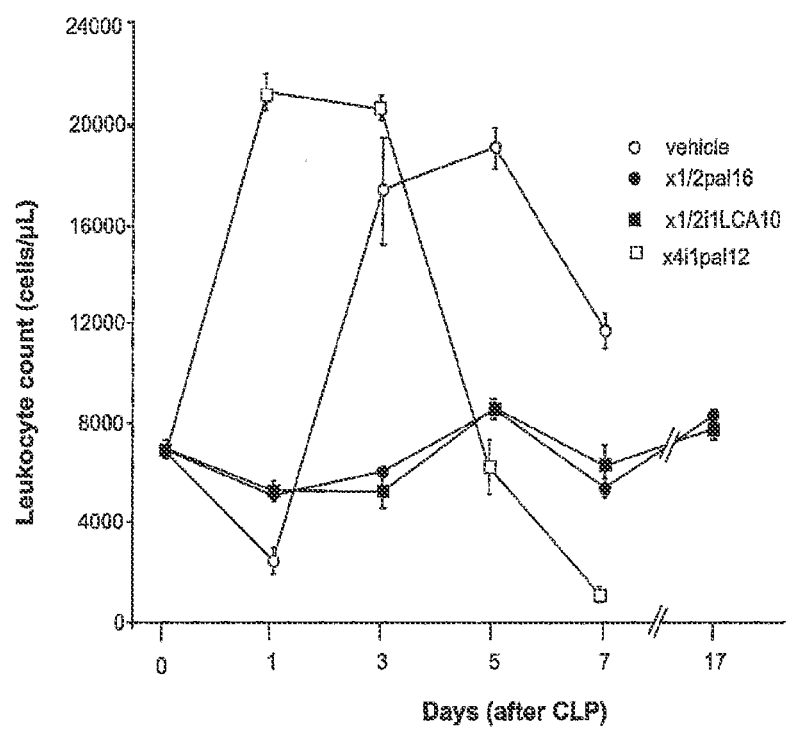
FIG. 11 is a line graph showing the results of an experiment as described in more detail in Example 7.

It has been shown that SDF-1α and CXCR4 are involved in recruiting immature neutrophils from the bone marrow. High levels of CXCR4 expression and activation lead to homing of senescent neutrophils to the bone marrow, whereas chemokines acting on the CXCR2 receptors of neutrophils, i.e., KC, Gro-α or IL-8, lead to increased neutrophil mobilization. Blood was drawn 1, 3, 5, 7 and 17 days after CLP, and leukocytes were counted. An initial decrease in leukocytes in vehicle-treated mice was observed. However, after 3 days of sepsis, these mice showed high levels of peripheral leukocytes, which remained at high levels until the end of the experiment. In x1/2pal16 and x1/2i1LCA10-treated mice, leukocyte levels remained in the normal range. In x4i1pal12-treated mice, leukocytes levels increased immediately, but decreased 5 days after CLP to very low levels. This observation would match previous reports where either blocking of CXCR4 or stimulation of CXCR2 lead to neutrophilia in the peripheral blood of mice. The increase of leukocytes in the peripheral blood after x4i1pal12 treatment shows that CXCR2 blockade prevents peripheral blood neutrophilia. FIG. 11 shows the results.

EXAMPLE 8

Figure 12:
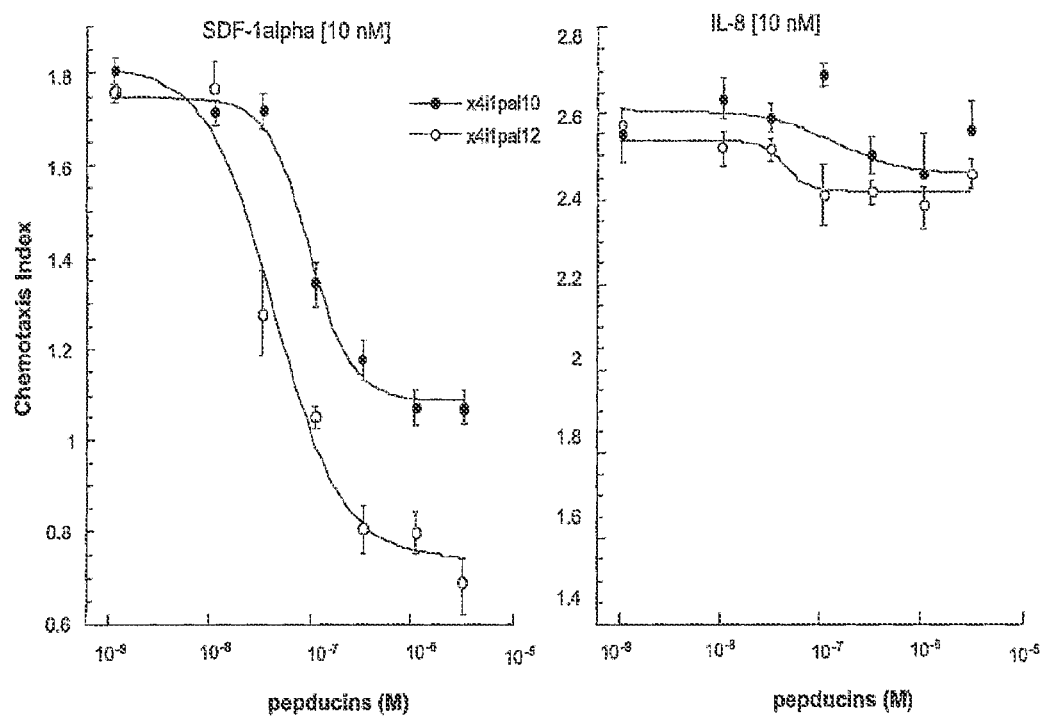
FIG. 12 is a graph showing how pepducins of the invention selectively reduce inflammation by demonstrating an inhibition in human neutrophil chemotaxis, as shown in more detail in Example 8.

Chemotaxis assays were performed in modified 48-well micro-chemotaxis chambers. 1 mio neutrophils/mL were allowed to migrate toward the chemoattractant in the lower wells. Neutrophils were pretreated with either 0.2% DMSO or the pepducins at the indicate concentrations. N=3. FIG. 12 shows that i1-loop pepducins of the invention have potent and selective anti-inflammatory action.

EXAMPLE 9

Figure 13:
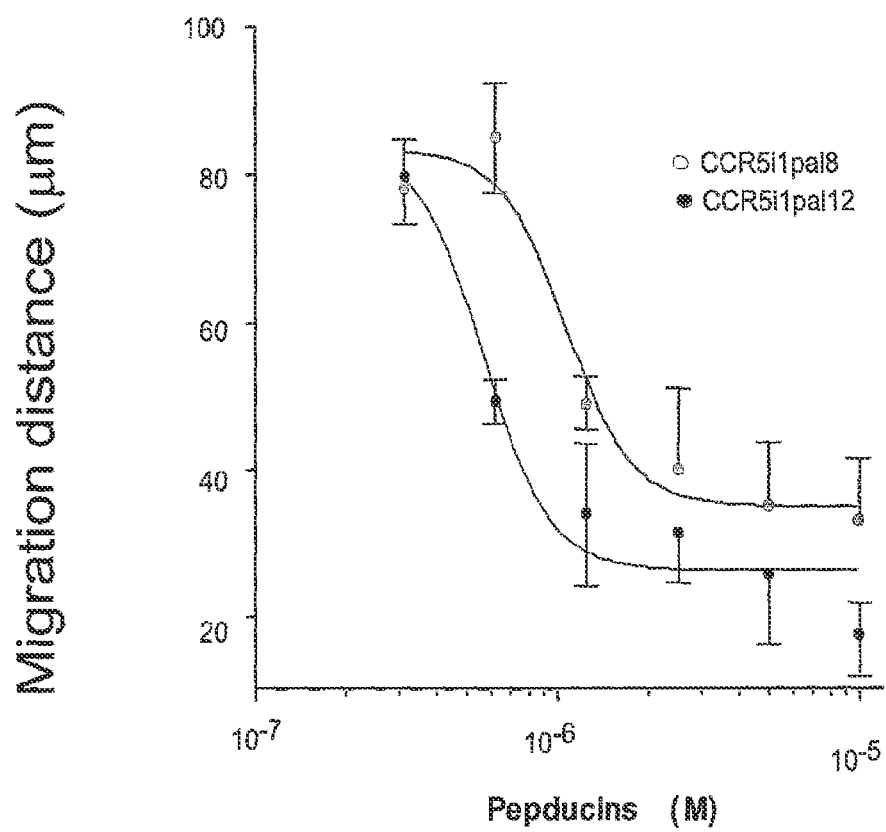
FIG. 13 is a graph showing how pepducins of the invention selectively reduce inflammation by demonstrating an inhibition in human monocyte chemotaxis, as shown in more detail in Example 9.

Chemotaxis assays were performed in modified 48-well micro-chemotaxis chambers. 1 mio neutrophils/mL were allowed to migrate toward Rantes-ligand for CCR1, CCR3 and CCR5 (20 ng/mL) in the lower wells. Neutrophils were pretreated with either 0.2% DMSO or the pepducins at the indicate concentrations. N=3. FIG. 13 shows that i1-loop pepducins of the invention have potent and selective anti-inflammatory action.

EXAMPLE 10

Figure 22:
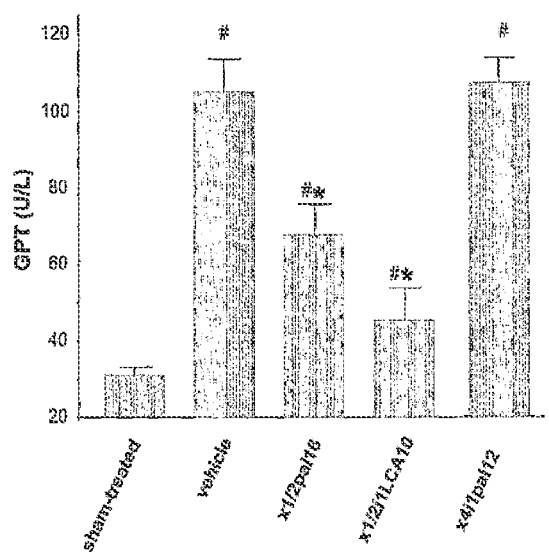
FIG. 22 is a bar graph showing the results of an experiment as described in more detail in Example 10.

Since organ failure determines the outcome of patients in SIRS, liver function was investigated. Mice were sacrificed 24 hours after CLP and plasma levels of ALT, an enzyme that increases with loss of liver function, were measured. In sham-treated mice, i.e., abdominal incision without cecal ligation and puncture, no elevation of ALT was observed. Vehicle and x4pal12 treated mice showed an increase in ALT, with x1/2pal16 and x1/2LCA10 treated mice an increase was observed but it was significantly less compared to vehicle treated mice. FIG. 22 shows the results, that CXCR2 pepducins can be used to improve liver function.

EXAMPLE 11

Figure 23:
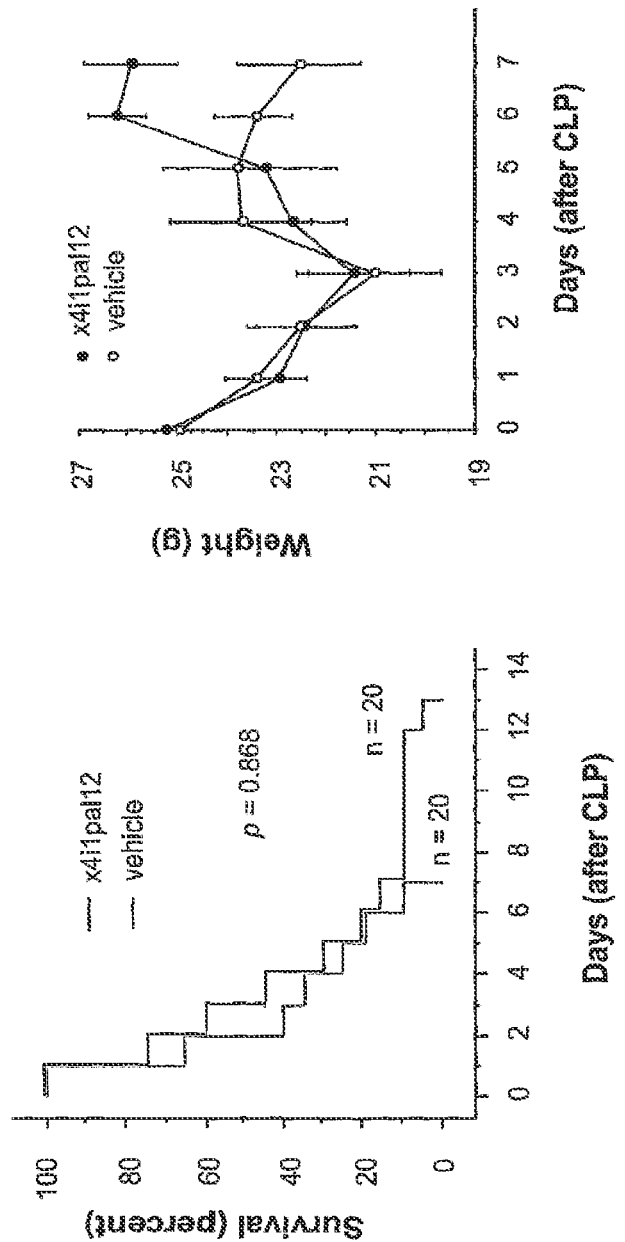
FIG. 23 is a graph showing the results of an experiment as described in more detail in Example 11.

CLP was performed on 6 to 8 week old female CF-1 mice. In the right panel, mice were treated with x4i1pal12 or vehicle (20% DMSO) at the time point of CLP. After the initial dose of 2.5 mg/kg, animals received 1 mg/kg of pepducin or vehicle s.c. every day for 6 days. In the left panel, mice were monitored for body weight every day. FIG. 23 shows the results.

EXAMPLE 12

Figure 24A:
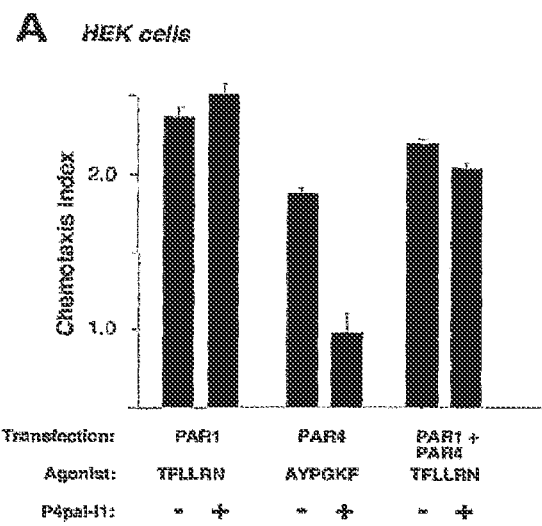
FIG. 24A is a bar graph showing HEK cells, transiently transfected with PAR1 and/or PAR4, allowed to migrate for 24 h toward 0.5 μM TFLLRN (SEQ ID NO. 33) or 500 μM AYPGKF (SEQ. ID NO. 34) in the presence or absence of 300 nM P4pal-i1.
Figure 24B:
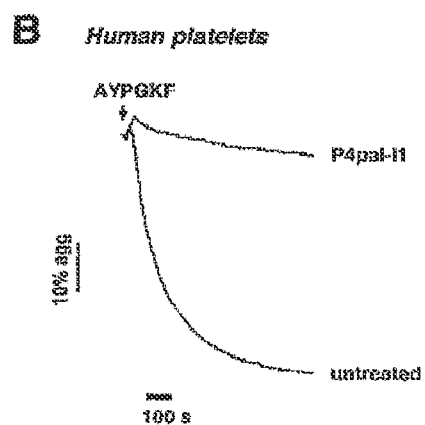
FIG. 24B is a graph showing human platelets pre-incubated for 2 min with 3 μM P4pal-i1 or buffer (untreated) prior to the addition of 160 μM AYPGKF.
Figure 24C:
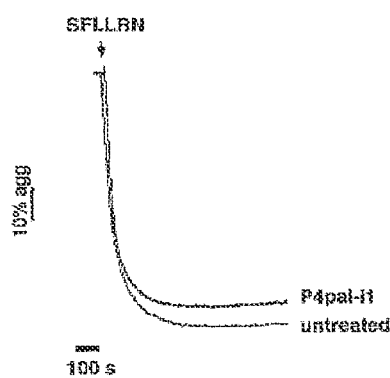
FIG. 24C is a graph showing human platelets pre-incubated for 2 min with 3 μM P4pal-i1 or buffer (untreated) prior to the addition of 13 μM SFLLRN.
Figure 24D:
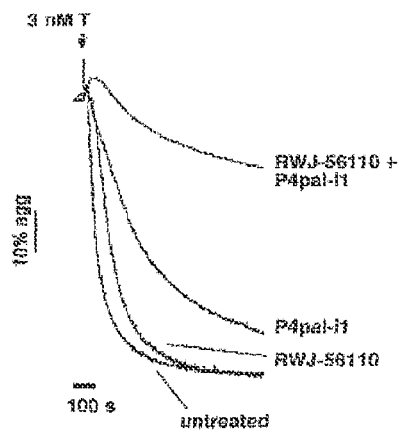
FIG. 24D is a graph showing platelets pre-incubated for 2 min with 1 μM RWJ-56110, 5 μM P4pal-i1, or 1 μM RWJ-56110 plus 5 μM P4pal-i1 prior to the addition of 3 nM thrombin (T). The data illustrated in these figures are the results of an experiment as described in detail in Example 12.

A more selective PAR4 pepducin based on the first intracellular loop (i1) of the receptor was developed. Because the i1 loop is on the opposite side of the receptor relative to the i3 loop, an i1 loop pepducin based on PAR4 exhibits reduced or no cross-inhibition of PAR1. PAR4 was expressed on HEK cells singly or in combination with PAR1. The PAR4 i1 pepducin, P4pal-i1, completely blocked the chemotactic response of PAR4 on HEK cells and prevented platelet aggregation to its peptide ligand, AYPGKF (SEQ ID NO. 34), as shown in FIGS. 24A-B. P4pal-i1 was selective for PAR4 and did not inhibit the chemotactic response of PAR1 nor did it appreciably inhibit platelet aggregation to the PAR1 peptide ligand, SFLLRN (SEQ ID NO. 35), as seen in FIGS. 24A and C. P4pal-i1 did not inhibit PAR1 even upon co-expression with PAR4 indicating that if PAR1 and PAR4 form a complex, the bound i1 pepducin of PAR4 does not appreciably affect signaling from PAR1. Likewise, when used alone, P4pal-i1 had only a minor effect on platelet aggregation to 3 nM thrombin since thrombin also activates PAR1 (FIG. 24D). However, when used in combination with the PAR1 antagonist, RWJ-56110, P4pal-i1 greatly inhibited aggregation to 3 nM thrombin. Thus, targeting either PAR1 or PAR4 alone has a limited effect on thrombin aggregation, whereas simultaneous inhibition of both PAR1 and PAR4 is effective in blocking the response to thrombin, thereby reducing or inhibiting thrombosis.

EXAMPLE 13

Figure 25A:
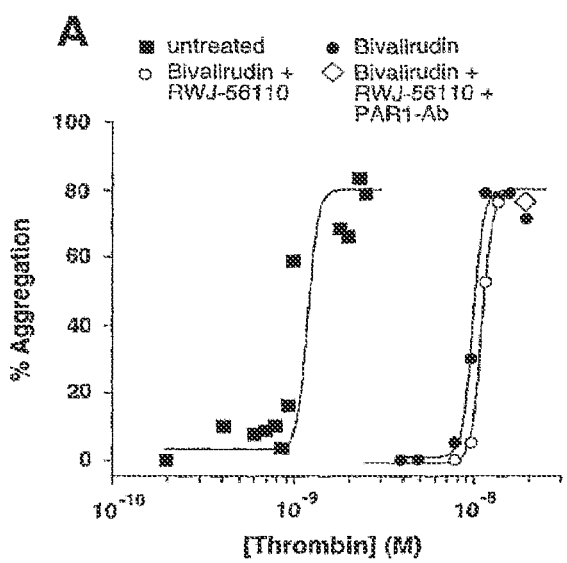
FIG. 25A is a graph illustrating a combination of bivalirudin and P4pal-i1 blocking thrombin-dependent aggregation; human platelets were pre-incubated for 2 min with buffer (untreated), bivalirudin (200 nM), RWJ-56110 (1 μM), and/or PAR1-Ab (74 μg/mL) as indicated prior to the addition of 20 pM-20 nM thrombin.
Figure 25B:
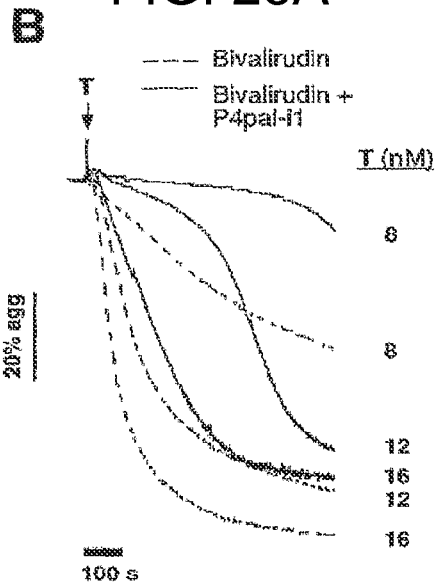
FIG. 25B is a graph illustrating platelets pre-incubated for 2 min with 200 nM bivalirudin plus or minus 5 μM P4pal-i1 prior to the addition of the indicated concentrations of thrombin. The data illustrated in these figures are the results of an experiment as described in detail in Example 13.

The effect of bivalirudin on platelet PAR1 and PAR4 responses was examined, and the efficacy of inhibiting thrombin-PAR1 interactions in combination with PAR4 blockade on platelet aggregation was assessed. To prevent thrombin from binding to the Hir site of PAR1, bivalirudin (aka Hirulog®, Angiomax™), which binds to thrombin with nanomolar affinity was used. Despite its widespread use in treating patients with acute coronary syndromes, the effects of bivalirudin on PAR1 and PAR4-dependent platelet activation have not been determined prior to the invention. Bivalirudin alone or bivalirudin plus RWJ-56110 gave a similar $EC_{50}$ (10-11 nM) of thrombin activation of PAR4-dependent aggregation as the PAR1-Ab (FIG. 25A). At concentrations greater than 11 nM, thrombin regained full activation of PAR4-dependent aggregation even when RWJ-56110 was supplemented with the PAR1-blocking antibody plus bivalirudin. These data indicate that neither of the Hir-blocking agents completely prevented interaction of the active site of thrombin with platelet PAR4. However, addition of the PAR4 pepducin, P4pal-i1, to bivalirudin-treated platelets greatly delayed and inhibited the extent of aggregation even at very high thrombin (12-16 nM) concentrations (FIG. 25B). These data reveal a mechanism in which thrombin-docked to the PAR1 Hir-motif enhances activation of PAR4, but at high enough thrombin concentrations, PAR4 is activated by thrombin unless blocked downstream with the PAR4 pepducin.

EXAMPLE 14

Figure 26:
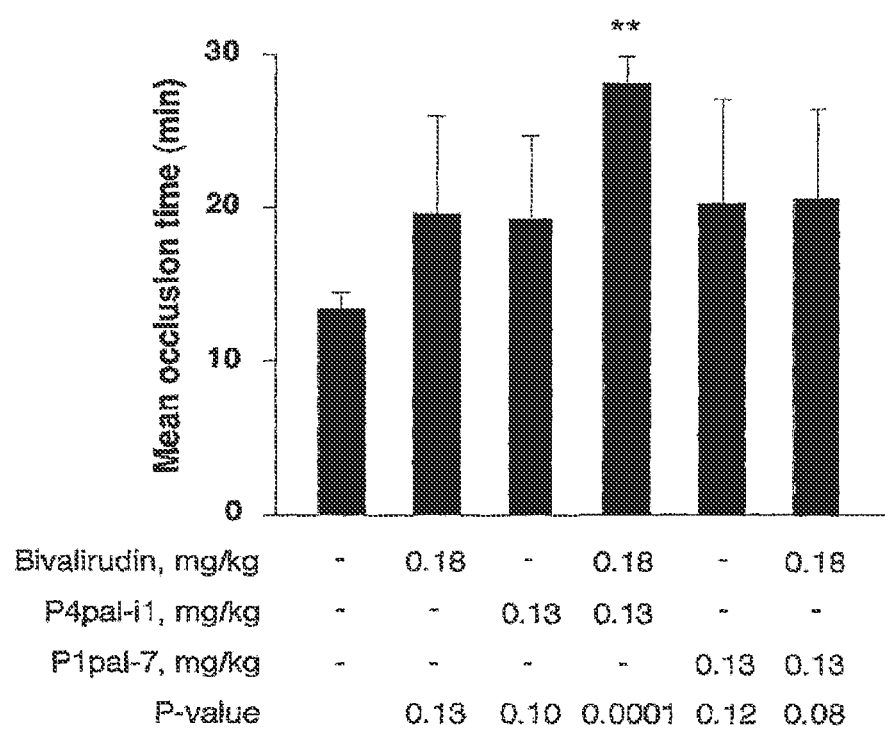
FIG. 26 is a bar graph illustrating a combination of bivalirudin plus P4pal-i1 blocking occlusion of carotid arteries in guinea pigs. Guinea pigs were treated with bivalirudin, P4pal-i1 and/or P1pal-7 (n=3-5 for each treatment group) 5 min prior to injury of the carotid artery with $FeCl_3$ as described in Example 14. P values relative to vehicle-treated are indicated at the bottom.

Arterial thrombosis in guinea pigs is prevented using a combination of bivalirudin and a PAR4 pepducin. A standard carotid artery injury model to assess the efficacy of simultaneous administration of bivalirudin and the PAR4 pepducin on arterial thrombosis in guinea pigs was used. Unlike mice which lack PAR1 on their platelets, guinea pigs share functional similarity with human platelets and express both PAR1 and PAR4. Consistent with earlier results using hirudin, bivalirudin alone (0.18 mg/kg) prolonged the mean arterial occlusion time from 13 min to 20 min, though this was not significant (FIG. 26). P4pal-i1 (0.13 mg/kg) prolonged the occlusion time to a similar extent. Co-administration of bivalirudin plus P4pal-i1 caused a significant (p=0.0001) protection against acute arterial occlusion. As has been shown with RWJ-58259, blockade of PAR1 alone with the PAR1 pepducin, P1pal-7, caused only partial protection of arterial thrombosis. In comparison to P4pal-i1, supplementation of P1pal-7 with bivalirudin gave no additional prolongation of the arterial occlusion time. Together, these in vivo data indicate that PAR4 must also be blocked to achieve significant protection against thrombosis.

These experiments support earlier observations with PAR1 and PAR4 pepducin antagonists and blocking antibodies, that targeting only PAR1 and not PAR4 may have a limited therapeutic effect. As an alternative therapeutic strategy, preventing the interaction of the PAR1 Hir motif with thrombin has the dual benefit of directly inhibiting PAR1 and indirectly inhibiting PAR4. These data demonstrate for the first time that the widely used anti-thrombotic agent, bivalirudin, was efficacious in blocking thrombin activation of both PAR1 and PAR4-dependent platelet aggregation. In combination with a PAR4 pepducin but not a PAR1 pepducin, bivalirudin was able to prevent acute arterial thrombosis.

EXAMPLE 15

Pepducins of the invention are used to interrupt established systemic inflammation and vascular damage as well prevent activation of the coagulation cascade without interference with host defense. i1 pepducins of the invention, e.g., based on CXCR1/2, do not cross-inhibit CXCR4. i1 pepducins completely block the chemotaxis responses of their cognate receptors on human and mouse neutrophils. x1/2LCA-i1 is selective for the CXCR1/2 IL-8 receptors and does not inhibit migration of human nor mouse leukocytes towards SDF-1α. Likewise, x1/2LCA-i1 does not inhibit CXCR4 even when co-expressed with CXCR1 or CXCR2. These data indicate that if the CXCR1 and CXCR4 receptors form a complex, the bound i1 pepducin of CXCR1 does not affect signaling from CXCR4.

The effects of the CXCR1/2 and CXCR4 pepducins on neutrophil homeostasis under normal versus pro-inflammatory conditions in mice were evaluated. Leukocyte recruitment was first assessed in a thioglycollate peritonitis model. The x1/2pal-i3 and x1/2LCA-i1-pepducins completely inhibited transmigration of neutrophils into the peritoneal cavity with IC50 values of 0.03 mg/kg and 0.15 mg/kg, respectively. Conversely, mice treated with the CXCR4 antagonist, x4pal-i1 (EC50~0.1 mg/kg), showed a substantial increase in peritoneal neutrophils.

The long-term effects of the chemokine pepducins on peripheral leukocyte counts were assessed in healthy untreated mice. Pepducins were injected once per day sub-Q (2.5 mg/kg day 1, 1.0 mg/kg days 2-6) and circulating leukocyte levels measured over a one week period. In the healthy mice, neither x1/2pal-i3 nor x1/2LCA-i1 altered the leukocyte count as compared to vehicle-treated mice. In contrast, x4pal-i1 caused a leukocytosis in peripheral blood, consistent with previous studies. The effects of the chemokine pepducins on peripheral leukocyte count were quite similar in septic mice subjected to cecal ligation and puncture (CLP). Vehicle-treated mice exhibited an initial leukopenia at 24 h after CLP, then leukocytosis on day 3. Once per day administration of x1/2pal-i3 or x1/2LCA-i1 kept the neutrophil count of the CLP-mice within the normal range, whereas x4pal-i1 led to an accelerated leukocytosis on day 1 and leukopenia by day 7. Together, these data indicate that CXCR2 and CXCR4 receptors play opposing roles in neutrophil homeostasis in both normal and pro-inflammatory states in mice.

Chemokine receptor pepducins were tested for the ability to protect or potentially reverse the progression of lethal CLP peritonitis in mice. In the first set of experiments, pepducins were given immediately after the CLP procedure at a dose of 2.5 mg/kg. The subsequent doses were 1 mg/kg until day 6 after which treatment was stopped. None of the mice received antibiotic therapy. A highly significant decrease was observed in sepsis-induced mortality for both the x1/2LCA-i1 and x1/2pal-i3 pepducins. Strikingly, over the 17-d observation period only 1/34 pepducin-treated mice died, whereas 17/17 of the untreated mice died by day 9. Despite discontinuation of CXCR1/2 pepducin therapy at day 6, survival remained nearly 100% thereafter.

The diagnosis of sepsis is often delayed and agents cannot be readily administered in a preventative mode, therefore pepducin treatment was withheld until 8 h after the CLP procedure. Even with delayed treatment, a highly significant reduction in mortality was seen as compared to untreated mice. Overall survival was 26/30 in the delayed CXCR1/2 pepducin-treated mice as opposed to 0/20 of the untreated mice. Administration of the CXCR4 pepducin, x4pal-i1, had no effect on survival. CXCR1/2-pepducin treated mice gained weight, were active and maintained normal grooming behavior after day 1 even when pepducin therapy was delayed by 8 h.

Blockade of CXCR1/2 signaling with pepducins reversed several criteria of established SIRS in the septic mice. First, the effect of CXCR1/2 pepducins on systemic KC levels, the mouse IL-8 ortholog was examined. In untreated mice, KC levels rose over the 16 h period after CLP and remained elevated for at least 48 h. Following administration of the CXCR1/2 pepducins at the 8 h time point, the systemic KC levels rapidly dropped and remained low thereafter. Many of the untreated CLP mice became tachypnic and hypoxemic as early as 24 h and this correlated well with mortality. During sepsis, bacterial endotoxin stimulates lung epithelia to secrete IL-8 which recruits and activates leukocytes. The resulting neutrophil margination eventually leads to lung damage. The number of neutrophils in the bronchioalveolar lavage (BAL) fluid of untreated mice increased by 100-fold as early as 4 h after CLP and then rose to 200-300 fold after 8 h. Treatment with x1/2pal-i3 or x1/2LCA-i1 at 8 h caused a rapid drop in BAL neutrophils which stayed at low levels. Histological analyses of the lungs harvested at 48 h in the untreated CLP mice revealed collapsed alveoli, leukocyte infiltration and extensive fibrin deposition. x1/2pal-i3 and x1/2LCA-i1 gave significant protection against fibrin deposition and alveoli appeared histologically normal. The CXCR1/2 pepducins also completely blocked transmigration of leukocytes across LPS-simulated epithelial and endothelial monolayers. Likewise, the CXCR1/2 pepducins prevented IL-8 dependent chemotaxis of human macrophages but not monocytes as expected. CXCR1/2 pepducins significantly inhibited in vivo mouse macrophage transmigration into the peritoneal cavity. Together, these data indicate that the pepducins exert their therapeutic effects by blocking CXCR1/2 receptors on many cell types.

Liver failure is a common sequalae of severe sepsis. Treatment with the CXCR1/2 pepducins right after CLP reduced liver damage as evidenced by decreases of 52-87% in liver enzyme levels (AST, ALT) whereas the CXCR4 pepducin, x4pal-i1, had no effect. When CXCR1/2 pepducin treatment was initiated 8 h after CLP, the rise in plasma AST and ALT levels were halted by the 16 h time point and then dropped to near normal levels. Together, these data indicate that blockade of CXCR1/2 signaling with pepducins reverses several criteria of established SIRS in the septic mice, indicating that this approach is beneficial in the setting of advanced disease.

Spontaneous bleeding and the development of thrombi was observed in many of the untreated CLP mice, consistent with the development of disseminated intravascular coagulation (DIC). Therefore, systemic platelet activation was observed by measuring platelet counts and D-dimer levels, a marker of the increased fibrin production and subsequent fibrinolysis that occurs during DIC. CXCR1/2 pepducins significantly protected against thrombocytopenia at 24 h even when pepducin treatment was delayed until 8 h after CLP. D-dimer levels were found to be highly elevated 48 h after the CLP procedure in untreated mice. However, x1/2pal-i3 and x1/2LCA-i1-treated mice showed significant reductions in levels of D-dimer. When the CXCR1/2 pepducin treatment was delayed until 8 h after the CLP procedure, D-dimer levels were still reduced by 60-70%. These data are the first demonstration that the coagulopathy that develops in overt sepsis is ameliorated by blockade of CXCR2.

Recent studies using mice that lack a functional CXCR2 receptor showed increased survival in the CLP sepsis model, albeit with 3 to 4-fold higher mortality rates than observed in our study. The improved outcome in mortality following pepducin treatment relative to the effect of deletion of CXCR2 could be due to several factors. CXCR2 (−/−) mice lack CXCR2 during their entire life span and have additional defects in their adaptive immune system making it hard to distinguish between acute CXCR2-specific effects and compensatory mechanisms arising from abnormal myelopoiesis. The CF-1 mice used are outbred wild-type animals which might confer a survival advantage in the context of the severe immunogenic challenge from CLP. It is noteworthy that the anti-CXCR1/2 pepducins do not suppress leukocyte migration toward other chemokines such as bacterial fMLP, therefore, the pepducin effects may be considered to be immunomodulatory rather than immunosuppressive. Furthermore, the application of pepducin technology helps validate the results from genetic knock-out and provides further insight into the etiology and treatment of complex diseases such as sepsis.

Equivalents

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A chimeric polypeptide comprising:
   a) a first domain that is an amino acid sequence selected from the group consisting of YQKKLRSMTD (SEQ ID NO:24) and MGYQKKLRSMTD (SEQ ID NO:25) and
   b) a second domain, attached to the first domain, wherein the second domain comprises a cell-penetrating, membrane-tethering hydrophobic moiety comprising a lipid, a cholesterol, a phospholipid, a steroid, a sphingosine, a ceramide, an octylglycine, a 2-cyclohexylalanine, or a benzolylphenylalanine,
   wherein said chimeric polypeptide is an antagonist of a chemokine receptor.

2. The chimeric polypeptide of claim 1, wherein the chemokine receptor is a CXC chemokine receptor.

3. The chimeric polypeptide of claim 1, wherein the second domain is attached at the N-terminal end of the first domain.

4. The chimeric polypeptide of claim 1, wherein the second domain comprises a lipid.

5. The chimeric polypeptide of claim 4, wherein the second domain comprises a hydrophobic moiety that is selected from the group consisting of a: nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$) moiety.

6. The chimeric polypeptide of claim 4, wherein the second domain comprises a palmitoyl moiety.

7. The chimeric polypeptide of claim 4, wherein the second domain comprises a myristoyl ($C_{14}$) or pentadecanoyl ($C_{15}$) moiety.

8. The chimeric polypeptide of claim 1, wherein the second domain comprises a lithocholic acid or a salt thereof.

9. The chimeric polypeptide of claim 1, wherein the second domain comprises a hydrophobic moiety that is selected from the group consisting of a cholesterol, a phospholipid, a steroid, a sphingosine, a ceramide, an octyl-glycine, a 2-cyclohexylalanine, a benzolylphenylalanine, and a $C_3$-$C_8$ fatty acid.

10. The chimeric polypeptide of claim 1, wherein the second domain comprises a steroid.

11. A pharmaceutical composition comprising the chimeric polypeptide of claim 1 and a pharmaceutically acceptable carrier.

12. The chimeric polypeptide of claim 1, wherein the second domain comprises a hydrophobic moiety that is selected from the group consisting of a phospholipid, a steroid, a sphingosine, a ceramide, an octylglycine, a 2-cyclohexylalanine, and a benzolylphenylalanine.

13. The chimeric polypeptide of claim 1, wherein the second domain is attached to the first domain with an amide bond, a sulfhydryl, an amine, an alcohol, a phenolic group, or a carbon-carbon bond.

14. The chimeric polypeptide of claim 1, wherein the second domain is attached at the C-terminal end of the first domain.

15. A chimeric polypeptide comprising:
  (a) a first domain that comprises an amino acid sequence that is selected from the group consisting of ILKMKVKKPAV (SEQ ID NO: 28), VLATQAPRLPST (SEQ ID NO: 29), ATQAPRLPST (SEQ ID NO: 30), VLATGAPRLPST (SEQ ID NO:31), ATGAPRLPST (SEQ ID NO:32), and FLFRTKKKHPAV (SEQ ID NO: 17) and
  (b) a second domain, attached to the first domain, wherein the second domain comprises a cell-penetrating, membrane-tethering hydrophobic moiety comprising a lipid, a cholesterol, a phospholipid, a steroid, a sphingosine, a ceramide, an octylglycine, a 2- cyclohexylalanine, or a benzolylphenylalanine;
  wherein said chimeric polypeptide is an antagonist of a protease-activated receptor (PAR).

16. The chimeric polypeptide of claim 15, wherein said PAR is PARI, PAR2, or PAR4.

17. The chimeric polypeptide of claim 15, wherein the second domain comprises a lipid.

18. The chimeric polypeptide of claim 15, wherein the second domain comprises a hydrophobic moiety that is selected from the group consisting of a: nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$) moiety.

19. The chimeric polypeptide of claim 15, wherein the second domain is attached to the first domain with an amide bond, a sulfhydryl, an amine, an alcohol, a phenolic group, or a carbon-carbon bond.

20. The chimeric polypeptide of claim 15, wherein the second domain comprises a palmitoyl moiety.

21. The chimeric polypeptide of claim 15, wherein the second domain comprises a lithocholic acid or a salt thereof.

22. The chimeric polypeptide of claim 15, wherein the second domain comprises a hydrophobic moiety that is selected from the group consisting of a cholesterol, a phospholipid, a steroid, a sphingosine, a ceramide, an octyl-glycine, a 2- cyclohexylalanine, a benzolylphenylalanine, and a $C_3$-$C_8$ fatty acid.

23. The chimeric polypeptide of claim 15, wherein the second domain comprises a steroid.

24. The chimeric polypeptide of claim 15, wherein the second domain comprises a hydrophobic moiety that is selected from the group consisting of a phospholipid, a steroid, a sphingosine, a ceramide, an octylglycine, a 2-cyclohexylalanine, and a benzolylphenylalanine.

25. A pharmaceutical composition comprising the chimeric peptide of claim 15 and a pharmaceutically acceptable carrier.

26. A chimeric polypeptide comprising:
  (a) a first domain that comprises an amino acid sequence that is selected from the group consisting of ILYSRVGRSVTD (SEQ ID NO: 18), YSRVGRSVTD (SEQ ID NO: 19), KRLKSMTD (SEQ ID NO:26), and LINCKRLKSMTD (SEQ ID NO:27) and
  (b) a second domain, attached to the first domain, wherein the second domain comprises a cell-penetrating, membrane-tethering hydrophobic moiety comprising a lipid, a cholesterol, a phospholipid, a steroid, a sphingosine, a ceramide, an octylglycine, a 2- cyclohexylalanine, or a benzolylphenylalanine;
  wherein said chimeric polypeptide is an antagonist of a chemokine receptor.

27. The chimeric polypeptide of claim 26, wherein the chemokine receptor is a CXC chemokine receptor or a CC chemokine receptor.

28. The chimeric polypeptide of claim 26, wherein said second domain comprises a lipid.

29. The chimeric polypeptide of claim 26, wherein said second domain comprises a hydrophobic moiety that is selected from the group consisting of a: nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$) moiety.

30. The chimeric polypeptide of claim 26, wherein the second domain is attached to the first domain with an amide bond, a sulfhydryl, an amine, an alcohol, a phenolic group, or a carbon-carbon bond.

31. The chimeric polypeptide of claim 26, wherein the second domain comprises a palmitoyl moiety.

32. The chimeric polypeptide of claim 26, wherein the second domain comprises a myristoyl ($C_{14}$) or pentadecanoyl ($C_{15}$) moiety.

33. The chimeric polypeptide of claim 26, wherein the second domain comprises a lithocholic acid or a salt thereof.

34. The chimeric polypeptide of claim 26, wherein the second domain comprises a hydrophobic moiety that is selected from the group consisting of a cholesterol, a phospholipid, a steroid, a sphingosine, a ceramide, an octyl-glycine, a 2- cyclohexylalanine, a benzolylphenylalanine, and a $C_3$-$C_8$ fatty acid.

35. The chimeric polypeptide of claim 26, wherein the second domain comprises a steroid.

36. The chimeric polypeptide of claim 26, wherein the second domain comprises a hydrophobic moiety that is selected from the group consisting of a phospholipid, a steroid, a sphingosine, a ceramide, an octylglycine, a 2-cyclohexylalanine, and a benzolylphenylalanine.

37. A pharmaceutical composition comprising the chimeric peptide of claim 26 and a pharmaceutically acceptable carrier.

* * * * *

```
                             SEQUENCE LISTING

<160> NUMBER OF SEQ ID NOS: 104

<210> SEQ ID NO 1
<211> LENGTH: 61
<212> TYPE: PRT
<213> ORGANISM: Homo sapiens

<400> SEQUENCE: 1

Lys Tyr Val Val Ile Ile Ala Tyr Ala Leu Val Phe Leu Leu Ser Leu
1               5                   10                  15

Leu Gly Asn Ser Leu Val Met Leu Val Ile Leu Tyr Ser Arg Val Gly
            20                  25                  30

Arg Ser Val Thr Asp Val Tyr Leu Leu Asn Leu Ala Leu Ala Asp Leu
        35                  40                  45

Leu Phe Ala Leu Thr Leu Pro Ile Trp Ala Ala Ser Lys
    50                  55                  60

<210> SEQ ID NO 2
<211> LENGTH: 61
<212> TYPE: PRT
<213> ORGANISM: Pan troglodytes

<400> SEQUENCE: 2

Lys Tyr Val Val Ile Ile Thr Tyr Ala Leu Val Phe Leu Leu Ser Leu
1               5                   10                  15

Leu Gly Asn Ser Leu Val Met Leu Val Ile Leu Tyr Ser Arg Val Gly
            20                  25                  30

Arg Ser Val Thr Asp Val Tyr Leu Leu Asn Leu Ala Leu Ala Asp Leu
        35                  40                  45

Leu Phe Ala Leu Thr Leu Pro Ile Trp Ala Ala Ser Lys
    50                  55                  60

<210> SEQ ID NO 3
<211> LENGTH: 61
<212> TYPE: PRT
<213> ORGANISM: Gorilla gorilla

<400> SEQUENCE: 3

Lys Tyr Val Val Ile Ile Thr Tyr Ala Leu Ala Phe Leu Leu Ser Leu
1               5                   10                  15

Leu Gly Asn Ser Leu Val Met Leu Val Ile Leu Tyr Ser Arg Gly Gly
            20                  25                  30

Arg Ser Val Thr Asp Val Tyr Leu Leu Asn Leu Ala Leu Ala Asp Leu
        35                  40                  45

Leu Phe Ala Leu Thr Leu Pro Ile Trp Ala Ala Ser Lys
    50                  55                  60

<210> SEQ ID NO 4
<211> LENGTH: 61
<212> TYPE: PRT
<213> ORGANISM: Rabbit

<400> SEQUENCE: 4

Lys Tyr Val Val Val Val Ile Tyr Ala Leu Val Phe Leu Leu Ser Leu
1               5                   10                  15
```

```
Leu Gly Asn Ser Leu Val Met Leu Val Ile Leu Tyr Ser Arg Ser Asn
            20                  25                  30

Arg Ser Val Thr Asp Val Tyr Leu Leu Asn Leu Ala Met Ala Asp Leu
            35                  40                  45

Leu Phe Ala Leu Thr Met Pro Ile Trp Ala Val Ser Lys
        50                  55                  60

<210> SEQ ID NO 5
<211> LENGTH: 61
<212> TYPE: PRT
<213> ORGANISM: Rat

<400> SEQUENCE: 5

Arg Gln Ala Val Val Phe Tyr Ala Leu Val Phe Leu Leu Ser Leu
1               5                   10                  15

Leu Gly Asn Ser Leu Val Met Leu Val Ile Leu Tyr Arg Arg Arg Thr
            20                  25                  30

Arg Ser Val Thr Asp Val Tyr Val Leu Asn Leu Ala Ile Ala Asp Leu
            35                  40                  45

Leu Phe Ser Leu Thr Leu Pro Phe Leu Ala Val Ser Lys
        50                  55                  60

<210> SEQ ID NO 6
<211> LENGTH: 61
<212> TYPE: PRT
<213> ORGANISM: Homo sapiens

<400> SEQUENCE: 6

Lys Tyr Phe Val Val Ile Ile Tyr Ala Leu Val Phe Leu Leu Ser Leu
1               5                   10                  15

Leu Gly Asn Ser Leu Val Met Leu Val Ile Leu Tyr Ser Arg Val Gly
            20                  25                  30

Arg Ser Val Thr Asp Val Tyr Leu Leu Asn Leu Ala Leu Ala Asp Leu
            35                  40                  45

Leu Phe Ala Leu Thr Leu Pro Ile Trp Ala Ala Ser Lys
        50                  55                  60

<210> SEQ ID NO 7
<211> LENGTH: 61
<212> TYPE: PRT
<213> ORGANISM: Mouse

<400> SEQUENCE: 7

Ser Tyr Ala Val Val Ile Tyr Val Leu Val Thr Leu Leu Ser Leu
1               5                   10                  15

Val Gly Asn Ser Leu Val Met Leu Val Ile Leu Tyr Asn Arg Ser Thr
            20                  25                  30

Cys Ser Val Thr Asp Val Tyr Leu Leu Asn Leu Ala Ile Ala Asp Leu
            35                  40                  45

Phe Phe Ala Leu Thr Leu Pro Val Trp Ala Ala Ser Lys
        50                  55                  60

<210> SEQ ID NO 8
<211> LENGTH: 61
<212> TYPE: PRT
<213> ORGANISM: Pan troglodytes

<400> SEQUENCE: 8

Lys Tyr Phe Val Val Ile Ile Tyr Ala Leu Val Phe Leu Leu Ser Leu
1               5                   10                  15
```

Leu Gly Asn Ser Leu Val Met Leu Val Ile Leu Tyr Ser Arg Val Gly
            20                  25                  30

Arg Ser Val Thr Asp Val Tyr Leu Asn Leu Ala Leu Ala Asp Leu
            35                  40                  45

Leu Phe Ala Leu Thr Leu Pro Ile Trp Ala Ala Ser Lys
    50                  55                  60

<210> SEQ ID NO 9
<211> LENGTH: 61
<212> TYPE: PRT
<213> ORGANISM: Macaca mulatta

<400> SEQUENCE: 9

Lys Tyr Phe Val Val Ile Ile Tyr Ala Leu Val Phe Leu Leu Ser Leu
1               5                   10                  15

Leu Gly Asn Ser Leu Val Met Leu Val Ile Leu Tyr Ser Arg Val Gly
            20                  25                  30

Arg Ser Val Thr Asp Val Tyr Leu Leu Asn Leu Ala Leu Ala Asp Leu
            35                  40                  45

Leu Phe Ala Leu Thr Leu Pro Ile Trp Ala Ala Ser Lys
    50                  55                  60

<210> SEQ ID NO 10
<211> LENGTH: 61
<212> TYPE: PRT
<213> ORGANISM: Gorilla gorilla

<400> SEQUENCE: 10

Lys Tyr Phe Val Val Ile Ile Tyr Ala Leu Val Phe Leu Leu Ser Leu
1               5                   10                  15

Leu Gly Asn Ser Leu Val Ile Leu Val Ile Leu Tyr Ser Arg Val Gly
            20                  25                  30

Arg Ser Val Thr Asp Val Tyr Leu Leu Asn Leu Ala Leu Ala Asp Leu
            35                  40                  45

Leu Phe Ala Leu Thr Leu Pro Ile Trp Ala Ala Ser Lys
    50                  55                  60

<210> SEQ ID NO 11
<211> LENGTH: 61
<212> TYPE: PRT
<213> ORGANISM: Rabbit

<400> SEQUENCE: 11

Ser Tyr Val Val Leu Ile Thr Tyr Ile Leu Val Phe Leu Leu Ser Leu
1               5                   10                  15

Leu Gly Asn Ser Leu Val Met Leu Val Ile Leu Tyr Ser Arg Ser Thr
            20                  25                  30

Cys Ser Val Thr Asp Val Tyr Leu Leu Asn Leu Ala Ile Ala Asp Leu
            35                  40                  45

Leu Phe Ala Thr Thr Leu Pro Ile Trp Ala Ala Ser Lys
    50                  55                  60

<210> SEQ ID NO 12
<211> LENGTH: 61
<212> TYPE: PRT
<213> ORGANISM: Canis familiaris

<400> SEQUENCE: 12

Lys Tyr Ala Val Val Val Ile Tyr Val Leu Val Phe Leu Leu Asn Leu
1               5                   10                  15

```
Leu Gly Asn Ser Leu Val Ile Met Val Val Leu Tyr Ser Arg Val Ser
            20                  25                  30

His Ser Val Thr Asp Val Tyr Leu Leu Asn Leu Ala Ile Ala Asp Leu
            35                  40                  45

Leu Phe Ala Leu Thr Leu Pro Ile Trp Ala Val Ser Lys
    50                  55                  60

<210> SEQ ID NO 13
<211> LENGTH: 61
<212> TYPE: PRT
<213> ORGANISM: Bovine

<400> SEQUENCE: 13

Lys Tyr Ala Val Val Ile Asp Ala Leu Val Phe Leu Leu Ser Leu
1               5                   10                  15

Leu Gly Asn Ser Leu Val Met Leu Val Ile Leu Tyr Ser Arg Ile Gly
            20                  25                  30

Arg Ser Val Thr Asp Val Tyr Leu Leu Asn Leu Ala Met Ala Asp Leu
            35                  40                  45

Leu Phe Ala Met Thr Leu Pro Ile Trp Thr Ala Ser Lys
    50                  55                  60

<210> SEQ ID NO 14
<211> LENGTH: 61
<212> TYPE: PRT
<213> ORGANISM: Rat

<400> SEQUENCE: 14

Arg Tyr Ala Val Val Ile Tyr Val Leu Val Thr Leu Leu Ser Leu
1               5                   10                  15

Val Gly Asn Ser Leu Val Met Leu Val Ile Leu Tyr Asn Arg Ser Thr
            20                  25                  30

Cys Ser Val Thr Asp Val Tyr Leu Leu Asn Leu Ala Ile Ala Asp Leu
            35                  40                  45

Phe Phe Ala Leu Thr Leu Pro Val Trp Ala Ala Ser Lys
    50                  55                  60

<210> SEQ ID NO 15
<211> LENGTH: 352
<212> TYPE: PRT
<213> ORGANISM: Homo sapiens

<400> SEQUENCE: 15

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
            85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125
```

```
Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
                195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 16
<211> LENGTH: 24
<212> TYPE: PRT
<213> ORGANISM: Macaca fascicularis

<400> SEQUENCE: 16

Ile Phe Leu Pro Thr Ile Tyr Ser Ile Ile Phe Leu Thr Gly Ile Val
1               5                   10                  15

Gly Asn Gly Leu Val Ile Leu Val
            20

<210> SEQ ID NO 17
<211> LENGTH: 12
<212> TYPE: PRT
<213> ORGANISM: Artificial Sequence
<220> FEATURE:
<223> OTHER INFORMATION: chemically synthesized

<400> SEQUENCE: 17

Phe Leu Phe Arg Thr Lys Lys Lys His Pro Ala Val
1               5                   10

<210> SEQ ID NO 18
<211> LENGTH: 12
<212> TYPE: PRT
<213> ORGANISM: Artificial Sequence
<220> FEATURE:
<223> OTHER INFORMATION: chemically synthesized

<400> SEQUENCE: 18
```

-continued

Ile Leu Tyr Ser Arg Val Gly Arg Ser Val Thr Asp
1               5                   10

<210> SEQ ID NO 19
<211> LENGTH: 10
<212> TYPE: PRT
<213> ORGANISM: Artificial Sequence
<220> FEATURE:
<223> OTHER INFORMATION: chemically synthesized

<400> SEQUENCE: 19

Tyr Ser Arg Val Gly Arg Ser Val Thr Asp
1               5                   10

<210> SEQ ID NO 20
<211> LENGTH: 10
<212> TYPE: PRT
<213> ORGANISM: Artificial Sequence
<220> FEATURE:
<223> OTHER INFORMATION: chemically synthesized

<400> SEQUENCE: 20

Tyr Ser Arg Val Gly Arg Ser Val Thr Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: chemically synthesized

<400> SEQUENCE: 21

Ile Leu Tyr Ser Arg Val Gly Arg Ser Val Thr Asp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: chemically synthesized

<400> SEQUENCE: 22

Tyr Ser Arg Val Gly Arg Ser Val Thr Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: chemically synthesized

<400> SEQUENCE: 23

Tyr Ser Arg Val Gly Arg Ser Val Thr Asp
1               5                   10

<210> SEQ ID NO 24
<211> LENGTH: 10
<212> TYPE: PRT
<213> ORGANISM: Artificial Sequence
<220> FEATURE:
<223> OTHER INFORMATION: chemically synthesized

<400> SEQUENCE: 24

Tyr Gln Lys Lys Leu Arg Ser Met Thr Asp
1               5                   10

```
<210> SEQ ID NO 25
<211> LENGTH: 12
<212> TYPE: PRT
<213> ORGANISM: Artificial Sequence
<220> FEATURE:
<223> OTHER INFORMATION: chemically synthesized

<400> SEQUENCE: 25

Met Gly Tyr Gln Lys Lys Leu Arg Ser Met Thr Asp
1               5                   10

<210> SEQ ID NO 26
<211> LENGTH: 8
<212> TYPE: PRT
<213> ORGANISM: Artificial Sequence
<220> FEATURE:
<223> OTHER INFORMATION: chemically synthesized

<400> SEQUENCE: 26

Lys Arg Leu Lys Ser Met Thr Asp
1               5

<210> SEQ ID NO 27
<211> LENGTH: 12
<212> TYPE: PRT
<213> ORGANISM: Artificial Sequence
<220> FEATURE:
<223> OTHER INFORMATION: chemically synthesized

<400> SEQUENCE: 27

Leu Ile Asn Cys Lys Arg Leu Lys Ser Met Thr Asp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: chemically synthesized

<400> SEQUENCE: 28

Ile Leu Lys Met Lys Val Lys Lys Pro Ala Val
1               5                   10

<210> SEQ ID NO 29
<211> LENGTH: 12
<212> TYPE: PRT
<213> ORGANISM: Artificial Sequence
<220> FEATURE:
<223> OTHER INFORMATION: chemically synthesized

<400> SEQUENCE: 29

Val Leu Ala Thr Gln Ala Pro Arg Leu Pro Ser Thr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: chemically synthesized

<400> SEQUENCE: 30

Ala Thr Gln Ala Pro Arg Leu Pro Ser Thr
1               5                   10
```

```
<210> SEQ ID NO 31
<211> LENGTH: 12
<212> TYPE: PRT
<213> ORGANISM: Artificial Sequence
<220> FEATURE:
<223> OTHER INFORMATION: chemically synthesized

<400> SEQUENCE: 31

Val Leu Ala Thr Gly Ala Pro Arg Leu Pro Ser Thr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: chemically synthesized

<400> SEQUENCE: 32

Ala Thr Gly Ala Pro Arg Leu Pro Ser Thr
1               5                   10

<210> SEQ ID NO 33
<211> LENGTH: 6
<212> TYPE: PRT
<213> ORGANISM: Artificial Sequence
<220> FEATURE:
<223> OTHER INFORMATION: chemically synthesized

<400> SEQUENCE: 33

Thr Phe Leu Leu Arg Asn
1               5

<210> SEQ ID NO 34
<211> LENGTH: 6
<212> TYPE: PRT
<213> ORGANISM: Artificial Sequence
<220> FEATURE:
<223> OTHER INFORMATION: chemically synthesized

<400> SEQUENCE: 34

Ala Tyr Pro Gly Lys Phe
1               5

<210> SEQ ID NO 35
<211> LENGTH: 6
<212> TYPE: PRT
<213> ORGANISM: Artificial Sequence
<220> FEATURE:
<223> OTHER INFORMATION: chemically synthesized

<400> SEQUENCE: 35

Ser Phe Leu Leu Arg Asn
1               5

<210> SEQ ID NO 36
<211> LENGTH: 61
<212> TYPE: PRT
<213> ORGANISM: Homo sapiens

<400> SEQUENCE: 36

Asn Lys Ile Phe Leu Pro Thr Ile Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45
```

```
Leu Leu Phe Val Ile Thr Leu Pro Phe Trp Ala Val Asp
    50                  55                  60
```

<210> SEQ ID NO 37
<211> LENGTH: 61
<212> TYPE: PRT
<213> ORGANISM: Mouse

<400> SEQUENCE: 37

```
Asn Arg Ile Phe Leu Pro Thr Ile Tyr Phe Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Ile Thr Leu Pro Phe Trp Ala Val Asp
    50                  55                  60
```

<210> SEQ ID NO 38
<211> LENGTH: 61
<212> TYPE: PRT
<213> ORGANISM: Macaca fasicularis papillomavirus

<400> SEQUENCE: 38

```
Asn Arg Ile Phe Leu Pro Thr Ile Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Ile Thr Leu Pro Phe Trp Ala Val Asp
    50                  55                  60
```

<210> SEQ ID NO 39
<211> LENGTH: 61
<212> TYPE: PRT
<213> ORGANISM: Macaca mulatta

<400> SEQUENCE: 39

```
Asn Arg Ile Phe Leu Pro Thr Ile Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Ile Thr Leu Pro Phe Trp Ala Val Asp
    50                  55                  60
```

<210> SEQ ID NO 40
<211> LENGTH: 61
<212> TYPE: PRT
<213> ORGANISM: Pan troglodytes

<400> SEQUENCE: 40

```
Asn Lys Ile Phe Leu Pro Thr Ile Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45
```

Leu Leu Phe Val Ile Thr Leu Pro Phe Trp Ala Val Asp
    50                  55                  60

<210> SEQ ID NO 41
<211> LENGTH: 61
<212> TYPE: PRT
<213> ORGANISM: Felis catus

<400> SEQUENCE: 41

Asn Arg Ile Phe Leu Pro Thr Val Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Leu Thr Leu Pro Phe Trp Ala Val Asp
    50                  55                  60

<210> SEQ ID NO 42
<211> LENGTH: 61
<212> TYPE: PRT
<213> ORGANISM: Bovine

<400> SEQUENCE: 42

Asn Arg Ile Phe Leu Pro Thr Val Tyr Ser Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Leu Thr Leu Pro Phe Trp Ala Val Asp
    50                  55                  60

<210> SEQ ID NO 43
<211> LENGTH: 61
<212> TYPE: PRT
<213> ORGANISM: Rat

<400> SEQUENCE: 43

Asn Arg Ile Phe Leu Pro Thr Ile Tyr Phe Ile Ile Phe Leu Thr Gly
1               5                   10                  15

Ile Val Gly Asn Gly Leu Val Ile Leu Val Met Gly Tyr Gln Lys Lys
            20                  25                  30

Leu Arg Ser Met Thr Asp Lys Tyr Arg Leu His Leu Ser Val Ala Asp
        35                  40                  45

Leu Leu Phe Val Ile Thr Leu Pro Phe Trp Ala Val Asp
    50                  55                  60

<210> SEQ ID NO 44
<211> LENGTH: 50
<212> TYPE: PRT
<213> ORGANISM: Homo sapiens

<400> SEQUENCE: 44

Pro Pro Leu Tyr Ser Leu Val Phe Val Ile Gly Leu Val Gly Asn Ile
1               5                   10                  15

Leu Val Val Leu Val Leu Val Gln Tyr Lys Arg Leu Lys Asn Met Thr
            20                  25                  30

Ser Ile Tyr Leu Leu Asn Leu Ala Ile Ser Asp Leu Leu Phe Leu Thr
        35                  40                  45

Leu Pro
    50

<210> SEQ ID NO 45
<211> LENGTH: 51
<212> TYPE: PRT
<213> ORGANISM: Mouse

<400> SEQUENCE: 45

Pro Pro Leu Tyr Ser Leu Val Phe Ile Ile Gly Val Val Gly Asn Val
1               5                   10                  15

Leu Met Ile Leu Val Leu Met Gln His Arg Arg Leu Gln Ser Met Thr
            20                  25                  30

Ser Ile Tyr Leu Phe Asn Leu Ala Val Ser Asp Leu Val Phe Leu Phe
        35                  40                  45

Thr Leu Pro
    50

<210> SEQ ID NO 46
<211> LENGTH: 51
<212> TYPE: PRT
<213> ORGANISM: Macaca mulatta

<400> SEQUENCE: 46

Pro Pro Leu Tyr Ser Leu Val Phe Val Ile Gly Val Val Gly Asn Leu
1               5                   10                  15

Leu Val Val Leu Val Leu Val Gln Tyr Lys Arg Leu Lys Asn Met Thr
            20                  25                  30

Asn Ile Tyr Leu Leu Asn Leu Ala Ile Ser Asp Leu Leu Phe Leu Phe
        35                  40                  45

Thr Leu Pro
    50

<210> SEQ ID NO 47
<211> LENGTH: 60
<212> TYPE: PRT
<213> ORGANISM: Homo sapiens

<400> SEQUENCE: 47

Pro Pro Leu Tyr Ser Leu Val Phe Ile Phe Gly Phe Val Gly Asn Met
1               5                   10                  15

Leu Val Val Leu Ile Leu Ile Asn Cys Lys Lys Leu Lys Cys Leu Thr
            20                  25                  30

Asp Ile Tyr Leu Leu Asn Leu Ala Ile Ser Asp Leu Leu Phe Leu Ile
        35                  40                  45

Thr Leu Pro Leu Trp Ala His Ser Ala Ala Asn Glu
    50                  55                  60

<210> SEQ ID NO 48
<211> LENGTH: 60
<212> TYPE: PRT
<213> ORGANISM: Mouse

<400> SEQUENCE: 48

Pro Pro Leu Tyr Ser Leu Val Phe Ile Phe Gly Phe Val Gly Asn Met
1               5                   10                  15

Leu Val Ile Ile Ile Leu Ile Gly Cys Lys Lys Leu Lys Ser Met Thr
            20                  25                  30

Asp Ile Tyr Leu Leu Asn Leu Ala Ile Ser Asp Leu Leu Phe Leu Leu
        35                  40                  45

-continued

Thr Leu Pro Phe Trp Ala His Tyr Ala Ala Asn Glu
    50                  55                  60

<210> SEQ ID NO 49
<211> LENGTH: 60
<212> TYPE: PRT
<213> ORGANISM: Rat

<400> SEQUENCE: 49

Pro Pro Leu Tyr Ser Leu Val Phe Ile Phe Gly Phe Val Gly Asn Met
1               5                   10                  15

Leu Val Ile Ile Ile Leu Ile Ser Cys Lys Lys Leu Lys Ser Met Thr
            20                  25                  30

Asp Ile Tyr Leu Phe Asn Leu Ala Ile Ser Asp Leu Leu Phe Leu Leu
        35                  40                  45

Thr Leu Pro Phe Trp Ala His Tyr Ala Ala Asn Glu
    50                  55                  60

<210> SEQ ID NO 50
<211> LENGTH: 60
<212> TYPE: PRT
<213> ORGANISM: Macaca mulatta

<400> SEQUENCE: 50

Pro Pro Leu Tyr Ser Leu Val Phe Ile Phe Gly Phe Val Gly Asn Met
1               5                   10                  15

Leu Val Val Leu Ile Leu Ile Asn Cys Lys Lys Leu Lys Ser Leu Thr
            20                  25                  30

Asp Ile Tyr Leu Leu Asn Leu Ala Ile Ser Asp Leu Leu Phe Leu Ile
        35                  40                  45

Thr Leu Pro Leu Trp Ala His Ser Ala Ala Asn Glu
    50                  55                  60

<210> SEQ ID NO 51
<211> LENGTH: 54
<212> TYPE: PRT
<213> ORGANISM: Homo sapiens

<400> SEQUENCE: 51

Pro Pro Leu Tyr Ser Leu Val Phe Val Phe Gly Leu Leu Gly Asn Ser
1               5                   10                  15

Val Val Val Leu Val Leu Phe Lys Tyr Lys Arg Leu Arg Ser Met Thr
            20                  25                  30

Asp Val Tyr Leu Leu Asn Leu Ala Ile Ser Asp Leu Leu Phe Val Phe
        35                  40                  45

Ser Leu Pro Phe Trp Gly
    50

<210> SEQ ID NO 52
<211> LENGTH: 54
<212> TYPE: PRT
<213> ORGANISM: Mouse

<400> SEQUENCE: 52

Pro Pro Leu Tyr Ser Leu Val Phe Leu Leu Gly Leu Phe Gly Asn Ser
1               5                   10                  15

Val Val Val Leu Val Leu Phe Lys Tyr Lys Arg Leu Lys Ser Met Thr
            20                  25                  30

Asp Val Tyr Leu Leu Asn Leu Ala Ile Ser Asp Leu Leu Phe Val Leu
        35                  40                  45

Ser Leu Pro Phe Trp Gly
    50

<210> SEQ ID NO 53
<211> LENGTH: 47
<212> TYPE: PRT
<213> ORGANISM: Homo sapiens

<400> SEQUENCE: 53

Pro Pro Leu Tyr Ser Leu Val Phe Ile Phe Gly Phe Val Gly Asn Met
1               5                   10                  15

Leu Val Ile Leu Ile Leu Ile Asn Cys Lys Arg Leu Lys Ser Met Thr
            20                  25                  30

Asp Ile Tyr Leu Leu Asn Leu Ala Ile Ser Asp Leu Phe Phe Leu
        35                  40                  45

<210> SEQ ID NO 54
<211> LENGTH: 47
<212> TYPE: PRT
<213> ORGANISM: Mouse

<400> SEQUENCE: 54

Pro Pro Leu Tyr Ser Leu Val Phe Ile Phe Gly Phe Val Gly Asn Met
1               5                   10                  15

Met Val Phe Leu Ile Leu Ile Ser Cys Lys Lys Leu Lys Ser Val Thr
            20                  25                  30

Asp Ile Tyr Leu Leu Asn Leu Ala Ile Ser Asp Leu Leu Phe Leu
        35                  40                  45

<210> SEQ ID NO 55
<211> LENGTH: 47
<212> TYPE: PRT
<213> ORGANISM: Papio hamadryas

<400> SEQUENCE: 55

Pro Pro Leu Tyr Ser Leu Val Phe Ile Phe Gly Phe Val Gly Asn Ile
1               5                   10                  15

Leu Val Val Leu Ile Leu Ile Asn Cys Lys Arg Leu Lys Ser Met Thr
            20                  25                  30

Asp Ile Tyr Leu Leu Asn Leu Ala Ile Ser Asp Leu Leu Phe Leu
        35                  40                  45

<210> SEQ ID NO 56
<211> LENGTH: 47
<212> TYPE: PRT
<213> ORGANISM: Erythrocebus patas

<400> SEQUENCE: 56

Pro Pro Leu Tyr Ser Leu Val Phe Ile Phe Gly Phe Val Gly Asn Ile
1               5                   10                  15

Leu Val Val Leu Ile Leu Ile Asn Cys Lys Arg Leu Lys Ser Met Thr
            20                  25                  30

Asp Ile Tyr Leu Leu Asn Leu Ala Ile Ser Asp Leu Leu Phe Leu
        35                  40                  45

<210> SEQ ID NO 57
<211> LENGTH: 47
<212> TYPE: PRT
<213> ORGANISM: Macaca mulatta

<400> SEQUENCE: 57

```
Pro Pro Leu Tyr Ser Leu Val Phe Ile Phe Gly Phe Val Gly Asn Ile
1               5                   10                  15

Leu Val Val Leu Ile Leu Ile Asn Cys Lys Arg Leu Lys Ser Met Thr
            20                  25                  30

Asp Ile Tyr Leu Leu Asn Leu Ala Ile Ser Asp Leu Leu Phe Leu
        35                  40                  45
```

<210> SEQ ID NO 58
<211> LENGTH: 47
<212> TYPE: PRT
<213> ORGANISM: Macaca nemestrina

<400> SEQUENCE: 58

```
Pro Pro Leu Tyr Ser Leu Val Phe Ile Phe Gly Phe Val Gly Asn Ile
1               5                   10                  15

Leu Val Val Leu Ile Leu Ile Asn Cys Lys Arg Leu Lys Ser Met Thr
            20                  25                  30

Asp Ile Tyr Leu Leu Asn Leu Ala Ile Ser Asp Leu Leu Phe Leu
        35                  40                  45
```

<210> SEQ ID NO 59
<211> LENGTH: 47
<212> TYPE: PRT
<213> ORGANISM: Macaca fascicularis

<400> SEQUENCE: 59

```
Pro Pro Leu Tyr Ser Leu Val Phe Ile Phe Gly Phe Val Gly Asn Ile
1               5                   10                  15

Leu Val Val Leu Ile Leu Ile Asn Cys Lys Arg Leu Lys Ser Met Thr
            20                  25                  30

Asp Ile Tyr Leu Leu Asn Leu Ala Ile Ser Asp Leu Leu Phe Leu
        35                  40                  45
```

<210> SEQ ID NO 60
<211> LENGTH: 47
<212> TYPE: PRT
<213> ORGANISM: Pan troglodytes

<400> SEQUENCE: 60

```
Pro Pro Leu Tyr Ser Leu Val Phe Ile Phe Gly Phe Val Gly Asn Met
1               5                   10                  15

Leu Val Ile Leu Ile Leu Ile Asn Cys Lys Arg Leu Lys Ser Met Thr
            20                  25                  30

Asp Ile Tyr Leu Leu Asn Leu Ala Ile Ser Asp Leu Phe Phe Leu
        35                  40                  45
```

<210> SEQ ID NO 61
<211> LENGTH: 47
<212> TYPE: PRT
<213> ORGANISM: Gorilla gorilla

<400> SEQUENCE: 61

```
Pro Pro Leu Tyr Ser Leu Val Phe Ile Phe Gly Phe Val Gly Asn Met
1               5                   10                  15

Leu Val Ile Leu Ile Leu Ile Asn Cys Lys Arg Leu Lys Ser Met Thr
            20                  25                  30

Asp Ile Tyr Leu Leu Asn Leu Ala Ile Ser Asp Leu Phe Phe Leu
        35                  40                  45
```

<210> SEQ ID NO 62
<211> LENGTH: 47

```
<212> TYPE: PRT
<213> ORGANISM: Rat

<400> SEQUENCE: 62

Pro Pro Leu Tyr Ser Leu Val Phe Ile Phe Gly Phe Val Gly Asn Met
1               5                   10                  15

Met Val Phe Leu Ile Leu Ile Ser Cys Lys Lys Leu Lys Ser Met Thr
                20                  25                  30

Asp Ile Tyr Leu Phe Asn Leu Ala Ile Ser Asp Leu Leu Phe Leu
                35                  40                  45

<210> SEQ ID NO 63
<211> LENGTH: 55
<212> TYPE: PRT
<213> ORGANISM: Homo sapiens

<400> SEQUENCE: 63

Phe Val Pro Ser Val Tyr Thr Gly Val Phe Val Ser Leu Pro Leu
1               5                   10                  15

Asn Ile Met Ala Ile Val Phe Ile Leu Lys Met Lys Val Lys Lys
                20                  25                  30

Pro Ala Val Val Tyr Met Leu His Leu Ala Thr Ala Asp Val Leu Phe
                35                  40                  45

Val Ser Val Leu Pro Phe Lys
    50                  55

<210> SEQ ID NO 64
<211> LENGTH: 55
<212> TYPE: PRT
<213> ORGANISM: Mouse

<400> SEQUENCE: 64

Phe Met Pro Ser Val Tyr Thr Ile Val Phe Ile Val Ser Leu Pro Leu
1               5                   10                  15

Asn Val Leu Ala Ile Ala Val Phe Val Leu Arg Met Lys Val Lys Lys
                20                  25                  30

Pro Ala Val Val Tyr Met Leu His Leu Ala Met Ala Asp Val Leu Phe
                35                  40                  45

Val Ser Val Leu Pro Phe Lys
    50                  55

<210> SEQ ID NO 65
<211> LENGTH: 55
<212> TYPE: PRT
<213> ORGANISM: Rat

<400> SEQUENCE: 65

Phe Ile Pro Ser Val Tyr Thr Phe Val Phe Ile Val Ser Leu Pro Leu
1               5                   10                  15

Asn Ile Leu Ala Ile Ala Val Phe Val Phe Arg Met Lys Val Lys Lys
                20                  25                  30

Pro Ala Val Val Tyr Met Leu His Leu Ala Met Ala Asp Val Leu Phe
                35                  40                  45

Val Ser Val Leu Pro Phe Lys
    50                  55

<210> SEQ ID NO 66
<211> LENGTH: 55
<212> TYPE: PRT
<213> ORGANISM: Cricetulus longicaudatus
```

-continued

```
<400> SEQUENCE: 66

Phe Ile Pro Ser Val Tyr Thr Phe Val Phe Val Ser Leu Pro Leu
1               5                   10                  15

Asn Ile Leu Ala Ile Ala Val Phe Val Leu Lys Met Lys Val Lys Lys
                20                  25                  30

Pro Ala Val Val Tyr Met Leu His Leu Ala Met Ala Asp Val Leu Phe
            35                  40                  45

Val Ser Val Leu Pro Leu Lys
    50                  55

<210> SEQ ID NO 67
<211> LENGTH: 55
<212> TYPE: PRT
<213> ORGANISM: Papio hamadryas

<400> SEQUENCE: 67

Phe Val Pro Ser Val Tyr Thr Gly Val Phe Val Ser Leu Pro Val
1               5                   10                  15

Asn Ile Met Ala Ile Val Val Phe Ile Leu Lys Met Lys Val Lys Lys
                20                  25                  30

Pro Ala Val Val Tyr Met Leu His Leu Ala Thr Ala Asp Val Leu Phe
            35                  40                  45

Val Ser Val Leu Pro Phe Lys
    50                  55

<210> SEQ ID NO 68
<211> LENGTH: 55
<212> TYPE: PRT
<213> ORGANISM: Xenopus laevis

<400> SEQUENCE: 68

Phe Val Pro Ser Leu Tyr Thr Val Val Phe Ile Val Gly Leu Pro Leu
1               5                   10                  15

Asn Leu Leu Ala Ile Ile Ile Phe Leu Phe Lys Met Lys Val Arg Lys
                20                  25                  30

Pro Ala Val Val Tyr Met Leu Asn Leu Ala Ile Ala Asp Val Phe Phe
            35                  40                  45

Val Ser Val Leu Pro Phe Lys
    50                  55

<210> SEQ ID NO 69
<211> LENGTH: 55
<212> TYPE: PRT
<213> ORGANISM: Homo sapiens

<400> SEQUENCE: 69

Phe Leu Pro Ile Val Tyr Thr Ile Val Phe Val Val Gly Leu Pro Ser
1               5                   10                  15

Asn Gly Met Ala Leu Trp Val Phe Leu Phe Arg Thr Lys Lys Lys His
                20                  25                  30

Pro Ala Val Ile Tyr Met Ala Asn Leu Ala Leu Ala Asp Leu Leu Ser
            35                  40                  45

Val Ile Trp Phe Pro Leu Lys
    50                  55

<210> SEQ ID NO 70
<211> LENGTH: 55
<212> TYPE: PRT
<213> ORGANISM: Mouse
```

-continued

<400> SEQUENCE: 70

Phe Leu Pro Val Val Tyr Ile Ile Val Phe Val Ile Gly Leu Pro Ser
1               5                   10                  15

Asn Gly Met Ala Leu Trp Ile Phe Leu Phe Arg Thr Lys Lys Lys His
            20                  25                  30

Pro Ala Val Ile Tyr Met Ala Asn Leu Ala Leu Ala Asp Leu Leu Ser
        35                  40                  45

Val Ile Trp Phe Pro Leu Lys
    50                  55

<210> SEQ ID NO 71
<211> LENGTH: 55
<212> TYPE: PRT
<213> ORGANISM: Rat

<400> SEQUENCE: 71

Phe Leu Pro Val Ile Tyr Ile Ile Val Phe Val Ile Gly Leu Pro Ser
1               5                   10                  15

Asn Gly Met Ala Leu Trp Val Phe Phe Phe Arg Thr Lys Lys Lys His
            20                  25                  30

Pro Ala Val Ile Tyr Met Ala Asn Leu Ala Leu Ala Asp Leu Leu Ser
        35                  40                  45

Val Ile Trp Phe Pro Leu Lys
    50                  55

<210> SEQ ID NO 72
<211> LENGTH: 54
<212> TYPE: PRT
<213> ORGANISM: Homo sapiens

<400> SEQUENCE: 72

Leu Ile Pro Ala Ile Tyr Leu Leu Val Phe Val Val Gly Val Pro Ala
1               5                   10                  15

Asn Ala Val Thr Leu Trp Met Leu Phe Phe Arg Thr Arg Ser Ile Cys
            20                  25                  30

Thr Thr Val Phe Tyr Thr Asn Leu Ala Ile Ala Asp Phe Leu Phe Cys
        35                  40                  45

Val Thr Leu Pro Phe Lys
    50

<210> SEQ ID NO 73
<211> LENGTH: 54
<212> TYPE: PRT
<213> ORGANISM: Mouse

<400> SEQUENCE: 73

Val Ile Pro Ala Ile Tyr Ile Leu Phe Val Val Gly Val Pro Ser
1               5                   10                  15

Asn Ile Val Thr Leu Trp Lys Leu Ser Leu Arg Thr Lys Ser Ile Ser
            20                  25                  30

Leu Val Ile Phe His Thr Asn Leu Ala Ile Ala Asp Leu Leu Phe Cys
        35                  40                  45

Val Thr Leu Pro Phe Lys
    50

<210> SEQ ID NO 74
<211> LENGTH: 54
<212> TYPE: PRT
<213> ORGANISM: Rat

<400> SEQUENCE: 74

Val Ile Pro Ala Ile Tyr Ile Leu Val Phe Val Ile Gly Val Pro Ala
1               5                   10                  15

Asn Ile Val Thr Leu Trp Lys Leu Ser Ser Arg Thr Lys Ser Ile Cys
                20                  25                  30

Leu Val Ile Phe His Thr Asn Leu Ala Ile Ala Asp Leu Leu Phe Cys
            35                  40                  45

Val Thr Leu Pro Phe Lys
            50

<210> SEQ ID NO 75
<211> LENGTH: 54
<212> TYPE: PRT
<213> ORGANISM: Homo sapiens

<400> SEQUENCE: 75

Leu Val Pro Ala Leu Tyr Gly Leu Val Leu Val Gly Leu Pro Ala
1               5                   10                  15

Asn Gly Leu Ala Leu Trp Val Leu Ala Thr Gln Ala Pro Arg Leu Pro
                20                  25                  30

Ser Thr Met Leu Leu Met Asn Leu Ala Thr Ala Asp Leu Leu Leu Ala
            35                  40                  45

Leu Ala Leu Pro Pro Arg
            50

<210> SEQ ID NO 76
<211> LENGTH: 54
<212> TYPE: PRT
<213> ORGANISM: Mouse

<400> SEQUENCE: 76

Leu Val Pro Ala Leu Tyr Gly Leu Val Val Ala Val Gly Leu Pro Ala
1               5                   10                  15

Asn Gly Leu Ala Leu Trp Val Leu Ala Thr Arg Val Pro Arg Leu Pro
                20                  25                  30

Ser Thr Ile Leu Leu Thr Asn Leu Ala Val Ala Asp Ser Leu Leu Ala
            35                  40                  45

Leu Val Pro Pro Pro Arg
            50

<210> SEQ ID NO 77
<211> LENGTH: 54
<212> TYPE: PRT
<213> ORGANISM: Rat

<400> SEQUENCE: 77

Leu Val Pro Ala Ile Tyr Gly Leu Val Val Val Gly Leu Pro Ala
1               5                   10                  15

Asn Gly Leu Ala Leu Trp Val Leu Ala Thr Arg Val Pro Arg Leu Pro
                20                  25                  30

Ser Thr Ile Leu Leu Met Asn Leu Ala Val Ala Asp Leu Leu Leu Ala
            35                  40                  45

Leu Val Leu Pro Pro Arg
            50

<210> SEQ ID NO 78
<211> LENGTH: 50
<212> TYPE: PRT
<213> ORGANISM: Homo sapiens

<400> SEQUENCE: 78

Lys Leu Thr Ser Val Val Phe Ile Leu Ile Cys Cys Phe Ile Ile Leu
1               5                   10                  15

Glu Asn Ile Phe Val Leu Leu Thr Ile Trp Lys Thr Lys Lys Phe His
            20                  25                  30

Arg Pro Met Tyr Tyr Phe Ile Gly Asn Leu Ala Leu Ser Asp Leu Leu
        35                  40                  45

Ala Gly
    50

<210> SEQ ID NO 79
<211> LENGTH: 50
<212> TYPE: PRT
<213> ORGANISM: Mouse

<400> SEQUENCE: 79

Lys Leu Thr Ser Val Val Phe Ile Leu Ile Cys Cys Phe Ile Ile Leu
1               5                   10                  15

Glu Asn Ile Phe Val Leu Leu Thr Ile Trp Lys Thr Lys Lys Phe His
            20                  25                  30

Arg Pro Met Tyr Tyr Phe Ile Gly Asn Leu Ala Leu Ser Asp Leu Leu
        35                  40                  45

Ala Gly
    50

<210> SEQ ID NO 80
<211> LENGTH: 50
<212> TYPE: PRT
<213> ORGANISM: Rat

<400> SEQUENCE: 80

Lys Leu Thr Ser Val Val Phe Ile Leu Ile Cys Cys Leu Ile Ile Leu
1               5                   10                  15

Glu Asn Ile Phe Val Leu Leu Thr Ile Trp Lys Thr Lys Lys Phe His
            20                  25                  30

Arg Pro Met Tyr Tyr Phe Ile Gly Asn Leu Ala Leu Ser Asp Leu Leu
        35                  40                  45

Ala Gly
    50

<210> SEQ ID NO 81
<211> LENGTH: 50
<212> TYPE: PRT
<213> ORGANISM: Homo sapiens

<400> SEQUENCE: 81

Lys Leu Val Met Gly Leu Gly Ile Thr Val Cys Ile Phe Ile Met Leu
1               5                   10                  15

Ala Asn Leu Leu Val Met Val Ala Ile Tyr Val Asn Arg Arg Phe His
            20                  25                  30

Phe Pro Ile Tyr Tyr Leu Met Ala Asn Leu Ala Ala Ala Asp Phe Phe
        35                  40                  45

Ala Gly
    50

<210> SEQ ID NO 82
<211> LENGTH: 50
<212> TYPE: PRT
<213> ORGANISM: Mouse

<400> SEQUENCE: 82

Lys Leu Val Met Gly Leu Gly Ile Thr Val Cys Val Phe Ile Met Leu
1               5                   10                  15

Ala Asn Leu Leu Val Met Val Ala Ile Tyr Val Asn Arg Arg Phe His
            20                  25                  30

Phe Pro Ile Tyr Tyr Leu Met Ala Asn Leu Ala Ala Ala Asp Phe Phe
        35                  40                  45

Ala Gly
    50

<210> SEQ ID NO 83
<211> LENGTH: 50
<212> TYPE: PRT
<213> ORGANISM: Sheep

<400> SEQUENCE: 83

Lys Leu Val Met Gly Leu Gly Ile Thr Val Cys Ile Phe Ile Met Leu
1               5                   10                  15

Ala Asn Leu Leu Val Met Val Ala Ile Tyr Val Asn Arg Arg Phe His
            20                  25                  30

Phe Pro Ile Tyr Tyr Leu Met Ala Asn Leu Ala Ala Ala Asp Phe Phe
        35                  40                  45

Ala Gly
    50

<210> SEQ ID NO 84
<211> LENGTH: 50
<212> TYPE: PRT
<213> ORGANISM: Bovine

<400> SEQUENCE: 84

Lys Leu Val Met Gly Leu Gly Ile Thr Val Cys Ile Phe Ile Met Leu
1               5                   10                  15

Ala Asn Leu Leu Val Met Val Ala Ile Tyr Val Asn Arg Arg Phe His
            20                  25                  30

Phe Pro Ile Tyr Tyr Leu Met Ala Asn Leu Ala Ala Ala Asp Phe Phe
        35                  40                  45

Ala Gly
    50

<210> SEQ ID NO 85
<211> LENGTH: 50
<212> TYPE: PRT
<213> ORGANISM: Homo sapiens

<400> SEQUENCE: 85

Thr Leu Thr Thr Val Leu Phe Leu Val Ile Cys Ser Phe Ile Val Leu
1               5                   10                  15

Glu Asn Leu Met Val Leu Ile Ala Ile Trp Lys Asn Asn Lys Phe His
            20                  25                  30

Asn Arg Met Tyr Phe Phe Ile Gly Asn Leu Ala Leu Cys Asp Leu Leu
        35                  40                  45

Ala Gly
    50

<210> SEQ ID NO 86
<211> LENGTH: 50
<212> TYPE: PRT
<213> ORGANISM: Mouse

-continued

<400> SEQUENCE: 86

Leu Ile Thr Thr Ile Leu Phe Leu Val Thr Cys Ser Phe Ile Val Leu
1               5                   10                  15

Glu Asn Leu Met Val Leu Ile Ala Ile Trp Lys Asn Asn Lys Phe His
            20                  25                  30

Asn Arg Met Tyr Phe Phe Ile Gly Asn Leu Ala Leu Cys Asp Leu Leu
        35                  40                  45

Ala Gly
    50

<210> SEQ ID NO 87
<211> LENGTH: 50
<212> TYPE: PRT
<213> ORGANISM: Fugu rubripes

<400> SEQUENCE: 87

Asp Pro Lys Thr Ile Ala Phe Leu Val Val Cys Ser Phe Ile Ile Leu
1               5                   10                  15

Glu Asn Leu Thr Val Leu Leu Ala Ile Trp Lys Asn His Arg Phe His
            20                  25                  30

Asn Arg Met Tyr Phe Phe Ile Gly Asn Leu Ala Leu Cys Asp Leu Leu
        35                  40                  45

Ala Ser
    50

<210> SEQ ID NO 88
<211> LENGTH: 50
<212> TYPE: PRT
<213> ORGANISM: Homo sapiens

<400> SEQUENCE: 88

Val Val Val Val Ala Leu Gly Leu Thr Val Ser Val Leu Val Leu Leu
1               5                   10                  15

Thr Asn Leu Leu Val Ile Ala Ala Ile Ala Ser Asn Arg Arg Phe His
            20                  25                  30

Gln Pro Ile Tyr Tyr Leu Leu Gly Asn Leu Ala Ala Ala Asp Leu Phe
        35                  40                  45

Ala Gly
    50

<210> SEQ ID NO 89
<211> LENGTH: 50
<212> TYPE: PRT
<213> ORGANISM: Mouse

<400> SEQUENCE: 89

Val Val Val Val Ala Leu Gly Leu Thr Val Ser Val Leu Val Leu Leu
1               5                   10                  15

Thr Asn Leu Leu Val Ile Ala Ala Ile Ala Ser Asn Arg Arg Phe His
            20                  25                  30

Gln Pro Ile Tyr Tyr Leu Leu Gly Asn Leu Ala Ala Ala Asp Leu Phe
        35                  40                  45

Ala Gly
    50

<210> SEQ ID NO 90
<211> LENGTH: 50
<212> TYPE: PRT
<213> ORGANISM: Macaca fascicularis

```
<400> SEQUENCE: 90

Val Val Val Val Ala Leu Gly Leu Thr Val Ser Val Leu Val Leu Leu
1               5                   10                  15

Thr Asn Leu Leu Val Ile Ala Ala Ile Ala Ser Asn Arg Arg Phe His
                20                  25                  30

Gln Pro Ile Tyr Tyr Leu Leu Gly Asn Leu Ala Ala Ala Asp Leu Phe
            35                  40                  45

Ala Gly
    50

<210> SEQ ID NO 91
<211> LENGTH: 50
<212> TYPE: PRT
<213> ORGANISM: homo sapians

<400> SEQUENCE: 91

Gln Val Ala Ser Ala Phe Ile Val Ile Leu Cys Cys Ala Ile Val Val
1               5                   10                  15

Glu Asn Leu Leu Val Leu Ile Ala Val Ala Arg Asn Ser Lys Phe His
                20                  25                  30

Ser Ala Met Tyr Leu Phe Leu Gly Asn Leu Ala Ala Ser Asp Leu Leu
            35                  40                  45

Ala Gly
    50

<210> SEQ ID NO 92
<211> LENGTH: 50
<212> TYPE: PRT
<213> ORGANISM: Mouse

<400> SEQUENCE: 92

Lys Val Ala Ser Ala Phe Ile Ile Ile Leu Cys Cys Ala Ile Val Val
1               5                   10                  15

Glu Asn Leu Leu Val Leu Ile Ala Val Ala Arg Asn Ser Lys Phe His
                20                  25                  30

Ser Ala Met Tyr Leu Phe Leu Gly Asn Leu Ala Ala Ser Asp Leu Leu
            35                  40                  45

Ala Gly
    50

<210> SEQ ID NO 93
<211> LENGTH: 50
<212> TYPE: PRT
<213> ORGANISM: Rat

<400> SEQUENCE: 93

Lys Val Ala Ser Ala Phe Ile Ile Ile Leu Cys Cys Ala Ile Val Val
1               5                   10                  15

Glu Asn Leu Leu Val Leu Ile Ala Val Ala Arg Asn Ser Lys Phe His
                20                  25                  30

Ser Ala Met Tyr Leu Phe Leu Gly Asn Leu Ala Ala Ser Asp Leu Leu
            35                  40                  45

Ala Gly
    50

<210> SEQ ID NO 94
<211> LENGTH: 50
<212> TYPE: PRT
<213> ORGANISM: homo sapians
```

-continued

```
<400> SEQUENCE: 94

Gly Ala Leu Arg Gly Leu Ser Val Ala Ala Ser Cys Leu Val Val Leu
1               5                   10                  15

Glu Asn Leu Leu Val Leu Ala Ala Ile Thr Ser His Met Arg Ser Arg
            20                  25                  30

Arg Trp Val Tyr Tyr Cys Leu Val Asn Ile Thr Leu Ser Asp Leu Leu
        35                  40                  45

Thr Gly
    50

<210> SEQ ID NO 95
<211> LENGTH: 50
<212> TYPE: PRT
<213> ORGANISM: Mouse

<400> SEQUENCE: 95

Gly Met Leu Arg Gly Pro Ser Val Ala Ala Gly Cys Leu Val Val Leu
1               5                   10                  15

Glu Asn Ala Met Val Leu Ala Ala Ile Ala Ile Tyr Met Arg Ser Arg
            20                  25                  30

Arg Trp Val Tyr Tyr Cys Leu Asn Ile Thr Leu Ser Asp Leu Leu
        35                  40                  45

Thr Gly
    50

<210> SEQ ID NO 96
<211> LENGTH: 50
<212> TYPE: PRT
<213> ORGANISM: Brachypodium retusum

<400> SEQUENCE: 96

Ser Ser Leu Asn Ile Leu Phe Val Val Ile Cys Ser Ile Ile Leu
1               5                   10                  15

Glu Asn Leu Leu Val Leu Ile Ala Val Phe Arg Asn Lys Lys Phe His
            20                  25                  30

Ser Ala Met Phe Phe Phe Ile Gly Asn Leu Ala Phe Ser Asp Leu Leu
        35                  40                  45

Ala Gly
    50

<210> SEQ ID NO 97
<211> LENGTH: 50
<212> TYPE: PRT
<213> ORGANISM: Homo sapians

<400> SEQUENCE: 97

Val Ile Val Leu Cys Val Gly Thr Phe Phe Cys Leu Phe Ile Phe Phe
1               5                   10                  15

Ser Asn Ser Leu Val Ile Ala Ala Val Ile Lys Asn Arg Lys Phe His
            20                  25                  30

Phe Pro Phe Tyr Tyr Leu Leu Ala Asn Leu Ala Ala Ala Asp Phe Phe
        35                  40                  45

Ala Gly
    50

<210> SEQ ID NO 98
<211> LENGTH: 50
<212> TYPE: PRT
<213> ORGANISM: Mouse
```

```
<400> SEQUENCE: 98

Val Ile Val Leu Cys Val Gly Thr Phe Phe Cys Leu Phe Ile Phe Phe
1               5                   10                  15

Ser Asn Ser Leu Val Ile Ala Ala Val Ile Thr Asn Arg Lys Phe His
            20                  25                  30

Phe Pro Phe Tyr Tyr Leu Leu Ala Asn Leu Ala Ala Ala Asp Phe Phe
        35                  40                  45

Ala Gly
    50

<210> SEQ ID NO 99
<211> LENGTH: 50
<212> TYPE: PRT
<213> ORGANISM: Rat

<400> SEQUENCE: 99

Val Ile Val Leu Cys Val Gly Thr Phe Phe Cys Leu Phe Ile Phe Phe
1               5                   10                  15

Ser Asn Ser Leu Val Ile Ala Ala Val Ile Thr Asn Arg Lys Phe His
            20                  25                  30

Phe Pro Phe Tyr Tyr Leu Leu Ala Asn Leu Ala Ala Ala Asp Phe Phe
        35                  40                  45

Ala Gly
    50

<210> SEQ ID NO 100
<211> LENGTH: 51
<212> TYPE: PRT
<213> ORGANISM: Homo sapians

<400> SEQUENCE: 100

Trp Gln Ile Val Leu Trp Ala Ala Ala Tyr Thr Val Ile Val Val Thr
1               5                   10                  15

Ser Val Val Gly Asn Val Val Val Met Trp Ile Ile Leu Ala His Lys
            20                  25                  30

Arg Met Arg Thr Val Thr Asn Tyr Phe Leu Val Asn Leu Ala Phe Ala
        35                  40                  45

Glu Ala Ser
    50

<210> SEQ ID NO 101
<211> LENGTH: 51
<212> TYPE: PRT
<213> ORGANISM: Mouse

<400> SEQUENCE: 101

Trp Gln Ile Val Leu Trp Ala Ala Ala Tyr Thr Val Ile Val Val Thr
1               5                   10                  15

Ser Val Val Gly Asn Val Val Val Ile Trp Ile Ile Leu Ala His Lys
            20                  25                  30

Arg Met Arg Thr Val Thr Asn Tyr Phe Leu Val Asn Leu Ala Phe Ala
        35                  40                  45

Glu Ala Cys
    50

<210> SEQ ID NO 102
<211> LENGTH: 51
<212> TYPE: PRT
<213> ORGANISM: Rat
```

-continued

```
<400> SEQUENCE: 102

Trp Gln Ile Val Leu Trp Ala Ala Ala Tyr Thr Val Ile Val Val Thr
1               5                   10                  15

Ser Val Val Gly Asn Val Val Val Ile Trp Ile Ile Leu Ala His Lys
            20                  25                  30

Arg Met Arg Thr Val Thr Asn Tyr Phe Leu Val Asn Leu Ala Phe Ala
        35                  40                  45

Glu Ala Cys
    50

<210> SEQ ID NO 103
<211> LENGTH: 51
<212> TYPE: PRT
<213> ORGANISM: Cavia porcellus

<400> SEQUENCE: 103

Trp Gln Ile Val Leu Trp Ala Ala Ala Tyr Thr Val Ile Val Val Thr
1               5                   10                  15

Ser Val Val Gly Asn Val Val Val Met Trp Ile Ile Leu Ala His Lys
            20                  25                  30

Arg Met Arg Thr Val Thr Asn Tyr Phe Leu Val Asn Leu Ala Phe Ala
        35                  40                  45

Glu Ala Ser
    50

<210> SEQ ID NO 104
<211> LENGTH: 51
<212> TYPE: PRT
<213> ORGANISM: Rana catesbeiana

<400> SEQUENCE: 104

Trp Gln Ile Ala Leu Trp Ser Val Ala Tyr Ser Ile Ile Val Ile Val
1               5                   10                  15

Ser Leu Val Gly Asn Ile Ile Val Met Trp Ile Ile Ile Ala His Lys
            20                  25                  30

Arg Met Arg Thr Val Thr Asn Tyr Phe Leu Val Asn Leu Ala Phe Ala
        35                  40                  45

Glu Ala Ser
    50
```